US007851609B2

(12) United States Patent
Jackson

(10) Patent No.: US 7,851,609 B2
(45) Date of Patent: Dec. 14, 2010

(54) ***CHLAMYDIA* PMP PROTEINS, GENE SEQUENCES AND USES THEREOF**

(75) Inventor: W. James Jackson, Marriottsville, MD (US)

(73) Assignee: Emergent Product Development Gaithersburg Inc., Gaithersburg, MD (US)

(*) Notice: Subject to any disclaimer, the term of this patent is extended or adjusted under 35 U.S.C. 154(b) by 71 days.

(21) Appl. No.: 11/781,199

(22) Filed: Jul. 20, 2007

(65) Prior Publication Data

US 2007/0292437 A1 Dec. 20, 2007

Related U.S. Application Data

(60) Division of application No. 10/398,248, filed as application No. PCT/US01/30345 on Sep. 28, 2001, now Pat. No. 7,731,980, which is a continuation-in-part of application No. 09/677,752, filed on Oct. 2, 2000, now Pat. No. 7,537,772.

(51) Int. Cl.
*C07H 21/04* (2006.01)
*C07H 21/02* (2006.01)
*A61K 39/38* (2006.01)
*A61K 39/118* (2006.01)

(52) U.S. Cl. ................. 536/23.7; 424/184.1; 424/263.1

(58) Field of Classification Search ....................... None
See application file for complete search history.

(56) References Cited

U.S. PATENT DOCUMENTS 4,427,782 A 1/1984 Caldwell et al.
5,071,962 A 12/1991 Morrison et al.
5,516,638 A 5/1996 Urnovitz et al.
5,679,547 A 10/1997 Krivan et al.
5,721,115 A 2/1998 Krivan et al.
5,725,863 A 3/1998 Daniels et al.
5,770,714 A 6/1998 Agabian et al.
5,869,608 A 2/1999 Caldwell et al.
5,965,141 A 10/1999 Briles et al.
5,976,544 A 11/1999 Charles et al.
6,166,177 A 12/2000 Probst et al.
6,432,916 B1 * 8/2002 Probst et al. ................... 514/2
6,447,779 B1 9/2002 Probst et al.
6,448,234 B1 9/2002 Fling
6,559,294 B1 5/2003 Griffais et al.
6,565,856 B1 5/2003 Skeiky et al.
6,642,023 B1 11/2003 Jackson et al.
6,887,843 B1 5/2005 Jackson et al.
2002/0061848 A1 5/2002 Bhatia et al.
2004/0037846 A1 2/2004 Jackson
2004/0067524 A1 4/2004 Jackson et al.
2004/0137005 A1 7/2004 Jackson et al.
2005/0048557 A1 3/2005 Jackson et al.

FOREIGN PATENT DOCUMENTS

WO WO 96/40893 A1 12/1996
WO WO 99/27105 A2 6/1999
WO WO 99/28474 A2 6/1999
WO WO 99/28475 * 6/1999
WO WO 99/28475 A2 6/1999
WO WO 00/27994 A2 5/2000
WO WO 00/34483 * 6/2000
WO WO 00/34483 A2 6/2000
WO WO 00/34488 A2 6/2000
WO WO 01/40474 A2 6/2001
WO WO 02/08267 A2 1/2002
WO WO 02/28998 A2 4/2002
WO WO 02/062380 A2 8/2002

OTHER PUBLICATIONS

Bannantine, J.P. and Rockey, D.D., "Use of a primate model system to identify *Chlamydia trachomatis* protein antigens recognized uniquely in the context of infection," *Microbiol.145*:2077-2085, High Wire Press (Aug. 1999).
Birkelund, S., et al., "Chemical Cross-Linking of *Chlamydia trachomatis*," *Infect. Immun. 56*:654-659, American Society for Microbiology (1988).
Buendia, A.J., et al., "Localization by immunoelectron microscopy of antigens of *Chlamydia psittaci* suitable for diagnosis or vaccine development," *FEMS Microbiol. Lett. 150*:113-119, Elsevier Science B.V. (1997).
Caldwell, H.D., et al., "Purification and Partial Characterization of the Major Outer Membrane Protein of *Chlamydia trachomatis*," *Infect. Immun. 31*:1161-1176, American Society for Microbiology (1981).
Cerrone, M.C., et al., "Cloning and Sequence of the Gene for Heat Shock Protein 60 from *Chlamydia trachomatis* and Immunological Reactivity of the Protein," *Infect. Immun. 59*:79-90, American Society for Microbiology (1991).
Chen, J.C.-R., and Stephens, R.S., "Trachoma and LGV biovars of *Chlamydia trachomatis* share the same glycosaminoglycan-dependent mechanism for infection of eukaryotic cells," *Molec. Microbiol. 11*:501-507, Blackwell Scientific Publications (1994).
De Sa, C., et al., "An Oligomer of the Major Outer Membrane Protein of *Chlamydia psittaci* Is Recognized by Monoclonal Antibodies Which Protect Mice from Abortion," *Infect. Immun. 63*:4912-4916, American Society for Microbiology (1995).

(Continued)

*Primary Examiner*—Vanessa L. Ford
(74) *Attorney, Agent, or Firm*—Sterne, Kessler, Goldstein and Fox P.L.L.C.

(57) ABSTRACT

The invention discloses the *Chlamydia* PMPE and PMPI polypeptide, polypeptides derived therefrp, (PMP-derived polypeptides), nucleotide sequences encoding said polypeptides, antibodies that specifically bind the PMP polypeptides and PMP-derived polypeptides and T-cells specific for PMP polypeptides and PMP-derived polypeptides. Also disclosed are prophylactic and therapeutic compositions, including immunogenic compositions, e.g., vaccines, comprising PMP polypeptides or PMP-derived polypeptides or antibodies thereto. The invention additionally discloses methods of inducing in animals an immune response to *Chlamydia* cells, *Chlamydia* elementary bodies, and/or cells expressing Chlamydial proteins, e.g., cell infected with *Chlamydia*.

44 Claims, 18 Drawing Sheets

OTHER PUBLICATIONS

Figure 1:
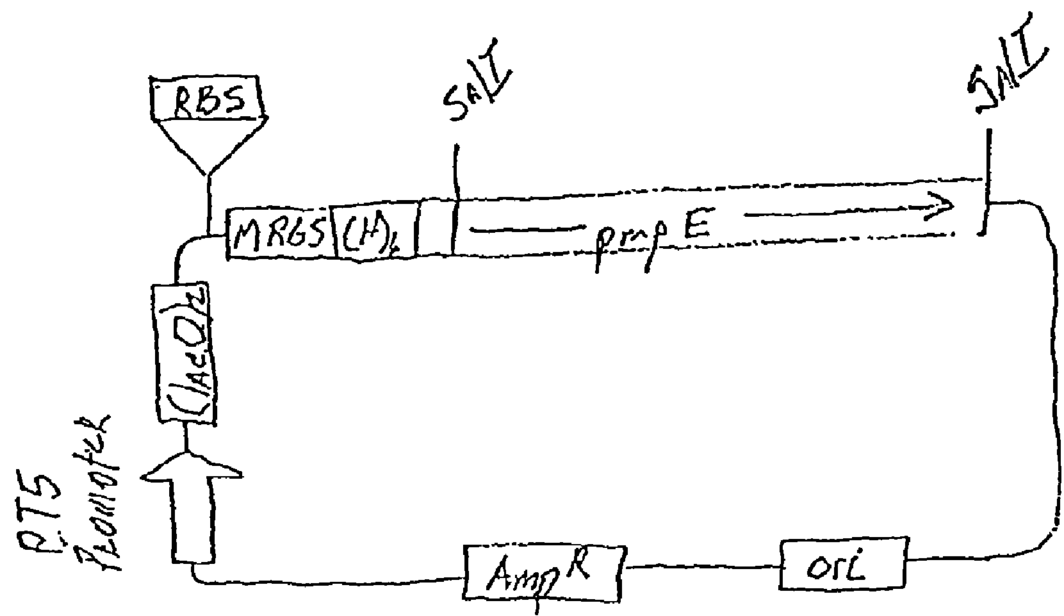

Deslauriers, M., et al., "Identification of Murine Protective Epitopes on the *Porphyromonas gingivalis* Fimbrillin Molecule," *Infect. Immun. 64*:434-440, American Society for Microbiology (1996).
Herring, A.J., et al., "Sequence analysis of the major outer membrane protein gene of an ovine abortion strain of *Chlamydia psittaci,*" *FEMS Microbiol. Lett. 65*:153-158, Elsevier Science B.V. (1989).
Ji, Y., et al., "Intranasal Immunization with C5a Peptidase Prevents Nasopharyngeal Colonization of Mice by the Group A *Streptococcus,*" *Infect. Immun. 65*:2080-2087, American Society for Microbiology (1997).
Li, C.H., et al., "β-Endorphin omission analogs: Dissociation of immunoreactivity from other biological activities," *Proc. Natl. Acad. Sci. USA 77*:3211-3214, National Academy of Sciences (1980).
Murdin, A.D., et al., "A Poliovirus Hybrid Expressing a Neutralization Epitope from the Major Outer Membrane Protein of *Chlamydia trachomatis* Is Highly Immunogenic," *Infect. Immun. 61*:4406-4414, American Society for Microbiology (1993).
Murdin, A.D., et al., "Poliovirus Hybrids Expressing Neutralization Epitopes from Variable Domains I and IV of the Major Outer Membrane Protein of *Chlamydia trachomatis* Elicit Broadly Cross-Reactive *C. trachomatis*-Neutralizing Antibodies," *Infect. Immun. 63*:1116-1121, American Society for Microbiology (1995).
Nilsson, I.-M., et al., "Vaccination with a Recombinant Fragment of Collagen Adhesion Provides Protection against *Staphylococcus Aureus*—mediated Septic Death," *J Clin. Invest. 101*:2640-2649, American Society for Clinical Investigation, Inc. (1998).
Pal, S., et al., "Immunogenic and protective ability of the two developmental forms of *Chlamydiae* in a mouse model of infertility," *Vaccine 18*:752-761, Elsevier Science Ltd. (Nov. 1999).
Peterson, E.M., et al., "Intranasal immunization with *Chlamydia trachomatis*, serovar E, protects from a subsequent vaginal challenge with the homologous serovar," *Vaccine 17*:2901-2907, Elsevier Science B.V. (Jul. 1999).
Rostand, K.S. and Esko, J.D., "Microbial Adherence to and Invasion through Proteoglycans," *Infect. Immun. 65*:1-8, American Society for Microbiology (1997).
Sexton, J.L., et al., "Vaccination of Sheep against *Fasciola hepatica* with Glutathione S-Transferase," *J. Immunol. 152*:1861-1872, The American Association of Immunologists (1994).
Stephens, R.S., et al., "Sequence Analysis of the Major Outer Membrane Protein Gene from *Chlamydia trachomatis* Serovar $L_2$," *J. Bacteriol. 168*:1277-1282, American Society for Microbiology (1986).
Stephens, R.S., "Molecular mimicry and *Chlamydia trachomatis* infection of eukaryotic cells," *Trends Microbiol. 2*:99-101, Elsevier Trends Journals (1994).
Stephens, R.S., "Chlamydial Genomics and Vaccine Antigen Discovery," *J. Infect. Dis. 181*:S521-S523, University of Chicago Press (Jun. 2000).
Su, H., et al., "A recombinant *Chlamydia trachomatis* major outer membrane protein binds to heparan sulfate receptors on epithelial cells," *Proc. Natl. Acad. Sci. USA 93*:11143-11148, National Academy of Sciences (1996).
Swanson, A.F. and Kuo, C.-C., "Identification of Lectin-Binding Proteins in *Chlamydia* Species," *Infect. Immun. 58*:502-507, American Society for Microbiology (1990).
Tan, T.-W., et al., "Protection of Sheep against *Chlamydia psittaci* Infection with a Subcellular Vaccine Containing the Major Outer Membrane Protein," *Infect. Immun. 58*:3101-3108, American Society for Microbiology (1990).
Wagar, E.A. and Stephens, R.S., "Developmental-Form-Specific DNA-Binding Proteins in *Chlamydia* spp.," *Infect. Immun. 56*:1678-1684, American Society for Microbiology (1988).
Zhang, Y.-X., et al., "The nucleotide sequence of major outer membrane protein gene of *Chlamydia trachomatis* serovar F," *Nucl. Acids Res. 18*:1061, IRL Press (1990).
Zhang, J.P. and Stephens, R.S., "Mechanisms of *C. trachomatis* Attachment to Eukaryotic Host Cells," *Cell 69*:861-869, Cell Press (1992).
NCBI Entrez, PubMed Accession No. E71460, Stephens, R.S., et al. (first available Apr. 2000).
NCBI Entrez, PubMed Accession No. B71460, Stephens, R.S., et al. (first available Apr. 1999).
NCBI Entrez, PubMed Accession No. AAC68472, Stephens, R.S., et al. (first available Apr. 1998).
Probst, P., et al., Sequence Alignment WO 99/34483 (2000).
Griffais, R., Sequence Alignment from WO 99/28475 A2 (1999).
Co-pending and commonly-owned U.S. Appl. No. 08/942,596, inventors Jackson, W. James, et al., filed Oct. 2, 1997 (Not Published).
Co-pending and commonly-owned U.S. Appl. No. 09/677,752, inventor Jackson, W.J., filed Oct. 3, 2000 (as amended) (Not Published).
Co-pending and commonly-owned U.S. Appl. No. 11/781,203, inventor Jackson, W. James, filed Jul. 20, 2007 (Not Published).
Christiansen, G., et al., "Potential Relevance of *Chlamydia pneumoniae* Surface Proteins to an Effective Vaccine," *J. Infect. Dis. 181(Suppl. 3)*:S528-S537, Infectious Diseases Society of America (Jun. 2000).
Creighton, T.E., ed., *Protein Structure: A Practical Approach*, Oxford University Press, New York, NY, pp. 184-186 (1989).
Creighton, T.E., ed., *Protein: Structure and Molecular Properties*, W.H. Freeman & Co., New York, NY, pp. 314-315 (1984).
Exner, M.M., et al., "Protection Elicited by Native Outer Membrane Protein Oms66 (p66) against Host-Adapted *Borrelia burgdorferi*:Conformational Nature of Bactericidal Epitopes," *Infect. Immun. 68*:2647-2654, American Society for Microbiology (May 2000).
Fox, J.L., "AIDS Product Development Follows its Own Rules," *Biootechnol. 12*:1329-1331, Nature Publishing Co. (1994).
Grimwood, J., et al., "Expression of *Chlamydia pneumoniae* Polymorphic Membrane Protein Family Genes," *Infect. Immun. 69*:2383-2389, American Society for Microbiology (Apr. 2001).
Gu, X.X., et al., "Synthesis and Characterization of Lipooligosaccharide-based Conjugates as Vaccine Candidates for *Moraxella (Branhamella) catarrhalis*," Infect. Immun. 66:1891-1897, American Society for Microbiology (1998).
Hou, V.C., et al., "Conformational Epitopes Recognized by Protective Anti-Neisserial Surface Protein A Antibodies," *Inject. Immun. 71*:6844-6849, American Society for Microbiology (Dec. 2003).
Kim, S.-K., et al., "Induction of HLA Class I-Restricted CD8+ CTLs Specific for the Major Outer Membrane Protein of *Chlamydia trachomatis* in Human Genital Tract Infections," *J. Immunol. 162*:6855-6866, The American Association of Immunologists (1999).
Kyd, J., et al., "Investigation of Mucosal Immunisation in Pulmonary Clearance of *Moraxella (Branhamella) catarrhalis," Vaccine 18*:398-406, Elsevier Science (Oct. 1999).
Longbottom, D., et al., "Immunoelectron microscopic localisation of the OMP90 family on the outer membrane surface of *Chlamydia psittaci," FEMS Microbiol. Lett. 164*:111-117,, Elsevier Science B.V. (1998).
Longbottom, D., et al., "Molecular Cloning and Characterization of the Genes Coding for the Highly Immunogenic Cluster of 90-Kilodalton Envelope Proteins from the *Chlamydia psittaci* Subtype That Causes Abortion in Sheep," *Infect. Immun. 66*:1317-1324, American Society for Microbiology (1998).
Mygind, P.H., et al., "Membrane proteins PmpG and PmpH are major constituents of *Chlamydia trachomatis* L2 outer membrane complex," *FEMS Microbiol. Lett. 186*:163169, Elsevier Science B.V. (May 2000).
Nosoh, Y. and Sekiguchi, T., eds., *Protein Stability and Stabilization through Protein Engineering*, Prentice Hall Professional Technical Reference, East Rutherford, NJ, pp. 197 (1991).
Ortiz, L., et al., "T-Cell Epitopes in Variable Segments of *Chlamydia trachomatis* Major Outer Membrane Protein Elicit Serovar-Specific Immune Responses in Infected Humans," *Infect. Immun. 68*:1719-1723, American Society for Microbiology (Mar. 2000).
Samukawa, T., et al., "Immune Response to Surface Protein A of *Streptococcus pneumoniae* and to High-Molecular-Weight Outer Membrane Protein A of *Moraxella catarrhalis* in Children with Acute Otitis Media," *J. Infect. Dis. 181*:1842-1845, University of Chicago Press (May 2000).

Schmitt, J., et al., "Affinity Purification of Histidine-Tagged Proteins," *Mol. Biol. Rep. 18*:223-230, Reidel (1993).

Stephens, R.S., et al., "Genome Sequence of an Obligate Intracellular Pathogen of Humans: *Chlaymdia trachomatis," Science 282*:754-759, American Association for the Advancement of Science (1998).

Stothard, D.R., et al., "Polymorphic Membrane H Has Evolved in Parallel with the Three Disease-Causing Groups of *Chlamydia trachomatis," Infect. Immun. 71*:1200-1208, American Society for Microbiology (Mar. 2003).

Su, H., et al., "Identification and Characterization of T Helper Cell Epitopes of the Major Outer Membrane Protein of *Chlamydia trachomatis," J. Exp. Med. 172*:203-212, Rockefeller University Press (1990).

Su, H., et al., "Immunogenicity of a Chimeric Peptide Corresponding to T Helper and B Cell Epitopes of the *Chlamydia trachomatis* Major Outer Membrane Protein," *J. Exp. Med. 175*:227-235, Rockefeller University Press (1992).

Tanzer, R.J., and Hatch, T.P., "Characterization of Outer Membrane Proteins in *Chlamydia trachomatis* LGV Serovar L2," *J. Bacteriol. 183*:2686-2690, American Society for Microbiology (Apr. 2001).

Longbottom, D., "Chlamydial vaccine development," *J. Med. Microbiol. 52*:537-540, Lippincott Williams and Wilkins (Jul. 2003).

Nosoh, Y. and Sekiguchi, T., eds., *Protein Stability and Stabilization through Protein Engineering*, Prentice Hall Professional Technical Reference, East Rutherford, NJ, pp. 197-217 (1991).

International Search Report for International Application No. PCT/US01/30345, United States Patent and Trademark Office, Alexandria, VA, mailed on Feb. 20, 2003.

Supplemental Partial European Search Report for International Application No. EP 01 97 5515, European Patent Office, Munich, Germany, search completed on Apr. 21, 2005.

Supplementary Partial European Search Report for International Application No. EP 01 97 5515, European Patent Office, Munich, Germany, search completed on Sep. 5, 2005.

Partial European Search Report for International Application No. EP 07 00 7316, European Patent Office, Munich, Germany, search completed on Jul. 5, 2007.

* cited by examiner

```
atg aaa aaa gcg ttt ttc ttt ttc ctt att gga aac tcc cta tca gga      48
Met Lys Lys Ala Phe Phe Phe Phe Leu Ile Gly Asn Ser Leu Ser Gly
 1               5                  10                  15

cta gct aga gag gtt cct tct aga atc ttt ctt atg ccc aac tca gtt      96
Leu Ala Arg Glu Val Pro Ser Arg Ile Phe Leu Met Pro Asn Ser Val
            20                  25                  30

cca gat cct acg aaa gag tcg cta tca aat aaa att agt ttg aca gga     144
Pro Asp Pro Thr Lys Glu Ser Leu Ser Asn Lys Ile Ser Leu Thr Gly
        35                  40                  45

gac act cac aat ctc act aac tgc tat ctc gat aac cta cgc tac ata     192
Asp Thr His Asn Leu Thr Asn Cys Tyr Leu Asp Asn Leu Arg Tyr Ile
    50                  55                  60

ctg gct att cta caa aaa act ccc aat gaa gga gct gct gtc aca ata     240
Leu Ala Ile Leu Gln Lys Thr Pro Asn Glu Gly Ala Ala Val Thr Ile
65                  70                  75                  80

aca gat tac cta agc ttt ttt gat aca caa aaa gaa ggt att tat ttt     288
Thr Asp Tyr Leu Ser Phe Phe Asp Thr Gln Lys Glu Gly Ile Tyr Phe
                85                  90                  95

gca aaa aat ctc acc cct gaa agt ggt ggt gcg att ggt tat gcg agt     336
Ala Lys Asn Leu Thr Pro Glu Ser Gly Gly Ala Ile Gly Tyr Ala Ser
            100                 105                 110

ccc aat tct cct acc gtg gag att cgt gat aca ata ggt cct gta atc     384
Pro Asn Ser Pro Thr Val Glu Ile Arg Asp Thr Ile Gly Pro Val Ile
        115                 120                 125

ttt gaa aat aat act tgt tgc aga cca ttt aca tcg agt aat cct aat     432
Phe Glu Asn Asn Thr Cys Cys Arg Pro Phe Thr Ser Ser Asn Pro Asn
    130                 135                 140

gca gct gtt aat aaa ata aga gaa ggc gga gcc att cat gct caa aat     480
Ala Ala Val Asn Lys Ile Arg Glu Gly Gly Ala Ile His Ala Gln Asn
145                 150                 155                 160

ctt tac ata aat cat aat cat gat gtg gtc gga ttt atg aag aac ttt     528
Leu Tyr Ile Asn His Asn His Asp Val Val Gly Phe Met Lys Asn Phe
                165                 170                 175

tct tat gtc cga gga gga gcc att agt acc gct aat acc ttt gtt gtg     576
Ser Tyr Val Arg Gly Gly Ala Ile Ser Thr Ala Asn Thr Phe Val Val
            180                 185                 190

agc gag aat cag tct tgt ttt ctc ttt atg gac aac atc tgt att caa     624
Ser Glu Asn Gln Ser Cys Phe Leu Phe Met Asp Asn Ile Cys Ile Gln
        195                 200                 205

act aat aca gca gga aaa ggt ggc gct atc tat gct gga acg agc aat     672
Thr Asn Thr Ala Gly Lys Gly Gly Ala Ile Tyr Ala Gly Thr Ser Asn
    210                 215                 220
```

FIG. 5A

```
tct ttt gag agt aat aac tgc gat ctc ttc ttt atc aat aac gcc tgt      720
Ser Phe Glu Ser Asn Asn Cys Asp Leu Phe Phe Ile Asn Asn Ala Cys
225                 230                 235                 240

tgt gca gga gga gcg atc ttc tcc cct atc tgt tct cta aca gga aat      768
Cys Ala Gly Gly Ala Ile Phe Ser Pro Ile Cys Ser Leu Thr Gly Asn
            245                 250                 255

cgt ggt aac atc gtt ttc tat aac aat cgc tgc ttt aaa aat gta gaa      816
Arg Gly Asn Ile Val Phe Tyr Asn Asn Arg Cys Phe Lys Asn Val Glu
        260                 265                 270

aca gct tct tca gaa gct tct gat gga gga gca att aaa gta act act      864
Thr Ala Ser Ser Glu Ala Ser Asp Gly Gly Ala Ile Lys Val Thr Thr
    275                 280                 285

cgc cta gat gtt aca ggc aat cgt ggt agg atc ttt ttt agt gac aat      912
Arg Leu Asp Val Thr Gly Asn Arg Gly Arg Ile Phe Phe Ser Asp Asn
    290                 295                 300

atc aca aaa aat tat ggc gga gct att tac gct cct gta gtt acc cta      960
Ile Thr Lys Asn Tyr Gly Gly Ala Ile Tyr Ala Pro Val Val Thr Leu
305                 310                 315                 320

gtg gat aat ggc cct acc tac ttt ata aac aat atc gcc aat aat aag     1008
Val Asp Asn Gly Pro Thr Tyr Phe Ile Asn Asn Ile Ala Asn Asn Lys
                325                 330                 335

ggg ggc gct atc tat ata gac gga acc agc aac tcc aaa att tct gcc     1056
Gly Gly Ala Ile Tyr Ile Asp Gly Thr Ser Asn Ser Lys Ile Ser Ala
            340                 345                 350

gac cgc cat gct att att ttt aat gaa aat att gtg act aat gta act     1104
Asp Arg His Ala Ile Ile Phe Asn Glu Asn Ile Val Thr Asn Val Thr
        355                 360                 365

aat gca aat ggt acc agt acg tca gct aat cct cct aga aga aat gca     1152
Asn Ala Asn Gly Thr Ser Thr Ser Ala Asn Pro Pro Arg Arg Asn Ala
    370                 375                 380

ata aca gta gca agc tcc tct ggt gaa att cta tta gga gca ggg agt     1200
Ale Thr Val Ala Ser Ser Ser Gly Glu Ile Leu Leu Gly Ala Gly Ser
385                 390                 395                 400

agc caa aat tta att ttt tat gat cct att gaa gtt agc aat gca ggg     1248
Ser Gln Asn Leu Ile Phe Tyr Asp Pro Ile Glu Val Ser Asn Ala Gly
                405                 410                 415

gtc tct gtg tcc ttc aat aag gaa gct gat caa aca ggc tct gta gta     1296
Val Ser Val Ser Phe Asn Lys Glu Ala Asp Gln Thr Gly Ser Val Val
            420                 425                 430

ttt tca gga gct act gtt aat tct gca gat ttt cat caa cgc aat tta     1344
Phe Ser Gly Ala Thr Val Asn Ser Ala Asp Phe His Gln Arg Asn Leu
        435                 440                 445
```

FIG. 5B

```
caa aca aaa aca cct gca ccc ctt act ctc agt aat ggt ttt cta tgt     1392
Gln Thr Lys Thr Pro Ala Pro Leu Thr Leu Ser Asn Gly Phe Leu Cys
    450                 455                 460

atc gaa gat cat gct cag ctt aca gtg aat cga ttc aca caa act ggg     1440
Ile Glu Asp His Ala Gln Leu Thr Val Asn Arg Phe Thr Gln Thr Gly
465                 470                 475                 480

ggt gtt gtt tct ctt ggg aat gga gca gtt ctg agt tgc tat aaa aat     1488
Gly Val Val Ser Leu Gly Asn Gly Ala Val Leu Ser Cys Tyr Lys Asn
                485                 490                 495

ggt gca gga aat tct gct agc aat gcc tct ata aca ctg aag cat att     1536
Gly Ala Gly Asn Ser Ala Ser Asn Ala Ser Ile Thr Leu Lys His Ile
            500                 505                 510

gga ttg aat ctt tct tcc att ctg aaa agt ggt gct gag att cct tta     1584
Gly Leu Asn Leu Ser Ser Ile Leu Lys Ser Gly Ala Glu Ile Pro Leu
        515                 520                 525

ttg tgg gta gag cct aca aat aac agc aat aac tat aca gca gat act     1632
Leu Trp Val Glu Pro Thr Asn Asn Ser Asn Asn Tyr Thr Ala Asp Thr
    530                 535                 540

gca gct acc ttt tca tta agt gat gta aaa ctc tca ctc att gat gac     1680
Ala Ala Thr Phe Ser Leu Ser Asp Val Lys Leu Ser Leu Ile Asp Asp
545                 550                 555                 560

tat ggg aat tct cct tat gaa tcc aca gat cta acc cat gct ctg tca     1728
Tyr Gly Asn Ser Pro Tyr Glu Ser Thr Asp Leu Thr His Ala Leu Ser
                565                 570                 575

tca cag cct atg cta tct att tct gag gct agt gat aac cag cta aga     1776
Ser Gln Pro Met Leu Ser Ile Ser Glu Ala Ser Asp Asn Gln Leu Arg
            580                 585                 590

tct gat gat atg gat ttt tcg gga cta aat gtc cct cat tat gga tgg     1824
Ser Asp Asp Met Asp Phe Ser Gly Leu Asn Val Pro His Tyr Gly Trp
        595                 600                 605

caa gga ctt tgg act tgg ggc tgg gca aaa act caa gat cca gaa cca     1872
Gln Gly Leu Trp Thr Trp Gly Trp Ala Lys Thr Gln Asp Pro Glu Pro
    610                 615                 620

gca tct tca gca aca atc aca gat cca caa aaa gcc aat aga ttc cat     1920
Ala Ser Ser Ala Thr Ile Thr Asp Pro Gln Lys Ala Asn Arg Phe His
625                 630                 635                 640

aga acc tta tta ctg act tgg ctt cct gct ggg tat gtt cct agc ccg     1968
Arg Thr Leu Leu Leu Thr Trp Leu Pro Ala Gly Tyr Val Pro Ser Pro
                645                 650                 655

aaa cac aga agt ccc ctc ata gcg aat acc tta tgg ggg aat atg ctg     2016
Lys His Arg Ser Pro Leu Ile Ala Asn Thr Leu Trp Gly Asn Met Leu
            660                 665                 670
```

FIG. 5C

```
ctt gca aca gaa agc tta aaa aat agt gca gaa ctg aca cct agt gat      2064
Leu Ala Thr Glu Ser Leu Lys Asn Ser Ala Glu Leu Thr Pro Ser Asp
        675                 680                 685

cat cct ttc tgg gga att aca gga gga gga cta ggc atg atg gtt tac      2112
His Pro Phe Trp Gly Ile Thr Gly Gly Gly Leu Gly Met Met Val Tyr
    690                 695                 700

caa gat cct cga gaa aat cat cct gga ttc cat atg cgc tct tcc gga      2160
Gln Asp Pro Arg Glu Asn His Pro Gly Phe His Met Arg Ser Ser Gly
705                 710                 715                 720

tac tct gcg ggg atg ata gca ggg cag aca cac acc ttc tca ttg aaa      2208
Tyr Ser Ala Gly Met Ile Ala Gly Gln Thr His Thr Phe Ser Leu Lys
                725                 730                 735

ttc agt cag acc tac acc aaa ctc aat gag cgt tac gca aaa aac aac      2256
Phe Ser Gln Thr Tyr Thr Lys Leu Asn Glu Arg Tyr Ala Lys Asn Asn
            740                 745                 750

gta tct tct aaa aat tac tca tgc caa gga gaa atg ctc ttc tca ttg      2304
Val Ser Ser Lys Asn Tyr Ser Cys Gln Gly Glu Met Leu Phe Ser Leu
        755                 760                 765

caa gaa ggt ttc ttg ctg act aaa tta gtt ggg ctt tac agc tat gga      2352
Gln Glu Gly Phe Leu Leu Thr Lys Leu Val Gly Leu Tyr Ser Tyr Gly
    770                 775                 780

gac cat aac tgt cac cat ttc tat acc caa gga gaa aat cta aca tct      2400
Asp His Asn Cys His His Phe Tyr Thr Gln Gly Glu Asn Leu Thr Ser
785                 790                 795                 800

caa ggg acg ttc cgt agt caa acg atg gga ggt gct gtt ttt ttt gat      2448
Gln Gly Thr Phe Arg Ser Gln Thr Met Gly Gly Ala Val Phe Phe Asp
                805                 810                 815

ctc cct atg aaa ccc ttt gga tca acg cat ata ctg aca gct ccc ttt      2496
Leu Pro Met Lys Pro Phe Gly Ser Thr His Ile Leu Thr Ala Pro Phe
            820                 825                 830

tta ggt gct ctt ggt att tat tct agc ctg tct cac ttt act gag gtg      2544
Leu Gly Ala Leu Gly Ile Tyr Ser Ser Leu Ser His Phe Thr Glu Val
        835                 840                 845

gga gcc tat ccg cga agc ttt tct aca aag act cct ttg atc aat gtc      2592
Gly Ala Tyr Pro Arg Ser Phe Ser Thr Lys Thr Pro Leu Ile Asn Val
    850                 855                 860

cta gtc cct att gga gtt aaa ggt agc ttt atg aat gct acc caa aga      2640
Leu Val Pro Ile Gly Val Lys Gly Ser Phe Met Asn Ala Thr Gln Arg
865                 870                 875                 880

cct caa gcc tgg act gta gaa ttg gca tac caa ccc gtt ctg tat aga      2688
Pro Gln Ala Trp Thr Val Glu Leu Ala Tyr Gln Pro Val Leu Tyr Arg
                885                 890                 895
```

FIG. 5D

```
caa gaa cca ggg atc gcg acc cag ctc cta gcc agt aag ggt att tgg      2736
Gln Glu Pro Gly Ile Ala Thr Gln Leu Leu Ala Ser Lys Gly Ile Trp
            900                 905                 910

ttt ggt agt gga agc ccc tca tcg cgt cat gcc atg tcc tat aaa atc      2784
Phe Gly Ser Gly Ser Pro Ser Ser Arg His Ala Met Ser Tyr Lys Ile
        915                 920                 925

tca cag caa aca caa cct ttg agt tgg tta act ctc cat ttc cag tat      2832
Ser Gln Gln Thr Gln Pro Leu Ser Trp Leu Thr Leu His Phe Gln Tyr
    930                 935                 940

cat gga ttc tac tcc tct tca acc ttc tgt aat tat ctc aat ggg gaa      2880
His Gly Phe Tyr Ser Ser Ser Thr Phe Cys Asn Tyr Leu Asn Gly Glu
945                 950                 955                 960

att gct ctg cga ttc tag                                              2898
Ile Ala Leu Arg Phe
                965
```

FIG. 5E

```
atg cga cct gat cat atg aac ttc tgt tgt cta tgt gct gct att ttg      48
Met Arg Pro Asp His Met Asn Phe Cys Cys Leu Cys Ala Ala Ile Leu
 1               5                  10                  15

tca tcc aca gcg gtc ctc ttt ggc cag gat ccc tta ggt gaa acc gcc      96
Ser Ser Thr Ala Val Leu Phe Gly Gln Asp Pro Leu Gly Glu Thr Ala
            20                  25                  30

ctc ctc act aaa aat cct aat cat gtc gtc tgt aca ttt ttt gag gac     144
Leu Leu Thr Lys Asn Pro Asn His Val Val Cys Thr Phe Phe Glu Asp
        35                  40                  45

tgt acc atg gag agc ctc ttt cct gct ctt tgt gct cat gca tca caa     192
Cys Thr Met Glu Ser Leu Phe Pro Ala Leu Cys Ala His Ala Ser Gln
    50                  55                  60

gac gat cct ttg tat gta ctt gga aat tcc tac tgt tgg ttc gta tct     240
Asp Asp Pro Leu Tyr Val Leu Gly Asn Ser Tyr Cys Trp Phe Val Ser
65                  70                  75                  80

aaa ctc cat atc acg gac ccc aaa gag gct ctt ttt aaa gaa aaa gga     288
Lys Leu His Ile Thr Asp Pro Lys Glu Ala Leu Phe Lys Glu Lys Gly
                85                  90                  95

gat ctt tcc att caa aac ttt cgc ttc ctt tcc ttc aca gat tgc tct     336
Asp Leu Ser Ile Gln Asn Phe Arg Phe Leu Ser Phe Thr Asp Cys Ser
            100                 105                 110

tcc aag gaa agc tct cct tct att att cat caa aag aat ggt cag tta     384
Ser Lys Glu Ser Ser Pro Ser Ile Ile His Gln Lys Asn Gly Gln Leu
        115                 120                 125

tcc ttg cgc aat aat ggt agc atg agt ttc tgt cga aat cat gct gaa     432
Ser Leu Arg Asn Asn Gly Ser Met Ser Phe Cys Arg Asn His Ala Glu
    130                 135                 140

ggc tct gga gga gcc atc tct gcg gat gcc ttt tct cta cag cac aac     480
Gly Ser Gly Gly Ala Ile Ser Ala Asp Ala Phe Ser Leu Gln His Asn
145                 150                 155                 160

tat ctt ttc aca gct ttt gaa gag aat tct tct aaa gga aat ggc gga     528
Tyr Leu Phe Thr Ala Phe Glu Glu Asn Ser Ser Lys Gly Asn Gly Gly
                165                 170                 175

gcc att cag gct caa acc ttc tct tta tct aga aat gtg tcg cct att     576
Ala Ile Gln Ala Gln Thr Phe Ser Leu Ser Arg Asn Val Ser Pro Ile
            180                 185                 190

tct ttc gcc cgt aat cgt gcg gat tta aat ggc ggc gct att tgc tgt     624
Ser Phe Ala Arg Asn Arg Ala Asp Leu Asn Gly Gly Ala Ile Cys Cys
        195                 200                 205

agt aat ctt att tgt tca ggg aat gta aac cct ctc ttt ttc act gga     672
Ser Asn Leu Ile Cys Ser Gly Asn Val Asn Pro Leu Phe Phe Thr Gly
    210                 215                 220
```

FIG. 6A

```
aac tcc gcc acg aat gga ggc gct att tgt tgt atc agc gat cta aac      720
Asn Ser Ala Thr Asn Gly Gly Ala Ile Cys Cys Ile Ser Asp Leu Asn
225                 230                 235                 240

acc tca gaa aaa ggc tct ctc tct ctt gct tgt aac caa gaa acg cta      768
Thr Ser Glu Lys Gly Ser Leu Ser Leu Ala Cys Asn Gln Glu Thr Leu
                245                 250                 255

ttt gca agc aat tct gct aaa gaa aaa ggc ggg gct att tat gcc aag      816
Phe Ala Ser Asn Ser Ala Lys Glu Lys Gly Gly Ala Ile Tyr Ala Lys
            260                 265                 270

cac atg gta ttg cgt tat aac ggt cct gtt tcc ttc att aac aac agc      864
His Met Val Leu Arg Tyr Asn Gly Pro Val Ser Phe Ile Asn Asn Ser
        275                 280                 285

gct aaa ata ggt gga gct atc gcc atc cag tcc gga ggg agt ctc tct      912
Ala Lys Ile Gly Gly Ala Ile Ala Ile Gln Ser Gly Gly Ser Leu Ser
    290                 295                 300

atc ctt gca ggt gaa gga tct gtt ctg ttc cag aat aac tcc caa cgc      960
Ile Leu Ala Gly Glu Gly Ser Val Leu Phe Gln Asn Asn Ser Gln Arg
305                 310                 315                 320

acc tcc gac caa ggt cta gta aga aac gcc atc tac tta gag aaa gat     1008
Thr Ser Asp Gln Gly Leu Val Arg Asn Ala Ile Tyr Leu Glu Lys Asp
                325                 330                 335

gcg att ctt tct tcc tta gaa gct cgc aac gga gat att ctt ttc ttt     1056
Ala Ile Leu Ser Ser Leu Glu Ala Arg Asn Gly Asp Ile Leu Phe Phe
            340                 345                 350

gat cct att gta caa gaa agt agc agc aaa gaa tcg cct ctt ccc tcc     1104
Asp Pro Ile Val Gln Glu Ser Ser Ser Lys Glu Ser Pro Leu Pro Ser
        355                 360                 365

tct ttg caa gcc agc gtg act tct ccc acc cca gcc acc gca tct cct     1152
Ser Leu Gln Ala Ser Val Thr Ser Pro Thr Pro Ala Thr Ala Ser Pro
    370                 375                 380

tta gtt att cag aca agt gca aac cgt tca gtg att ttc tcg agc gaa     1200
Leu Val Ile Gln Thr Ser Ala Asn Arg Ser Val Ile Phe Ser Ser Glu
385                 390                 395                 400

cgt ctt tct gaa gaa gaa aaa act cct gat aac ctc act tcc caa cta     1248
Arg Leu Ser Glu Glu Glu Lys Thr Pro Asp Asn Leu Thr Ser Gln Leu
                405                 410                 415

cag cag cct atc gaa ctg aaa tcc gga cgc tta gtt tta aaa gat cgc     1296
Gln Gln Pro Ile Glu Leu Lys Ser Gly Arg Leu Val Leu Lys Asp Arg
            420                 425                 430

gct gtc ctt tcc gcg cct tct ctc tct cag gat cct caa gct ctc ctc     1344
Ala Val Leu Ser Ala Pro Ser Leu Ser Gln Asp Pro Gln Ala Leu Leu
        435                 440                 445
```

FIG. 6B

```
att atg gaa gcg gga act tct tta aaa act tcc tct gat ttg aag tta      1392
Ile Met Glu Ala Gly Thr Ser Leu Lys Thr Ser Ser Asp Leu Lys Leu
    450                 455                 460

gct acg cta agt att ccc ctt cat tcc tta gat act gaa aaa agc gta      1440
Ala Thr Leu Ser Ile Pro Leu His Ser Leu Asp Thr Glu Lys Ser Val
465                 470                 475                 480

act atc cac gcc cct aac ctt tct atc caa aag atc ttc ctc tct aat      1488
Thr Ile His Ala Pro Asn Leu Ser Ile Gln Lys Ile Phe Leu Ser Asn
                485                 490                 495

tct gga gat gag aat ttt tat gaa aat gta gag ctt ctc agt aaa gag      1536
Ser Gly Asp Glu Asn Phe Tyr Glu Asn Val Glu Leu Leu Ser Lys Glu
            500                 505                 510

caa aac aat att cct ctc ctt act ctc tct aaa gag caa tct cat tta      1584
Gln Asn Asn Ile Pro Leu Leu Thr Leu Ser Lys Glu Gln Ser His Leu
        515                 520                 525

cat ctt cct gat ggg aac ctc tct tct cac ttt gga tat caa gga gat      1632
His Leu Pro Asp Gly Asn Leu Ser Ser His Phe Gly Tyr Gln Gly Asp
    530                 535                 540

tgg act ttt tct tgg aaa gat tct gat gaa ggg cat tct ctg att gct      1680
Trp Thr Phe Ser Trp Lys Asp Ser Asp Glu Gly His Ser Leu Ile Ala
545                 550                 555                 560

aat tgg acg cct aaa aac tat gtg cct cat cca gaa cgt caa tct aca      1728
Asn Trp Thr Pro Lys Asn Tyr Val Pro His Pro Gln Arg Gln Ser Thr
                565                 570                 575

ctc gtt gcg aac act ctt tgg aac acc tat tcc gat atg caa gct gtg      1776
Leu Val Ala Asn Thr Leu Trp Asn Thr Tyr Ser Asp Met Gln Ala Val
            580                 585                 590

cag tcg atg att aat aca ata gcg cac gga gga gcc tat cta ttt gga      1824
Gln Ser Met Ile Asn Thr Ile Ala His Gly Gly Ala Tyr Leu Phe Gly
        595                 600                 605

acg tgg gga tct gct gtt tct aat tta ttc tat gct cac gac agc tct      1872
Thr Trp Gly Ser Ala Val Ser Asn Leu Phe Tyr Ala His Asp Ser Ser
    610                 615                 620

ggg aaa cct atc gat aat tgg cat cat aga agc ctt ggc tac cta ttc      1920
Gly Lys Pro Ile Asp Asn Trp His His Arg Ser Leu Gly Tyr Leu Phe
625                 630                 635                 640

ggt atc agt act cac agt tta gat gac cat tct ttc tgc ttg gct gca      1968
Gly Ile Ser Thr His Ser Leu Asp Asp His Ser Phe Cys Leu Ala Ala
                645                 650                 655

gga caa tta ctc ggg aaa tcg tcc gat tcc ttt att acg tct aca gaa      2016
Gly Gln Leu Leu Gly Lys Ser Ser Asp Ser Phe Ile Thr Ser Thr Glu
            660                 665                 670
```

FIG. 6C

```
acg acc tcc tat ata gct act gta caa gcg caa ctc gct acc tct cta      2064
Thr Thr Ser Tyr Ile Ala Thr Val Gln Ala Gln Leu Ala Thr Ser Leu
        675                 680                 685

atg aaa atc tct gca cag gca tgc tac aat gaa agt atc cat gag cta      2112
Met Lys Ile Ser Ala Gln Ala Cys Tyr Asn Glu Ser Ile His Glu Leu
    690                 695                 700

aaa aca aaa tat cgc tcc ttc tct aaa gaa gga ttc gga tcc tgg cat      2160
Lys Thr Lys Tyr Arg Ser Phe Ser Lys Glu Gly Phe Gly Ser Trp His
705                 710                 715                 720

agc gtt gca gta tcc gga gaa gtg tgc gca tcg att cct att gta tcc      2208
Ser Val Ala Val Ser Gly Glu Val Cys Ala Ser Ile Pro Ile Val Ser
                725                 730                 735

aat ggt tcc gga ctg ttc agc tcc ttc tct att ttc tct aaa ctg caa      2256
Asn Gly Ser Gly Leu Phe Ser Ser Phe Ser Ile Phe Ser Lys Leu Gln
            740                 745                 750

gga ttt tca gga aca cag gac ggt ttt gag gag agt tcg gga gag att      2304
Gly Phe Ser Gly Thr Gln Asp Gly Phe Glu Glu Ser Ser Gly Glu Ile
        755                 760                 765

cgg tcc ttt tct gcc agc tct ttc aga aat att tca ctt cct ata gga      2352
Arg Ser Phe Ser Ala Ser Ser Phe Arg Asn Ile Ser Leu Pro Ile Gly
    770                 775                 780

ata aca ttt gaa aaa aaa tcc caa aaa aca cga acc tac tat tac ttt      2400
Ile Thr Phe Glu Lys Lys Ser Gln Lys Thr Arg Thr Tyr Tyr Tyr Phe
785                 790                 795                 800

cta gga gcc tac atc caa gac ctg aaa cgt gat gtg gaa tcg gga cct      2448
Leu Gly Ala Tyr Ile Gln Asp Leu Lys Arg Asp Val Glu Ser Gly Pro
                805                 810                 815

gta gtg tta ctc aaa aat gcc gtc tcc tgg gat gct cct atg gcg aac      2496
Val Val Leu Leu Lys Asn Ala Val Ser Trp Asp Ala Pro Met Ala Asn
            820                 825                 830

ttg gat tca cga gcc tac atg ttc agg ctt acg aat caa aga gct cta      2544
Leu Asp Ser Arg Ala Tyr Met Phe Arg Leu Thr Asn Gln Arg Ala Leu
        835                 840                 845

cac aga ctt cag acg ctg tta aat gtg tct tgt gtg ctg cgt ggg caa      2592
His Arg Leu Gln Thr Leu Leu Asn Val Ser Cys Val Leu Arg Gly Gln
    850                 855                 860

agc cat agt tac tcc ctg gat ctg ggg acc act tac agg ttc              2634
Ser His Ser Tyr Ser Leu Asp Leu Gly Thr Thr Tyr Arg Phe
865                 870                 875

tag                                                                  2637
```

FIG. 6D

```
atg aga gga tcg cat cac cat cac cat cac gga tcc gca tgc gag ctc      48
Met Arg Gly Ser His His His His His His Gly Ser Ala Cys Glu Leu
1               5                   10                  15

ggt acc ccg ggt cga cgg gtt cca gat cct acg aaa gag tcg cta tca      96
Gly Thr Pro Gly Arg Arg Val Pro Asp Pro Thr Lys Glu Ser Leu Ser
            20                  25                  30

aat aaa att agt ttg aca gga gac act cac aat ctc act aac tgc tat     144
Asn Lys Ile Ser Leu Thr Gly Asp Thr His Asn Leu Thr Asn Cys Tyr
        35                  40                  45

ctc gat aac cta cgc tac ata ctg gct att cta caa aaa act ccc aat     192
Leu Asp Asn Leu Arg Tyr Ile Leu Ala Ile Leu Gln Lys Thr Pro Asn
    50                  55                  60

gaa gga gct gct gtc aca ata aca gat tac cta agc ttt ttt gat aca     240
Glu Gly Ala Ala Val Thr Ile Thr Asp Tyr Leu Ser Phe Phe Asp Thr
65                  70                  75                  80

caa aaa gaa ggt att tat ttt gca aaa aat ctc acc cct gaa agt ggt     288
Gln Lys Glu Gly Ile Tyr Phe Ala Lys Asn Leu Thr Pro Glu Ser Gly
                85                  90                  95

ggt gcg att ggt tat gcg agt ccc aat tct cct acc gtg gag att cgt     336
Gly Ala Ile Gly Tyr Ala Ser Pro Asn Ser Pro Thr Val Glu Ile Arg
            100                 105                 110

gat aca ata ggt cct gta atc ttt gaa aat aat act tgt tgc aga cca     384
Asp Thr Ile Gly Pro Val Ile Phe Glu Asn Asn Thr Cys Cys Arg Pro
        115                 120                 125

ttt aca tcg agt aat cct aat gca gct gtt aat aaa ata aga gaa ggc     432
Phe Thr Ser Ser Asn Pro Asn Ala Ala Val Asn Lys Ile Arg Glu Gly
    130                 135                 140

gga gcc att cat gct caa aat ctt tac ata aat cac aat cat gat gtg     480
Gly Ala Ile His Ala Gln Asn Leu Tyr Ile Asn His Asn His Asp Val
145                 150                 155                 160

gtc gga ttt atg aag aac ttt tct tat gtc cga gga gga gcc att agt     528
Val Gly Phe Met Lys Asn Phe Ser Tyr Val Arg Gly Gly Ala Ile Ser
                165                 170                 175

acc gct aat acc ttt gtt gtg agc gag aat cag tct tgt ttt ctc ttt     576
Thr Ala Asn Thr Phe Val Val Ser Glu Asn Gln Ser Cys Phe Leu Phe
            180                 185                 190

atg gac aac atc tgt att caa act aat aca gca gga aaa ggt ggc gct     624
Met Asp Asn Ile Cys Ile Gln Thr Asn Thr Ala Gly Lys Gly Gly Ala
        195                 200                 205

atc tat gct gga acg agc aat tct ttt gag agt aat aac tgc gat ctc     672
Ile Tyr Ala Gly Thr Ser Asn Ser Phe Glu Ser Asn Asn Cys Asp Leu
    210                 215                 220

ttc ttt atc aat aac gcc tgt tgt gca gga gga gcg atc ttc tcc cct     720
Phe Phe Ile Asn Asn Ala Cys Cys Ala Gly Gly Ala Ile Phe Ser Pro
225                 230                 235                 240

atc tgt tct cta aca gga aat cgt ggt aac atc gtt ttc tat aac aat     768
```

FIG. 8A

```
Ile Cys Ser Leu Thr Gly Asn Arg Gly Asn Ile Val Phe Tyr Asn Asn
                245                 250                 255

cgc tgc ttt aaa aat gta gaa aca gct tct tca gaa gct tct gat gga      816
Arg Cys Phe Lys Asn Val Glu Thr Ala Ser Ser Glu Ala Ser Asp Gly
            260                 265                 270

gga gca att aaa gta act act cgc cta gat gtt aca ggc aat cgt ggt      864
Gly Ala Ile Lys Val Thr Thr Arg Leu Asp Val Thr Gly Asn Arg Gly
        275                 280                 285

agg atc ttt ttt agt gac aat atc aca aaa aat tat ggc gga gct att      912
Arg Ile Phe Phe Ser Asp Asn Ile Thr Lys Asn Tyr Gly Gly Ala Ile
    290                 295                 300

tac gct cct gta gtt acc cta gtg gat aat ggc cct acc tac ttt ata      960
Tyr Ala Pro Val Val Thr Leu Val Asp Asn Gly Pro Thr Tyr Phe Ile
305                 310                 315                 320

aac aat gtc gcc aat aat aag ggg ggc gct atc tat ata gac gga acc     1008
Asn Asn Val Ala Asn Asn Lys Gly Gly Ala Ile Tyr Ile Asp Gly Thr
                325                 330                 335

agc aac tcc aaa att tct gcc gac cgc cat gct att att ttt aat gaa     1056
Ser Asn Ser Lys Ile Ser Ala Asp Arg His Ala Ile Ile Phe Asn Glu
            340                 345                 350

aat att gtg act aat gta act agt gca aat ggt acc agt acg tca gct     1104
Asn Ile Val Thr Asn Val Thr Ser Ala Asn Gly Thr Ser Thr Ser Ala
        355                 360                 365

aat cct cct aga aga aat gca ata aca gta gca agc tcc tct ggt gaa     1152
Asn Pro Pro Arg Arg Asn Ala Ile Thr Val Ala Ser Ser Ser Gly Glu
    370                 375                 380

att cta tta gga gca ggg agt agc caa aat tta att ttt tat gat cct     1200
Ile Leu Leu Gly Ala Gly Ser Ser Gln Asn Leu Ile Phe Tyr Asp Pro
385                 390                 395                 400

att gaa gtt agc aat gca ggg gtc tct gtg tcc ttc aat aag gaa gct     1248
Ile Glu Val Ser Asn Ala Gly Val Ser Val Ser Phe Asn Lys Glu Ala
                405                 410                 415

gat caa aca ggc tct gta gta ttt tca gga gct act gtt aat tct gca     1296
Asp Gln Thr Gly Ser Val Val Phe Ser Gly Ala Thr Val Asn Ser Ala
            420                 425                 430

gat ttt cat caa cgc aat tta caa aca aaa aca cct gca ccc ctt act     1344
Asp Phe His Gln Arg Asn Leu Gln Thr Lys Thr Pro Ala Pro Leu Thr
        435                 440                 445

ctc agt aat ggt ttt cta tgt atc gaa gat cat gct cag ctt aca gtg     1392
Leu Ser Asn Gly Phe Leu Cys Ile Glu Asp His Ala Gln Leu Thr Val
    450                 455                 460

aat cga ttc aca caa act ggg ggt gtt gtt tct ctt ggg aat gga gca     1440
Asn Arg Phe Thr Gln Thr Gly Gly Val Val Ser Leu Gly Asn Gly Ala
465                 470                 475                 480

gtt ctg agt tgc tat aaa aat ggt gca gga aat tct gct agc aat gcc     1488
Val Leu Ser Cys Tyr Lys Asn Gly Ala Gly Asn Ser Ala Ser Asn Ala
```

FIG. 8B

```
                485                     490                     495

tct ata aca ctg aag cat att gga ttg aat ctt tct tcc att ctg aaa      1536
Ser Ile Thr Leu Lys His Ile Gly Leu Asn Leu Ser Ser Ile Leu Lys
            500                     505                     510

agt ggt gct gag att cct tta ttg tgg gta gag cct aca aat aac agc      1584
Ser Gly Ala Glu Ile Pro Leu Leu Trp Val Glu Pro Thr Asn Asn Ser
        515                     520                     525

aat aac tat aca gca gat act gca gct acc ttt tca tta agt gat gta      1632
Asn Asn Tyr Thr Ala Asp Thr Ala Ala Thr Phe Ser Leu Ser Asp Val
    530                     535                     540

aaa ctc tca ctc att gat gac tat ggg aat tct cct tat gaa tcc aca      1680
Lys Leu Ser Leu Ile Asp Asp Tyr Gly Asn Ser Pro Tyr Glu Ser Thr
545                     550                     555                     560

gat cta acc cat gct ctg tca tca cag cct atg cta tct att tct gag      1728
Asp Leu Thr His Ala Leu Ser Ser Gln Pro Met Leu Ser Ile Ser Glu
                565                     570                     575

gct agt gat aac cag cta aga tct gat gat atg gat ttc tcg gga cta      1776
Ala Ser Asp Asn Gln Leu Arg Ser Asp Asp Met Asp Phe Ser Gly Leu
            580                     585                     590

aat gtc cct cat tat gga tgg caa gga ctt tgg agt tgg ggc tgg gca      1824
Asn Val Pro His Tyr Gly Trp Gln Gly Leu Trp Ser Trp Gly Trp Ala
        595                     600                     605

aaa act caa gat cca gaa cca gca tct tca gca aca atc aca gat ccc      1872
Lys Thr Gln Asp Pro Glu Pro Ala Ser Ser Ala Thr Ile Thr Asp Pro
    610                     615                     620

aaa aaa gcc aat aga ttc cat aga acc tta tta ctg act tgg ctt cct      1920
Lys Lys Ala Asn Arg Phe His Arg Thr Leu Leu Leu Thr Trp Leu Pro
625                     630                     635                     640

gct ggg tat gtt cct agc ccg aaa cac aga agt ccc ctc ata gcg aat      1968
Ala Gly Tyr Val Pro Ser Pro Lys His Arg Ser Pro Leu Ile Ala Asn
                645                     650                     655

acc tta tgg ggg aat atg ctg ctt gca aca gaa agc tta aaa aat agt      2016
Thr Leu Trp Gly Asn Met Leu Leu Ala Thr Glu Ser Leu Lys Asn Ser
            660                     665                     670

gca gaa ctg aca cct agt gat cat cct ttc tgg gga att aca gga gga      2064
Ala Glu Leu Thr Pro Ser Asp His Pro Phe Trp Gly Ile Thr Gly Gly
        675                     680                     685

gga cta ggc atg atg gtt tac caa gaa cct cga gaa aat cat cct gga      2112
Gly Leu Gly Met Met Val Tyr Gln Glu Pro Arg Glu Asn His Pro Gly
    690                     695                     700

ttc cat atg cgc tct tcc gga tac ttt gcg ggg atg ata gca ggg caa      2160
Phe His Met Arg Ser Ser Gly Tyr Phe Ala Gly Met Ile Ala Gly Gln
705                     710                     715                     720

aca cat acc ttc tca ttg aaa ttc agt cag acc tac acc aaa ctc aat      2208
Thr His Thr Phe Ser Leu Lys Phe Ser Gln Thr Tyr Thr Lys Leu Asn
                725                     730                     735
```

FIG. 8C

```
gag cgt tac gca aaa aac aac gta tct tct aaa aat tac tca tgc caa      2256
Glu Arg Tyr Ala Lys Asn Asn Val Ser Ser Lys Asn Tyr Ser Cys Gln
            740                 745                 750

gga gaa atg ctc ttc tca ttg caa gaa ggt ttc ttg ctg gct aaa tta      2304
Gly Glu Met Leu Phe Ser Leu Gln Glu Gly Phe Leu Leu Ala Lys Leu
        755                 760                 765

gtt ggt ctt tac agc tat gga gat cat aac tgt cac cat ttc tat acc      2352
Val Gly Leu Tyr Ser Tyr Gly Asp His Asn Cys His His Phe Tyr Thr
    770                 775                 780

caa gga gaa aat cta aca tct caa ggg acg ttc cgt agt caa acg atg      2400
Gln Gly Glu Asn Leu Thr Ser Gln Gly Thr Phe Arg Ser Gln Thr Met
785                 790                 795                 800

gga ggt gct gtt ttt ttt gat ctc cct atg aaa ccc ttt gga tca acg      2448
Gly Gly Ala Val Phe Phe Asp Leu Pro Met Lys Pro Phe Gly Ser Thr
                805                 810                 815

cat ata ctg aca gct ccc ttt tta ggt gct ctt ggt att tat tct agc      2496
His Ile Leu Thr Ala Pro Phe Leu Gly Ala Leu Gly Ile Tyr Ser Ser
            820                 825                 830

ctg tct cac ttt act gag gtg gga gcc tat ccg cga agc ttt tct aca      2544
Leu Ser His Phe Thr Glu Val Gly Ala Tyr Pro Arg Ser Phe Ser Thr
        835                 840                 845

aag act cct ttg atc aat gtc cta gtc cct att gga gtt aaa ggt agc      2592
Lys Thr Pro Leu Ile Asn Val Leu Val Pro Ile Gly Val Lys Gly Ser
    850                 855                 860

ttt atg aat gct acc caa aga cct caa gcc tgg act gta gaa ttg gca      2640
Phe Met Asn Ala Thr Gln Arg Pro Gln Ala Trp Thr Val Glu Leu Ala
865                 870                 875                 880

tac caa ccc gtt ctg tat aga caa gaa cta gag atc gcg acc cag ctc      2688
Tyr Gln Pro Val Leu Tyr Arg Gln Glu Leu Glu Ile Ala Thr Gln Leu
                885                 890                 895

cta gcc agt aaa ggt att tgg ttt ggt agt gga agc ccc tca tcg cgt      2736
Leu Ala Ser Lys Gly Ile Trp Phe Gly Ser Gly Ser Pro Ser Ser Arg
            900                 905                 910

cat gcc atg tcc tat aaa atc tca cag caa aca caa cct ttg agt tgg      2784
His Ala Met Ser Tyr Lys Ile Ser Gln Gln Thr Gln Pro Leu Ser Trp
        915                 920                 925

tta act ctc cat ttc cag tat cat gga ttc tac tcc tct tca acc ttc      2832
Leu Thr Leu His Phe Gln Tyr His Gly Phe Tyr Ser Ser Ser Thr Phe
    930                 935                 940

tgt aat tat ctc aat ggg gaa att gct ctg cga ttc taa                  2871
Cys Asn Tyr Leu Asn Gly Glu Ile Ala Leu Arg Phe
945                 950                 955
```

FIG. 8D

*CHLAMYDIA* PMP PROTEINS, GENE SEQUENCES AND USES THEREOF

CROSS-REFERENCE TO RELATED APPLICATIONS

The present application is a divisional application of U.S. application Ser. No. 10/398,248, which is a national stage application of International Application No. PCT/U01/30345, filed on Sep. 28, 2001, which is a continuation-in-part of U.S. application Ser. No. 09/677,752, filed Oct. 2, 2000, which is hereby incorporated by reference in its their entireties.

1. FIELD OF THE INVENTION

The present invention generally relates to polymorphic membrane proteins or PMPs of *Chlamydia*, amino acid and nucleotide sequences thereof, antibodies specific for such *Chlamydia* PMP polypeptides, prophylactic and therapeutic compositions, including vaccines, and to methods of preventing, treating or ameliorating disorders in mammals and birds related to *Chlamydia* infections and for inducing immune responses in animals to *Chlamydia*.

2. BACKGROUND OF THE INVENTION

Chlamydiae are obligate intracellular bacteria that infect animals, including mammals and birds, particularly at the epithelial lining of the lung, conjunctivae or genital tract. The most common species of *Chlamydia* include *Chlamydia trachomatis, Chlamydia psittaci, Chlamydia pecorum* and *Chlamydia pneumoniae*. Recently, the newly designated species of *Chlamydia, C. pneumoniae* (formerly *C. trachomatis* TWAR), has been implicated as a major cause of epidemic human pneumonitis and perhaps may play a role in atherosclerosis.

There are currently 18 recognized *C. trachomatis* serovars, causing trachoma and a broad spectrum of sexually transmitted diseases, with the A, B and C serovars being most frequently associated with trachoma, while the D-K serovars are the most common cause of genital infections.

*Chlamydia* are prevalent human pathogens causing disorders such as sexually transmitted diseases, respiratory diseases, including pneumonia, neonatal conjunctivitis, and blindness. Reactive inflammatory arthritis is a common sequel to sexually acquired non-gonococcal genital tract infection. Approximately 50% of reactive inflammatory arthritis cases are associated with *Chlamydia trachomatis* infection of the genital tract.

*C. trachomatis* is the major cause of sexually transmitted disease in many industrialized countries, including the United States. While the exact incidence of *C. trachomatis* infection in the United States is not known, current epidemiological studies indicate that more than 4 million chlamydial infections occur each year, compared to an estimated 2 million gonococcal infections. While all racial, ethnic and socioeconomic groups are affected, the greatest number of chlamydial infections occurs among young, 12 to 20 year-old, sexually active individuals. Most genitourinary chlamydial infections are clinically asymptomatic. Prolonged carriage in both men and women is common. As many as 25% of men and 75% of women diagnosed as having chlamydial infections have no overt signs of infection. As a consequence, these asymptomatic individuals constitute a large reservoir that can sustain transmission of the agent within the community.

Far from being benign, serious disease can develop from these infections including: urethritis, lymphogranuloma venereum (LGV), cervicitis, and epididymitis in males. Ascending infections from the endocervix commonly gives rise to endometritis, pelvic inflammatory disease (PID) and salpingitis which can cause tubal occlusion and lead ultimately to infertility in females. Recently, *Chlamydia* infections have been linked to heart disease (Bachaier et al. Science:283:1335, 1999; Fan et al. Inf. and Imm. 67:6145, 1999).

*C. trachomatis* infection of neonates results from perinatal exposure to the mother's infected cervix. Nearly 70% of neonates born vaginally to mothers with chlamydial cervicitis become infected during delivery. The mucus membranes of the eye, oropharynx, urogenital tract and rectum are the primary sites of infection. Chlamydial conjunctivitis has become the most common form of ophthalmia neonatorum. Approximately 20-30% of exposed infants develop inclusion conjunctivitis within 14 days of delivery even after receiving prophylaxis with either silver nitrate or antibiotic ointment. *C. trachomatis* is also the leading cause of infant pneumonia in the United States. Nearly 10-20% of neonates delivered through an infected cervix will develop chlamydial pneumonia and require some type of medical intervention.

In developing countries, ocular infections of *C. trachomatis* cause trachoma, a chronic follicular conjunctivitis where repeated scar formation leads to distortion of the eyelids and eventual loss of sight. Trachoma is the world's leading cause of preventable blindness. The World Health Organization estimates that over 500 million people worldwide, including about 150 million children, currently suffer from active trachoma and over 6 million people have been blinded by this disease.

In industrialized countries, the costs associated with treating chlamydial infections are enormous. In the United States, the annual cost of treating these diseases was estimated at $2.5-3 billion in 1992 and has been projected to exceed $8 billion by the year 2000.

One potential solution to this health crisis would be an effective chlamydial vaccine. Several lines of evidence suggest that developing an effective vaccine is feasible.

Studies in both humans and primates have shown that short-term protective immunity to *C. trachomatis* can be produced by vaccinating with whole *Chlamydia*. However, protection was characterized as short lived, serovar specific, and due to mucosal antibody production. Additionally, in some vaccinees disease was exacerbated when these individuals became naturally infected with a serovar different from that used for immunization. This adverse reaction was ultimately demonstrated to be due to a delayed-type hypersensitivity response. Thus, the need exists to develop a subunit-based chlamydial vaccine capable of producing an efficacious but nonsensitizing immune response. Such a subunit vaccine may need to elicit both mucosal neutralizing secretory IgA antibody and/or cellular immune response to be efficacious.

Subunit vaccine development efforts to date have focused almost exclusively on the major outer membrane protein (MOMP). MOMP is an integral membrane protein of approximately 40 kDa in size and comprises up to about 60% of the infectious elementary body (EB) membrane protein (Caldwell et al. 1981. *Infect. Immun.,* 31:1161-1176). MOMP imparts structural integrity to the extracellular EB and is thought to function as a porin-like molecule when the organism is growing intracellularly and is metabolically active. With the exception of four surface exposed variable domains (VDI-VDIV), MOMP is highly conserved among all 18 serovars. MOMP is highly immunogenic and can elicit a local neutralizing anti-*Chlamydia* antibody. However, problems exists with this approach.

To date, most MOMP-specific neutralizing epitopes that have been mapped are located within the VD regions and thus give rise only to serovar-specific antibody. Attempts to combine serovar-specific epitopes in various vaccine vectors (e.g., poliovirus) to generate broadly cross-reactive neutralizing antibodies have been only marginally successful (Murdin et al. 1993. *Infect. Immun.,* 61:4406-4414; Murdin et al. 1995. *Infect. Immun.,* 63:1116-1121).

Two other major outer membrane proteins in *C. trachomatis*, the 60 kDa and 12 kDa cysteine-rich proteins, as well as the surface-exposed lipopolysaccharide, are highly immunogenic but, unlike MOMP, have not been shown to induce a neutralizing antibody (Cerrone et al., 1991, *Infect Immun.,* 59:79-90). Therefore, there remains a need for a novel subunit-based chlamydial vaccine.

Citation or identification of any reference in this section or any other section of this application shall not be construed as an indication that such reference is available as prior art to the present invention.

3. SUMMARY OF THE INVENTION

This invention is directed to PMP proteins (referred to hereafter and in the claims as PMP polypeptides or PMP proteins) from *Chlamydia* spp. More particularly, the present invention encompasses the family of PMPE and PMPI polypeptides of *Chlamydia trachomatis* and other *Chlamydia* spp., including but not limited to, *Chlamydia pneumonia, Chlamydia pecorum*, and *Chlamydia psittaci*, having a molecular weight of 90 to 115 kD, and an amino acid sequence of SEQ ID NO:2 or 73 (PMPE) or SEQ ID NO.:4 (PMPI) or a sequence homologous thereto, in isolated, purified or recombinantly produced form. SEQ ID NOs.:2 and 4 represent the amino acid sequences of the *Chlamydia trachomatis* L2 serovar PMPE and PMPI proteins, respectively, encoded by the pmpE and pmpI genes. SEQ ID NO:73 represents the amino acid sequence of the *Chlamydia trachomatis* L2 serovar PMPE protein encoded by plasmid M15 pREP (pQE-PmpE-Ct#37), which is derived from a different strain than is SEQ ID NO:2. Preferably, the PMPE and PMPI polypeptides of the invention are encoded by a nucleic acid comprising a nucleotide sequence that hybridizes under low, moderate or, more preferably, highly stringent conditions to a nucleic acid comprising a nucleotide sequence encoding the amino acid sequence of SEQ ID NO:2, 4, or 73 or a nucleotide sequence of SEQ ID NO.:1,3, or 73. Also, preferably, the PMPE and PMPI polypeptides of the invention do not cross react with or bind specifically to the monoclonal antibody secreted by hybridoma ATCC No. HB10861 available from the American Type Tissue Collection (ATCC).

The nucleotide sequences for the pmpE and pmpI *Chlamydia trachomatis* L2 serovar coding regions are SEQ ID NOs.:1 and 3, respectively. The nucleotide sequence of the portion of plasmid M15 pREP (pQE-PmpE-Ct#37) encoding the PMPE polypeptide also of the *Chlamydia trachomatis* L2 serovar is SEQ ID NO:72. The present invention encompasses all *Chlamydia* PMPE and PMPI polypeptides, particularly those of the *Chlamydia trachomatis* L2 serovar, and also including PMPI and PMPE polypeptides from other *Chlamydia trachomatis* serovars and other *Chlamydia* species. Identification of these homologs can be accomplished by methods well known in the art, for example, but not limited to, nucleic acid hybridization and PCR based techniques. The present invention encompasses isolated and/or purified PMPE and PMPI polypeptides, and polypeptides derived therefrom ("PMP-derived polypeptides", e.g., derivatives, fragments and analogs thereof), preferably, that elicit an immune reaction against whole *Chlamydia* cells and/or are specifically bound by antibodies raised against polypeptides having an amino acid sequence of SEQ ID NO.: 2, 4, or 73. The invention further comprises methods for making said PMP polypeptides and PMP-derived polypeptides.

Preferably, the PMP protein has the amino acid sequence of SEQ ID NO.:2, 4 or 73 or is homologous to any of SEQ ID NO.:2, 4-34, or 73, preferably having an amino acid sequence identity of at least 70% or 80%, more preferably greater than 90%, and most preferably greater than 95% or 99%. These proteins preferably elicit an immune reaction against whole *Chlamydia* cells and/or are specifically bound by antibodies raised against polypeptides having an amino acid sequence of SEQ ID NO.: 2, 4, or 73. Preferred fragments of the protein comprise an amino acid sequence of any of SEQ ID NOs.:5-34.

Preferably, the PMP protein is an outer membrane protein. More preferably, the PMP protein is surface localized. Preferably, the PMP protein has at least one GGAI (Gly Gly Ala Ile) domain. It is intended that PMP proteins from all species of *Chlamydia* are included in this invention; however, preferred species include *Chlamydia trachomatis, Chlamydia psittaci, Chlamydia pecorum* and *Chlamydia pneumoniae.*

The invention also provides PMP fusion peptides having B and/or T-cell stimulating activity, preferably comprising at least two T or B cell epitopes derived from the same or from different *Chlamydia* PMP proteins which proteins, or portions thereof, are arranged in a contiguous polypeptide in a configuration different from a naturally occurring configuration of the regions of a *Chlamydia* PMP protein.

A preferred polypeptide of the invention is a fusion polypeptide comprising at least two peptides, said at least two peptides, each consisting of amino acid sequences selected from the group consisting of SEQ ID NOs.:5, 6, 7, 8, 9, 10, 11, 12, 13, 14, 15, 16, 17, 18, 19, 20, 21, 22, 23, 24, 25, 26, 27, 28, 29, 30, 31, 32, 33, and 34, with the proviso that the peptides of the polypeptide are arranged in a contiguous polypeptide configuration that is different from the configuration of a naturally occurring PMPE or PMPI polypeptide (e.g., is not a naturally occurring PMPE or PMPI polypeptide or fragment thereof).

Other preferred PMP-derived polypeptides of the invention are isolated or purified fusion polypeptides wherein the polypeptide comprises one or more of the amino acid sequences of SEQ ID NO.:5, 6, 7, 8, 9, 10 or 11 or an isolated or purified fusion polypeptide wherein the polypeptide comprises an amino acid sequence of SEQ ID NO.:23, 24, 25, 26, 27, 28, or 29, with the proviso that the peptides of the polypeptide are arranged in a configuration that is different from the configuration of a naturally occurring PMPE or PMPI polypeptide. A preferred PMP-derived polypeptide is an isolated or purified fusion polypeptide, wherein the polypeptide comprises an amino acid sequence of SEQ ID NO.:5, 6, 7, 8, 9, 10, 11, 23, 24, 25, 26, 27, 28 or 29, with the proviso that the peptides are arranged in a configuration that is different from the configuration of a naturally occurring PMPE or PMPI polypeptide.

Preferably, the PMP-derived polypeptides of the invention are immunologically cross-reactive with the PMP protein from which they are derived and are capable of eliciting in an animal an immune response to *Chlamydia*. A preferred PMP polypeptide or PMP-derived polypeptide of the invention induces IgM, IgG, IgA, and/or IgE antibodies, delayed hypersensitivity T-cell responses and/or cytotoxic T-cell responses to cells expressing Chlamydial antigens (including but not limited to cells infected with *Chlamydia* and antigen presenting cells such as macrophages, dendritic cells, B cells, or synthetic antigen presenting cells which display Chlamydial antigens), native PMP proteins from which the polypeptide is derived, *Chlamydia* cells, or *Chlamydia* elemental bodies (EB). In a more preferred embodiment, the PMP polypeptide or PMP-derived polypeptide is capable of eliciting an immune response against other *Chlamydia* serovars and, more preferably, other *Chlamydia* species along with the *Chlamydia* serovar or species in which the PMP polypeptide occurs naturally.

The invention also encompasses antisera and antibodies, including but not limited to, cytotoxic or bactericidal polyclonal and monoclonal antibodies, which bind to and are specific for the PMP polypeptide, PMP-derived polypeptides and/or fragments thereof.

Preferably the antibodies bind a PMP protein (preferably a PMPE or PMPI polypeptide) having the amino acid sequence of SEQ ID NOs.:2, 73, or 4 or an amino acid sequence homologous thereto. Also included are monoclonal antibodies that specifically bind a PMP or PMP-derived polypeptide, including but not limited to monoclonal antibodies that specifically bind a polypeptide comprising an amino acid sequence of any of SEQ ID NOs.:2, 4-34 or 73. Also included are antigen binding fragments of polyclonal or monoclonal antibodies, e.g., Fv, Fab, Fab' and $F(ab')_2$ fragments. A further aspect of the invention are chimerized or humanized antibodies in which one or more of the antigen binding regions of the anti-PMP antibody is introduced into the framework region of a heterologous (e.g., human) antibody. In a preferred aspect, the antibodies are human antibodies.

Another aspect of the invention is directed to T-cells raised against an antigenic or immunogenic composition of the invention or T-cells specific for antigenic or immunogenic polypeptides of the invention or specific for cells expressing Chlamydial antigens (including but not limited to cells infected with *Chlamydia* or antigen presenting cells presenting PMP polypeptides such as dendritic cells, B cells, or synthetic antigen presenting cells), *Chlamydia* cells, or *Chlamydia* elemental bodies (EB).

The invention further provides isolated nucleic acid molecules (DNA or RNA) encoding the PMPE polypeptides, PMPI polypeptides, PMPE-derived polypeptides, PMPI-derived polypeptides, vectors comprising said sequences, host cells containing said vectors or having the sequences operably linked to a heterologous promoter, recombinant polypeptides produced therefrom, and pharmaceutical compositions comprising the nucleic acid molecules, vectors, and cells.

A preferred aspect of the invention is a nucleotide sequence encoding a PMP protein comprising the amino acid sequence of any of SEQ ID NOs.:2, 4-34, or 73 or an amino acid sequence substantially homologous thereto. Also included is an isolated nucleic acid molecule comprising a DNA sequence of SEQ ID NOs.:1, 3 or 72 or a complementary sequence thereof; a fragment of the DNA molecule having the nucleotide sequence of SEQ ID NOs.:1, 3 or 72, or a complementary sequence thereof; or a nucleic acid molecule which hybridizes under low or moderate stringency conditions or, more preferably, highly stringent (or stringent) conditions to any one of the sequences described above. The nucleic acid molecule that hybridizes under stringent conditions preferably has a sequence identity of about 70%, 80%, 90%, 95%, or 99% with any of the sequences identified above, more preferably about 90%.

The invention further encompasses pharmaceutical compositions including prophylactic or therapeutic compositions, which may be immunogenic compositions, including vaccines, comprising one or more of the PMP polypeptides of the invention, optionally in combination with, fused to, or conjugated to one or more other component(s), including a lipid, phospholipid, a carbohydrate, including a lipopolysaccharide, any proteins either novel or known to those skilled in the art, inactivated whole or attenuated organisms, including but not limited to viruses, yeasts, fungi and bacteria. Particularly preferred bacteria include, but are not limited to *Neisseria, Chlamydia, Moraxella, Pseudomonas, Streptococcus* or *Haemophilus* bacteria.

In a specific embodiment, the invention encompasses pharmaceutical compositions, including prophylactic or therapeutic compositions, which may be immunogenic compositions including vaccines, comprising one or more of the PMP polypeptides and/or PMP-derived polypeptides and an attenuated or inactivated *Chlamydia* cultivar or an attenuated or inactivated *Chlamydia* cultivar expressing PMP polypeptide in a greater amount when compared to wild-type *Chlamydia.*

The invention further encompasses pharmaceutical compositions comprising isolated nucleic acid molecules encoding PMP polypeptides and PMP-derived polypeptides of the present invention which can be used in methods to detect *Chlamydia* infection or to prevent, treat or reduce the severity of a disease or disorder related to infection with *Chlamydia*. Such compositions include but are not limited to vectors or recombinant host cells comprising such nucleic acid molecules or having a nucleotide sequence of the invention operably linked to a heterologous promoter.

The invention also includes diagnostic reagents, that may include any one or more of the above mentioned aspects, such as native PMP proteins, recombinant PMP proteins, PMP-derived polypeptides, nucleic acid molecules, immunogenic compositions, antigenic compositions, antisera, T-cells, antibodies, vectors comprising the nucleic acids, and transformed cells comprising the vectors.

A further aspect of the present invention provides methods for determining the presence of nucleic acids encoding a PMP protein or a PMP-derived polypeptide in a test sample, and diagnostic kits and reagents therefor, for determining the presence of a nucleic acid encoding a PMP polypeptide or PMP-derived polypeptide.

Also included in this invention are methods of inducing an immune response to *Chlamydia* spp. and methods of preventing, treating or ameliorating disorders or diseases related to *Chlamydia* in an animal, including mammals and birds and, preferably, in humans, in need of such treatment comprising administering an effective amount of the pharmaceutical or vaccine composition of the invention. Preferred disorders or diseases include a *Chlamydia* bacterial infection, including those infections that cause trachoma, conjunctivitis, urethritis, lymphogranuloma venereum (LGV), cervicitis, epididymitis, or endometritis, pelvic inflammatory disease (PID), salpingitis, tubal occlusion, infertility, cervical cancer, reactive arthritis, inflammatory heart disease, dilated/cardiomyopathy, autoimmune myocarditis, or atherosclerosis.

A further aspect of the invention provides antagonists or agonists which inhibit or enhance, respectively, the activity or expression of the polypeptides or nucleic acid molecules of the invention. In particular embodiments, the agonists or antagonists kill *Chlamydia* cells or arrest *Chlamydia* cell growth, i.e., can be used to treat or prevent *Chlamydia* infection.

A further aspect of the invention is a method for identifying compounds which interact with and inhibit or activate an activity of the polypeptides or nucleic acid molecules of the invention comprising contacting a composition comprising the polypeptide or the nucleic acid molecule with the compound to be screened under conditions that permit interaction between the compound and the polypeptide or nucleic acid molecule to assess the interaction of a compound and to detect interaction of the compound with the polypeptide of nucleic acid. The interaction of the compound with the polypeptide or nucleic acid molecule is determined by the association of a second component (e.g., an antibody) capable of providing a detectable signal in response to the interaction of the polypeptide or nucleic acid molecule with the compound; and determining the presence or absence of a signal generated from the interaction of the compound with the polypeptide or nucleic acid molecule. Alternatively, the interaction of the compound with the polypeptide or nucleic acid molecule is determined by the ability of the compound to inhibit the activity of the polypeptide or the nucleic acid molecule.

3.1. Abbreviations anti-PMP=PMP polypeptide antibody or antiserum
ATCC=American Type Culture Collection
immuno-reactive=capable of provoking a cellular or humoral immune response
kD or kDa=kilodaltons
OG=n-octyl-D-glucopyranoside or octyl glucoside
OMP=outer membrane protein
OMPs=outer membrane proteins
PBS=phosphate buffered saline
PAGE=polyactylamide gel electrophoresis
polypeptide=a peptide of any length, preferably having eight or more amino acid residues
SDS=sodium dodecylsulfate
SDS-PAGE=sodium dodecylsulfate polyacrylamide gel electrophoresis Nucleotide sequences defined herein are represented by one-letter symbols for the bases as follows:

A (adenine)
C (cytosine)
G (guanine)
T (thymine)
U (uracil)
M (A or C)
R (A or G)
W (A or T/U)
S (C or G)
Y (C or T/U)
K (G or T/U)
V (A or C or G; not T/U)
H (A or C or T/U; not G)
D (A or G or T/U; not C)
B (C or G or T/U; not A)
N (A or C or G or T/U) or (unknown)

Peptide and polypeptide sequences defined herein are represented by one-letter symbols for amino acid residues as follows:

A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)
S (serine)
T (threonine)
W (tryptophan)
Y (tyrosine)
V (valine)
X (unknown)

The present invention may be more fully understood by reference to the following detailed description of the invention, non-limiting examples of specific embodiments of the invention and the appended figures.

4. BRIEF DESCRIPTION OF DRAWINGS

FIG. 1. Schematic map of the *C. trachomatis* PMPE expression plasmid M15 pREP (pQE-PmpE-Ct#37). The mature form of the *C. trachomatis* PMPE protein is expressed in *E. coli* as a fusion protein carrying the MRGS-$(H)_6$ domain encoded by the vector plasmid pQE-30 at the N-terminus.

Figure 2:
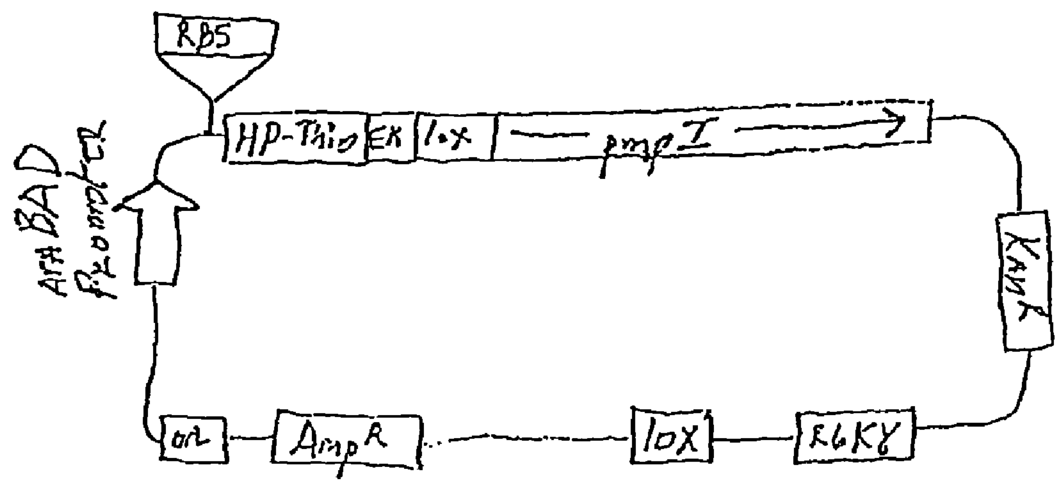

FIG. 2. Schematic map of the *C. trachomatis* PMPI expression plasmid TOP10 (pBAD-pmpI-Ct-Uni#7). The *C. trachomatis* PMPI protein is expressed in *E. coli* as a fusion protein carrying the HP-Thio domain encoded by the vector plasmid pBAD/Thio-E at the N-terminus.

Figure 3:
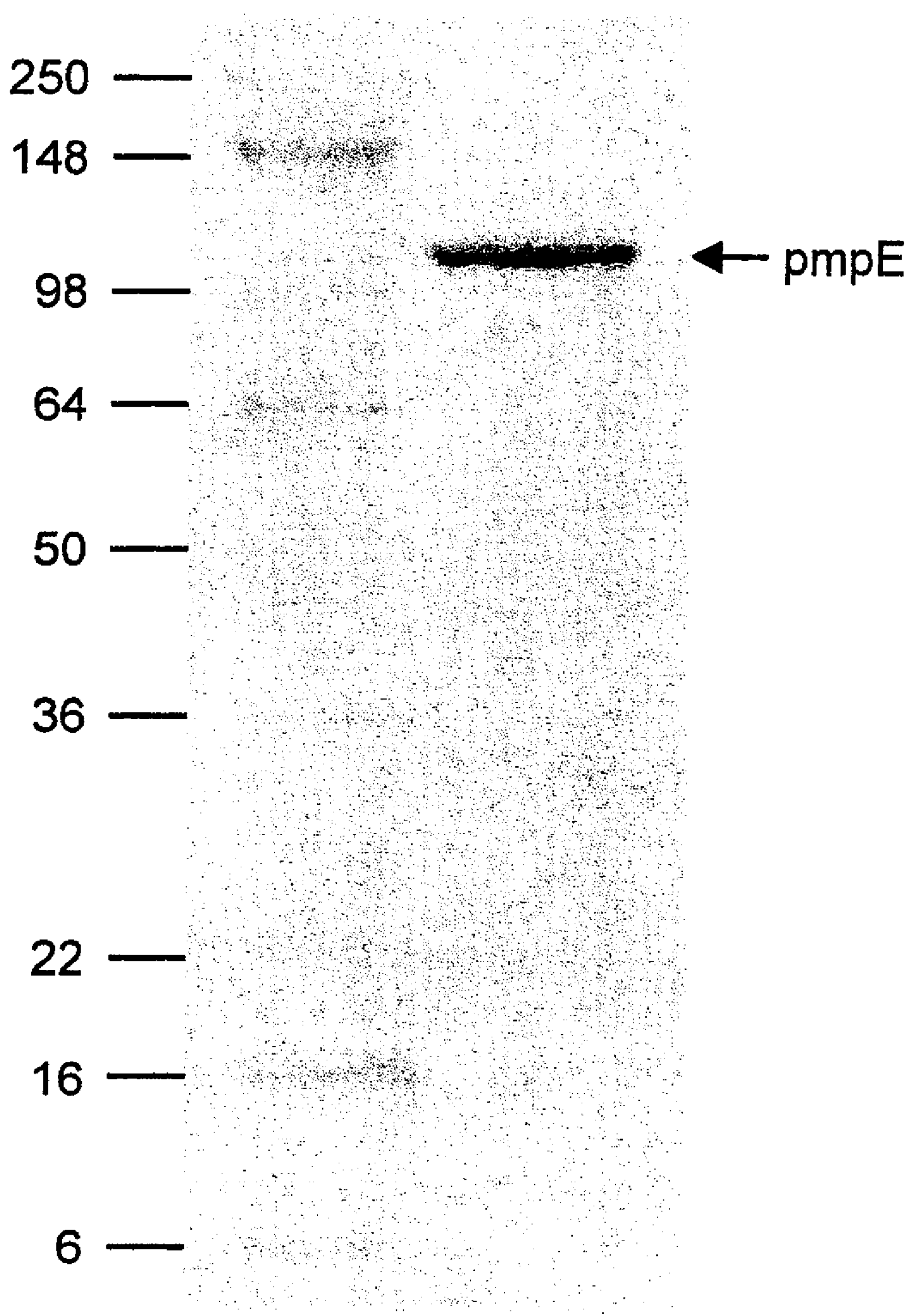

FIG. 3. A Coomassie blue-stained SDS-PAGE gel of the gel-purified *C. trachomatis* PMPE protein expressed from the pQE-pmpE-Ct #37 plasmid. The PMPE protein migrates as an ~100 kDa protein. Pre-stained molecular weight markers (Lane 1) are Myosin (~250 kDa), Phosphorylase B (~148 kDa), BSA (~98 kDa), GDH (~64 kDa), ADH (~50 kDa), CAH (~36 kDa), Myoglobulin (30 kDa), Lysozyme (16 kDa), Aprotinin (~6 kDa), Insulin B chain (~4 kDa) (See Blue prestained standard Novex LC5625).

Figure 4:
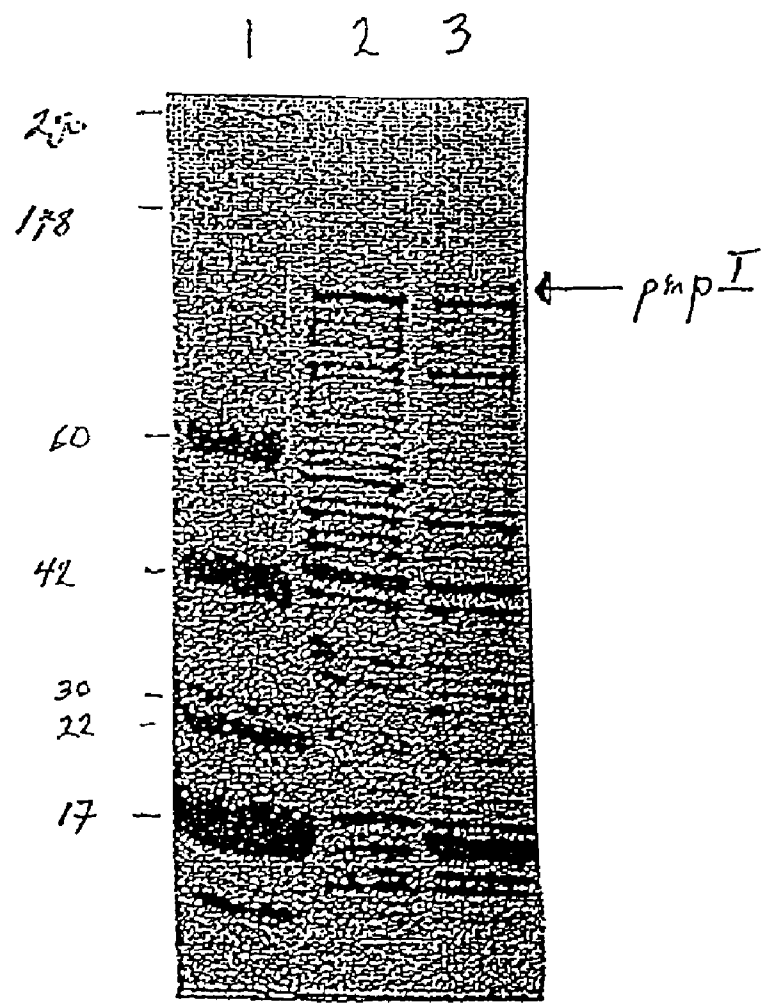

FIG. 4. A Coomassie blue-stained SDS-PAGE gel of *E. coli* Top10 cell extracts carrying the *C. trachomatis* PMPI expression plasmid pBAD-pmpI-ct-Uni#7. Lane 1, pre-stained molecular weight markers (Novex MultiMark LC5725); lane 2, non-induced cells; lane 3, arabinose induced cells. The *C. trachomatis* PMPI protein in the arabinose-induced lane is indicated by an arrow. Molecular weight markers (Lane 1) are Myosin (~250 kDa), Phosphorylase B (~148 kDa), GDH (~60 kDa), CAH (~42 kDa), Myoglobulin-Blue (~30 kDa), Myoglobulin-Red (~22 kDa), Lysozyme (~17 kDa).

FIGS. 5A-E. Full length nucleotide sequence and corresponding deduced amino acid sequence of the PMPE polypeptide of *Chlamydia trachomatis* L2 (SEQ ID NOs.:1 and 2).

FIGS. 6A-D. Full length nucleotide sequence and corresponding deduced amino acid sequence of the PMPI polypeptide of *Chlamydia trachomatis* L2 (SEQ ID NOs.:3 and 4).

Figure 7:
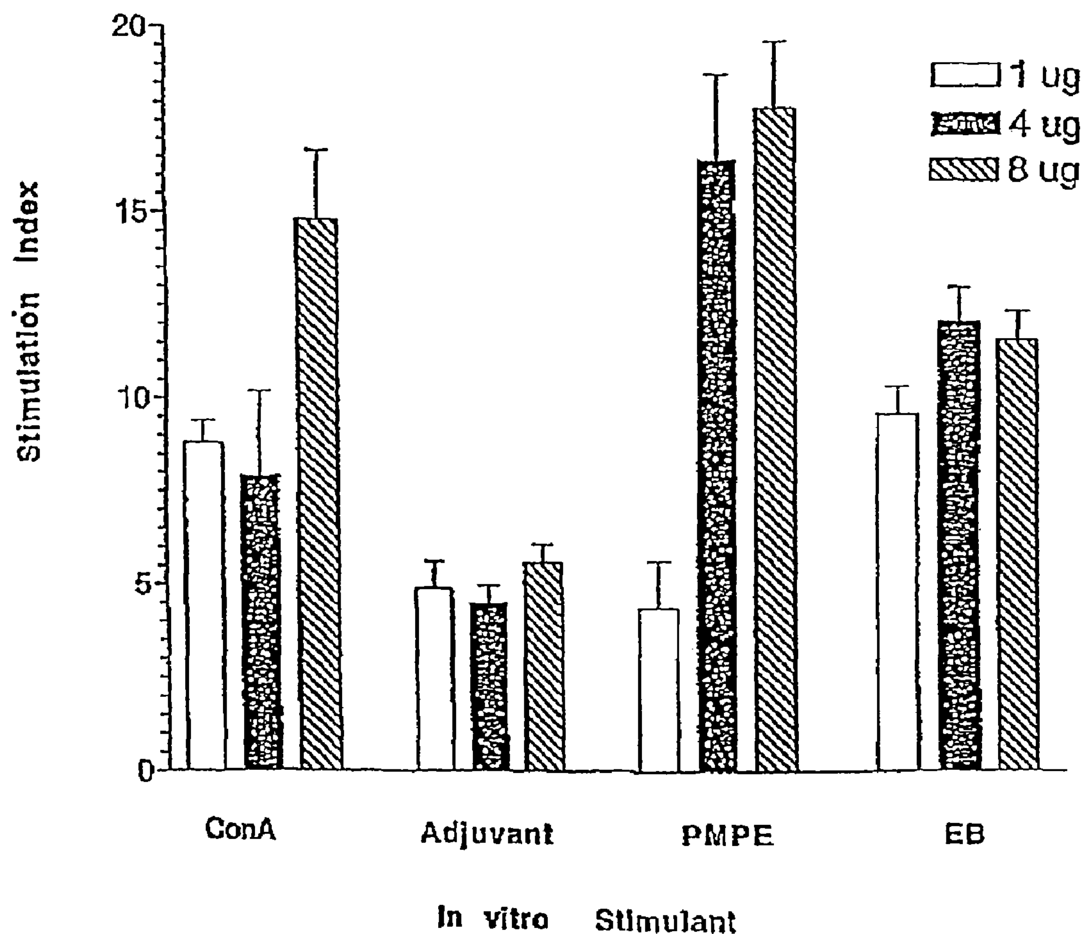

FIG. 7. In vitro antigen-specific spleen cell proliferative response in animals immunized with recombinant PMPE and an adjuvant. Spleens were harvested from immunized C3H HeOuJ female mice approximately 14 days after a three dose immunization regimen. Single cell suspensions were prepared and the cells from two animals were pooled for analysis. Aliquots of the pooled cell samples were incubated for 72-96 hours in the presence of a test stimulant and pulsed with $^3$H-thymidine for the last 18-24 hours. Pooled samples incubated and pulsed labeled in parallel but in the absence of any stimulant served as the baseline $^3$H-thymidine uptake control. Represented is the stimulation index of cells stimulated with ConA (concanavalin A) (positive stimulation control); adjuvant (adjuvant employed in immunizations); PMPE (recombinant pmpE protein); EB (UV-inactivated *C. trachomatis* elementary bodies). 1 μg/ml (open bars), 4 μg/ml (solid bars) and 8 μg/ml (hatched bars) denote the three concentrations of in vitro stimulant used in the experiment. Stimulation index (SI) denotes the difference in $^{3}$H-thymidine incorporation of stimulated cells minus the background incorporation of the unstimulated controls. Bars denote the mean±standard deviation in SI.

FIGS. 8A-D. Full length nucleotide and corresponding deduced amino acid sequence of the PMPE polypeptide of *Chlamydia trachomatis* serovar L2 contained in plasmid M15pREP (PQE-PmpE-Ct#37) (SEQ ID Nos.:72 and 73).

5. DETAILED DESCRIPTION OF THE INVENTION

5.1. *Chlamydia* PMP Polypeptides

The present invention is generally directed to compositions and methods for the diagnosis, prevention, and treatment of Chlamydial infection. In one aspect, the composition of the subject invention provides pure native (wildtype) or recombinantly produced PMP polypeptides that comprise at least one immunogenic portion of a *Chlamydia* antigen.

The terms "treatment" or "therapy" as used herein and in the claims encompasses elimination, reduction or amelioration of disease symptoms caused directly or indirectly by the organism or numbers of organisms present.

In particular embodiments, the term "*Chlamydia*" refers to any Chlamydial species (spp.) including but not limited to *Chlamydia trachomatis, Chlamydia pneumonia, Chlamydia psittaci* and *Chlamydia pecorum.*

Strains from any of these organism may be obtained worldwide from any biologicals depository, particularly strains of *Chlamydia* ATCC VR-346, VR-347, VR-348B, VR-571B, VR-572, VR-573, VR-577, VR-578, VR-878, VF-879, VP-880, VR-885, VR-886, VR-887, VR-901B, VR-902B, VR-903, VR-1355, VR-1474, VR-1477, VR-2282, which may be obtained from the ATCC.

In a particular embodiment, the *Chlamydia* PMP protein is a PMPE polypeptide comprising or consisting of the amino acid sequence of SEQ ID NO.:2 or SEQ ID NO:73. In another embodiment, the PMPE polypeptide comprises residues 32-965 of SEQ ID NO:2 or residues 23-956 of SEQ ID NO:73

In another particular embodiment, the PMPE polypeptide is encoded by the nucleotide sequence of SEQ ID NO.:1 or SEQ ID NO:72. In another embodiment, the *Chlamydia* PMPE polypeptide comprises or consists of an amino acid sequence which is homologous to SEQ ID NO.:2 or 73, or a portion thereof or is encoded by a nucleotide sequence homologous to (for example, that hybridizes under low, moderate or high stringency conditions to) the nucleotide sequence of SEQ ID NO.:1 or 72, or a portion thereof.

In another particular embodiment, the *Chlamydia* PMP protein is a PMPI protein comprising or consisting of the amino acid sequence of SEQ ID NO.:4. In another embodiment, the *Chlamydia* polypeptide is a PMPI polypeptide encoded by the nucleotide sequence of SEQ ID NO.:3 or the nucleotide sequence (specifically, the PMPI encoding portion) of plasmid TOP10 (pBAD-pmpI-Ct-Uni)#7. In another embodiment, the *Chlamydia* polypeptide comprises or consists of an amino acid sequence which is homologous to SEQ ID NO.:4, or a portion thereof, or is encoded by a nucleotide sequence homologous to (for example, that hybridizes under low, moderate or high stringency conditions to) the nucleotide sequence of SEQ ID NO.:3, or a portion thereof.

The present invention provides the family of *Chlamydia* PMPE and PMPI proteins. The amino acid sequences of SEQ ID NOs.:2, 4, and 73 and the nucleotide sequences of SEQ ID NOs.:1, 3, and 72 represent the amino acid and nucleotide sequences, respectively, of the PMPE and PMPI polypeptides, respectively, of the *Chlamydia trachomatis* L2 serovar (SEQ ID NOs.:72 and 73 being variants from a different strain of the *Chlamydia trachomatis* L2 serovar than SEQ ID NOs.: 1-4). The invention also relates to PMPE and PMPI polypeptides from other *Chlamydia trachomatis* serovars and strains and other *Chlamydia* species, as well as other derivatives and fragments thereof (i.e., PMPE- and PMPI-derived polypeptides). In a preferred embodiment, immunization with the polypeptide of the invention elicits antibodies that specifically bind to PMPE or PMPI polypeptides from other *Chlamydia* serovars and, preferably, species (preferably all species, but may be a subset of species) besides the serovar and species from which the polypeptide was isolated or derived.

As used herein a "homologous" sequence is at least 70%, preferably greater than 80%, more preferably greater than 90%, most preferably 95% or 99% identical in sequence to a reference amino acid or nucleotide sequence of identical size or when compared to a reference sequence when the alignment or comparison is conducted by a computer homology program or search algorithm known in the art. By way of example and not limitation, useful computer homology programs include the following: Basic Local Alignment Search Tool (BLAST) (Altschul et al., 1990, *J. of Molec. Biol.,* 215: 403-410, "The BLAST Algorithm"; Altschul et al., 1997, *Nuc. Acids Res.* 25:3389-3402) a heuristic search algorithm tailored to searching for sequence similarity which ascribes significance using the statistical methods of Karlin and Altschul 1990, *Proc. Nat'l Acad. Sci. USA,* 87:2264-68; 1993, *Proc. Nat'l Acad. Sci. USA* 90:5873-77. Five specific BLAST programs perform the following tasks:

1) The BLASTP program compares an amino acid query sequence against a protein sequence database.

2) The BLASTN program compares a nucleotide query sequence against a nucleotide sequence database.

3) The BLASTX program compares the six-frame conceptual translation products of a nucleotide query sequence (both strands) against a protein sequence database.

4) The TBLASTN program compares a protein query sequence against a nucleotide sequence database translated in all six reading frames (both strands).

5) The TBLASTX program compares the six-frame translations of a nucleotide query sequence against the six-frame translations of a nucleotide sequence database.

Smith-Waterman (Smith-Waterman, 1981, *J. of Molec. Biol.,* 147:195-197) is a mathematically rigorous algorithm for sequence alignments.

FASTA (see Pearson et al., 1988, *Proc. Nat'l Acad. Sci. USA,* 85:2444-2448) is a heuristic approximation to the Smith-Waterman algorithm.

By further way of example and not limitation, useful computer homology algorithms and parameters for determining percent identity include the following:

To determine the percent identity of two amino acid sequences or of two nucleotide sequences, e.g., between PMP sequences and other known sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm, a preferred, non-limiting example of a mathematical algorithm utilized for the comparison of two sequences is the algorithm of Karlin and Altschul, 1990, *Proc. Nat'l Acad. Sci. USA,* 87:2264-68; as modified by 1993, *Proc. Nat'l Acad. Sci. USA* 90:5873-77. Such algorithm is incorporated into the NBLAST and XBLAST programs of Altschul, 1990, *J. of Molec. Biol.,* 215:403-410. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilized as described in Altschul, 1997, *Nuc. Acids Res.* 25:3389-3402. Alternatively, PSI-BLAST can be used to perform an iterated search which detects distant relationships between molecules (Id.). When utilizing BLAST, Gapped BLAST, and PSI-BLAST programs, the default parameters of the respective programs can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When using the ALIGN program for comparing amino acid sequences, a PAM120 weight residue table a gap length penalty of 12, and a gap penalty of 4 can be used. Additional algorithms for sequence analysis are known in the art and include ADVANCE and ADAM as described in Torellis and Robotti (1994) *Comput. Appl. Biosc.,* 10:3-5; and FASTA described in Pearson and Lipman, 1988, *Proc. Nat'l Acad. Sci. USA,* 85:2444-2448. Within FASTA, ktup is a control option that sets the sensitivity and speed of the search. If ktup=2, similar regions in the two sequences being compared are found by looking at pairs of aligned residues; if ktup=1, single aligned amino acids are examined. Ktup can be set to 2 or 1 for protein sequences, or from 1 to 6 for nucleotide sequences. The default, if ktup is not specified, is 2 for proteins and 6 for nucleotides. Alternatively, protein sequence alignment may be carried out using the CLUSTAL W algorithm as described by Higgins et al., 1996, *Methods Enzymol.,* 266:383-402.

The percent identity between two sequences can be determined using techniques similar to those described above, with or without allowing gaps. In calculating percent identity, only exact matches are counted.

According to various aspects of the invention, the polypeptides of the invention are characterized by their apparent molecular weights based on the polypeptides' migration in SDS-PAGE (sodium dodecyl sulfate-polyacrylamide gel electrophoresis) relative to the migration of known molecular weight markers. While any molecular weight standards known in the art may be used with the SDS-PAGE, preferred molecular weight markers comprise pre-stained Myosin (250 kDa), Phosphorylase B (148 kDa), BSA (98 kDa) and GDH (64 kDa). One skilled in the art will appreciate that the polypeptides of the invention may migrate differently in different types of gel systems (e.g., different buffers; different types and concentrations of gel, crosslinkers or SDS, etc.). One skilled in the art will also appreciate that the polypeptides may have different apparent molecular weights due to different molecular weight markers used with the SDS-PAGE. Hence, the molecular weight characterization of the polypeptides of the invention is intended to be directed to cover the same polypeptides on any SDS-PAGE system and with any set of molecular weight markers which might indicate slightly different apparent molecular weights for the polypeptides than those disclosed herein.

In specific embodiments, the subject invention discloses PMP polypeptides comprising an immunogenic portion of a *Chlamydia* antigen, wherein the *Chlamydia* antigen comprises an amino acid sequence encoded by a nucleic acid molecule comprising a sequence selected from the group consisting of (a) nucleotide sequences of SEQ ID NO.:1, 3 and 72; (b) the complements of said nucleotide sequences; and (c) variants of such sequences.

5.2. *Chlamydia* PMP-Derived Polypeptides

The term "antigens" and its related term "antigenic" as used herein and in the claims refers to a substance to which an antibody or T-cell receptor specifically binds. As used herein, antisera, antibodies and T-cells are "antigen-specific" if they specifically bind to or react with an antigen and do not react detectably with unrelated proteins other than by non-specific interaction. Preferably said antigens are immunogenic.

The term "immunogenic" as used herein and in the claims refers to the ability to induce an immune response, e.g., an antibody and/or a cellular immune response in an animal, preferably a mammal or a bird.

In a specific embodiment of the invention, proteins consisting of or comprising a fragment of a PMPE protein consisting of at least 8 (contiguous) amino acids of the protein are provided. In other embodiments, the fragment consists of at least 5, 10, 20, 40, 50, 60, 80, 100, 150, 200, 300, 400 or 500 amino acids of SEQ ID NO.:2 or 73 or a sequence homologous thereto. In specific embodiments, such fragments are not larger than 10, 11, 12, 15, 20, 25, 35, 50, 75, 80, 90, 100, 125, 150, 175, 200, 225, 250, 275, 300, 325, 350, 400, 425, 450, 475, 500, 525, 550, 575, 600, 625, 650, 675 or 700 amino acids. In preferred embodiments, the PMPE-derived polypeptide contains a sequence forming an outer-surface epitope, i.e., a portion of the peptide located on the outside of the *Chlamydia* cell and that can be bound by anti-PMPE antibodies.

In a particular embodiment, the PMPE-derived polypeptide is a fragment of a PMPE polypeptide which fragment comprises or consists of an amino acid sequence of any of SEQ ID NOs.:5-22. In another particular embodiment, the PMPE-derived polypeptide is a fragment of a PMPE polypeptide, which fragment comprises or consists of an amino acid sequence of any of SEQ ID NOs.:5-22, but also comprises additional C-terminal or N-terminal PMPE sequences.

In a specific embodiment of the invention, proteins are provided that consist of or comprise a fragment of a PMPI protein consisting of at least 8 (continuous) amino acids of SEQ ID NO.:4 or a sequence homologous thereto. In other embodiments, the fragment consists of at least 5, 10, 15, 20, 25, 50, 75, 100, 150 or 200 amino acids of SEQ ID NO.:4. In specific embodiments, such fragments are not longer than 10, 11, 12, 15, 20, 25, 35, 50, 75, 80, 90, 100, 125, 150, 175, 200, 225, 250, 275, 300, 325, 350, 400, 425, 450, 475, 500, 525, 550, 575, 600, 625, 650, 675 or 700 amino acids. In preferred embodiments, PMPI-derived polypeptide contains a sequence forming an outer-surface epitope.

In a particular embodiment, the PMPI-derived polypeptide is a fragment of a PMPI peptide which comprises the amino acid sequence of any of SEQ ID NOs.:23-34.

In another particular embodiment, the PMPE-derived polypeptide is a fragment of a PMPE polypeptide which comprises the amino acid sequence of any of SEQ ID NOs.: 5-22, but also comprises additional C-terminal or N-terminal PMPI sequences.

Preferably, the PMPE-derived polypeptides of the invention are immunologically cross-reactive with the PMPE polypeptide, and are capable of eliciting in an animal an immune response to *Chlamydia, Chlamydia* elemental bodies (EB), *Chlamydia* reticulate bodies (RBs), *Chlamydia* infected cells or antigen presenting cells expressing Chlamydial antigens and/or are able to be bound by anti-PMPE antibodies.

Preferably, the PMPI-derived polypeptides of the invention are immunologically cross-reactive with the PMPI polypeptide, and are capable of eliciting in an animal an immune response to *Chlamydia, Chlamydia* elemental bodies (EB), reticulocyte bodies (RBs), *Chlamydia* infected cells or antigen presenting cells expressing Chlamydial antigens and/or are able to be bound by anti-PMPI antibodies. More preferably, the PMP-derived polypeptides of the invention comprise sequences forming one or more epitopes of the native PMPE or PMPI polypeptide of *Chlamydia* (i.e., the epitopes of PMPE or PMPI polypeptide as they exist in intact *Chlamydia* cells). Such preferred PMPE-derived or PMPI-derived polypeptides can be identified by their ability to specifically bind polyclonal or monoclonal antibodies raised to intact *Chlamydia* cells (e.g., antibodies elicited by formaldehyde or glutaraldehyde fixed *Chlamydia* cells; such antibodies are referred to herein as "anti-whole cell" antibodies). For example, peptides from a limited or complete protease digestion of the PMPE or PMPI polypeptide are fractionated using standard methods and tested for their ability to bind anti-whole cell antibodies. Reactive polypeptides are isolated and their amino acid sequence determined by methods known in the art. In a preferred embodiment, the PMPE and/or PMPI-derived polypeptide comprises one or more portions of a PMPE or PMPI protein, or derivative thereof, that is a T-cell epitope.

Preferably, the PMP polypeptides and PMP-derived polypeptides of the invention are not bound specifically by the monoclonal antibody secreted by hybridoma ATCC No. HB10861 available from the ATCC.

PMP-derived polypeptides can also be constructed by making deletions that remove a part of the parent polypeptide, while retaining the desired specific antigenicity and/or immunogenicity. Deletions can also remove regions of high variability among strains.

Also preferably, the PMP-derived polypeptides of the invention comprise sequences that form one or more epitopes of a native PMP polypeptide, which epitopes elicit bactericidal or opsonizing antibodies. Such preferred PMP-derived polypeptides may be identified by their ability to generate antibodies that kill *Chlamydia* spp., particularly, *Chlamydia trachomatis* cells. For example, polypeptides from a limited or complete protease digestion or chemical cleavage of a PMP polypeptide are fractionated using standard methods (e.g., by limited proteolytic digestion using enzymes such as trypsin, papain, or related proteolytic enzymes or by chemical cleavage using agents such as cyanogen bromide and followed by fractionation of the digestion or cleavage products), injected into animals, and the antibodies produced therefrom are tested for the ability to interfere with or kill *Chlamydia* cells and/or *Chlamydia* infected cells. Once identified and isolated, the amino acid sequences of such preferred PMP-derived polypeptides are determined using standard sequencing methods. The determined sequence may be used to enable production of such polypeptides by synthetic chemical and/or genetic engineering means.

These preferred PMP-derived polypeptides also can be identified by using anti-whole cell antibodies to screen bacterial libraries expressing random fragments of *Chlamydia* genomic DNA or cloned nucleotide sequences encoding a PMPE or PMPI polypeptide or fragments thereof. See, e.g., Sambrook et al., 1989, Molecular Cloning, A Laboratory Manual, 2nd ed., Cold Spring Harbor Press, Cold Spring Harbor, N.Y., Vol. 1, Chapter 12. The reactive clones are identified and their inserts are isolated and sequenced to determine the amino acid sequences of such preferred PMP-derived polypeptides.

Examples of immunogenic portions of antigens contemplated by the present invention include polypeptides comprising or consisting of the fragments set forth in Tables 1 and 2, where the numbers following the PMPE (Table 1, column 1) or PMPI (Table 2, column 1) designation refer to the amino acid residues in SEQ ID NOs.:2 or 4, respectively. Polypeptides comprising at least an immunogenic portion of one or more *Chlamydia* antigens or immunogenic portions as described herein may generally be used, alone or in combination, to detect, prevent, treat or reduce the severity of Chlamydial infection.

TABLE 1

PREFERRED FRAGMENTS OF PMPE

| FRAGMENT | SEO ID NO.: |
|---|---|
| PMPE15-56 | 5 |
| PMPE15-121 | 6 |
| PMPE45-125 | 7 |
| PMPE125-190 | 8 |
| PMPE195-261 | 9 |
| PMPE275-366 | 10 |
| PMPE375-440 | 11 |
| PMPE440-490 | 12 |
| PMPE525-590 | 13 |
| PMPE590-625 | 14 |
| PMPE615-650 | 15 |
| PMPE625-700 | 16 |
| PMPE725-800 | 17 |
| PMPE755-775 | 18 |
| PMPE785-845 | 19 |
| PMPE815-865 | 20 |
| PMPE1-31 | 21 |
| PMPE1-500 | 22 |

TABLE 2

PREFERRED FRAGMENTS OF PMPI

| FRAGMENT | SEQ ID NO.: |
|---|---|
| PMPI 13-40 | 23 |
| PMPI 70-110 | 24 |
| PMPI 150-225 | 25 |
| PMPI 250-290 | 26 |
| PMPI 370-455 | 27 |
| PMPI 400-455 | 28 |
| PMPI 470-520 | 29 |
| PMPI 615-670 | 30 |
| PMPI 710-775 | 31 |
| PMPI 765-825 | 32 |
| PMPI 830-860 | 33 |
| PMP 1-500 | 34 |

Polypeptides having a sequence homologous to one of the PMP polypeptides of the invention, including naturally-occurring allelic variants, as well as mutants, variants or any other non-naturally occurring variants, preferably those that cross-react with antibodies against a PMP polypeptide of the present invention, are encompassed by the present invention.

Allelic variants are very common in nature. For example, a bacterial species e.g., *C. trachomatis*, is usually represented by a variety of strains or serovars that differ from each other by minor allelic variations. Indeed, a polypeptide that fulfills the same biological function in different strains can have an amino acid sequence that is not identical in each of the strains. Such an allelic variation may be equally reflected at the nucleic acid molecule level.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells.

Nucleic acid molecules, e.g., DNA molecules, encoding allelic variants can easily be retrieved by the polymerase chain reaction (PCR) amplification of genomic bacterial DNA extracted by conventional methods. This involves the use of synthetic oligonucleotide primers matching upstream and downstream sequences of the 5' and 3' ends of the encoding domains. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total number of nucleotides in the primer.

Variants of *Chlamydia trachomatis* PMP proteins, such as PMP proteins from the A, B, Ba, C, D, Da, E, F, G, H, I, Ia, J, K, MoPN, L1, L2, and L3 serovars, which share sequence homology to the PMP polypeptides and nucleic acid molecules described herein are also provided.

"Homolog" or "homologous" is defined as being at least 70, 80, 85, 90, 95 or 99% identical to a reference sequence of identical size or when the alignment or comparison is by a computer homology program or search algorithm known in the art (see Section 5.1 supra). Preferably, the serovar homologs show 70, 80, 85, 90, 95 or 99% identity to the corresponding polypeptide sequence or sequences described herein. Most preferably, the serovar homologs show 95-99% homology to the corresponding polypeptide sequence or sequences described herein. Also, homologous nucleotide sequences exhibit 70, 80, 85, 90, 95 or 99% identity to the corresponding nucleotide sequence or sequences described herein.

A PMP-derived polypeptide of the invention may also be a modified PMPE or PMPI polypeptide or fragment thereof (i.e., a *Chlamydia* PMP polypeptide or fragment having one or more amino acid substitutions, insertions and/or deletions of the wild-type *Chlamydia* PMP sequence or amino acids chemically modified in vivo or in vitro). Such modifications may enhance the immunogenicity of the resultant PMP-derived polypeptide product or have no effect on such activity.

As used herein, the term "enhance the immunogenicity" refers to an increased antibody titer or increased cellular immune response elicited by exposure to the modified polypeptide as compared to the immune response elicited by unmodified polypeptides or formalin or glutaraldehyde fixed *Chlamydia*. Modification techniques that may be used include, but are not limited to, those disclosed in U.S. Pat. No. 4,526,716.

As an illustrative, non-limiting example, one or more amino acid residues within the PMP-derived polypeptide sequence can be substituted by another amino acid of a similar polarity which acts as a functional equivalent, resulting, for example, in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Included within the scope of the invention are PMP-derived polypeptides which are *Chlamydia* PMP polypeptide fragments or other derivatives or analogs which are differentially modified during or after translation, e.g., by glycosylation, acetylation, phosphorylation, lipidation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Furthermore, if desired, nonclassical amino acids or chemical amino acid analogs can be introduced as a substitution or addition into the PMP polypeptide sequence. Nonclassical amino acids include but are not limited to the D-isomers of the common amino acids, $\alpha$-amino isobutyric acid, 4-aminobutyric acid, Abu, 2-amino butyric acid, $\gamma$-Abu, $\epsilon$-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, $\beta$-alanine, fluoro-amino acids, designer amino acids such as $\beta$-methyl amino acids, C$\alpha$-methyl amino acids, N$\alpha$-methyl amino acids, PNA's and amino acid analogs in general. Furthermore, the amino acid can be D (dextrorotary) or L (levorotary).

A *Chlamydia* PMP-derived polypeptide may further be a chimeric polypeptide comprising one or more heterologous polypeptides, lipids, phospholipids or lipopolysaccharides of *Chlamydia* origin or of another bacterial or viral origin, fused (e.g., covalently bound) to the amino-terminus or carboxyl-terminus of or is within a complete PMPE or PMPI polypeptide or PMP-derived polypeptide. Useful heterologous polypeptides to be included within such a chimeric polypeptide include, but are not limited to, a) pre- and/or pro-sequences that facilitate the transport, translocation and/or processing of the PMP-derived polypeptide in a host cell, b) affinity purification sequences, and c) any useful immunogenic sequences (e.g., sequences encoding one or more epitopes of a surface-exposed protein of a microbial pathogen). One preferred heterologous protein of the chimeric polypeptide includes Hin47 (see U.S. Pat. Nos. 5,679,547 and 5,721,115, which are hereby incorporated by reference in their entirety). Another preferred chimeric polypeptide includes a High Molecular Weight (HMW) protein of *Chlamydia* or fragments thereof (see PCT publication WO 99/17741, entitled "*Chlamydia* Protein, Gene Sequence and Uses Thereof", which is incorporated by reference herein in its entirety) or *Chlamydia* MOMP or fragments thereof (see U.S. Pat. No. 5,869,608, which is incorporated herein by reference in its entirety). The fragments of these proteins preferably contain an epitope specifically bound by an antibody raised against the protein. A particularly preferred chimeric protein comprises one or more of: SEQ ID NOs.:5-34, an N-terminal fragment of HMW protein and a fragment of MOMP. Other preferred chimeric proteins comprise fragments of PMPE, HMW protein, MOMP, PMPH, and *C. trachomatis* HtrA. The sequences of *C. trachomatis* HtrA and *C. trachomatis* PMPH are disclosed in Stephens et al., 1998, Science 282:754-759 and in Genbank accession nos. AAC68420 (HtrA) and AE001360 (PMPH), which are all hereby incorporated by reference in their entireties.

PMP-derived polypeptides also include but are not limited to fusion polypeptides comprising at least two regions derived from one or more *Chlamydia* proteins, each having T-cell or antibody stimulating activity. The regions may be derived from the same *Chlamydia* protein or may comprise one or more regions from more than one *Chlamydia* protein. The polypeptides are arranged in a nonsequential order or noncontiguous order (e.g., in an order different from the order of the amino acids of the native protein). A preferred polypeptide of the invention is a fusion polypeptide comprising at least two peptides, each of which peptides consists of an amino acid sequence selected from the group consisting of SEQ ID NOs.:5, 6, 7, 8, 9, 10, 11, 12, 13, 14, 15, 16, 17, 18, 19, 20, 21, 22, 23, 24, 25, 26, 27, 28, 29, 30, 31, 32, 33, and 34, with the proviso that the peptides are arranged in a configuration that is different from the configuration of a naturally occurring PMPE or PMPI polypeptide.

Other preferred PMP-derived polypeptides of the invention are fusion polypeptides wherein the polypeptide comprises all the peptides consisting of the amino acid sequences of SEQ ID NOs.:5, 6, 7, 8, 9, 10 and 11, or a fusion polypeptide wherein the polypeptide comprises all the peptides consisting of the amino acid sequences of SEQ ID NOs.:23, 24, 25, 26, 27, 28, and 29, with the proviso that the peptides are arranged in a configuration that is different from the configuration of a naturally occurring PMPE or PMPI polypeptide. A preferred PMP-derived polypeptide is a fusion polypeptide comprising a peptide consisting of an amino acid sequence of any of SEQ ID NOs.:5, 6, 7, 8, 9, 10, 11, 23, 24, 25, 26, 27, 28 or 29, with the proviso that the peptides are arranged in a configuration that is different from the configuration of a naturally occurring PMPE or PMPI polypeptide. In a preferred embodiment, the fusion proteins of the invention are isolated.

Other preferred PMP-derived polypeptides of the invention are fusion proteins comprising one or more peptides comprising or consisting of the amino acid sequences of SEQ ID NOs:5-34, and one or more fragments (preferably, epitope containing fragments) of one or more other *C. trachomatis* proteins, including but not limited to HMW protein, PMPH, HtrA, and MOMP. Preferred chimeric fusion proteins comprise an amino terminal fragment of HMW protein and one or more fragments of MOMP. Particularly preferred chimeric PMPE or PMPI polypeptides comprise one or more fragments of MOMP which comprise or consist of amino acid residues 273-333, 64-85, 139-160, 224-237, 288-317, 1-200, 64-350, 160-350, 240-333 or 80-105 (for sequence and numbering, see Batteiger et al., 1996, Infect. Immun. 64:542-547 and Yuan et al., 1989, Infect. Immun., 57:1040-1049, both of which are hereby incorporated by reference in their entireties). Preferred PMPE or PMPI chimeric polypeptides may also comprise fragments of HMW protein which comprises or consists of residues 1-500 or residues 23-500 or residues 1-100, 1-200, 1-300, or 1-400. The fragments of HMW protein, MOMP, HtrA and PMPH are at least 8, 10, 15, 20, 25, 30, 50, 75 or 100 amino acid fragments.

If desired, the amino acid sequences of the regions can be produced and joined by a linker.

Suitable peptide linker sequences may be chosen based on the following factors: (1) their ability to adopt a flexible extended conformation; (2) their ability to adopt a secondary structure that could interact with functional epitopes of the first and second polypeptides; (3) the lack of hydrophobic or charged residues that might react with the polypeptide functional epitopes; (4) the ability to increase solubility; and (5) the ability to increase sensitivity to processing by antigen-presenting cells. Such linkers can be any amino acid sequence or other appropriate link or joining agent.

Linkers useful in the invention include linkers comprising a charged amino acid pair such as KK or RR, linkers sensitive to cathepsin and/or other trypsin-like enzymes, thrombin or Factor $X_a$, or linkers which result in an increase in solubility of the polypeptide.

Preferred peptide linker sequences contain Gly, Asn and Ser residues. Amino acid sequences which may be usefully employed as linkers include those disclosed in Maratea et al. *Gene* 40:39-46 (1985); Murphy et al., *Proc. Nat. Acad Sci USA* 83:8258-8562 (1986); U.S. Pat. No. 4,935,233 and U.S. Pat. No. 4,751,180. The linker sequence may be from 1 to about 50 amino acids in length.

Another particular example of fusion polypeptides of the invention includes a PMP polypeptide or PMP-derived polypeptide of the invention fused to a polypeptide having adjuvant activity, such as the subunit B of either cholera toxin or *E. coli* heat labile toxin. Another particular example of a fusion polypeptide encompassed by the invention includes a PMP polypeptide or PMP-derived polypeptide of the invention fused to a cytokine (such as, but not limited to, IL-2, IL-4, IL-10, IL-12, or interferon). A polypeptide of the invention can be fused to the N— or C-terminal end of a polypeptide having adjuvant activity. Alternatively, a polypeptide of the invention can be fused within the amino acid sequence of the polypeptide having adjuvant activity.

Also preferably, the PMP-derived fusion polypeptides of the invention comprise sequences that form one or more epitopes of a native *Chlamydia* PMP polypeptide that elicit bactericidal or opsonizing antibodies and/or T-cells. Such preferred PMP-derived polypeptides may be identified by their ability to generate antibodies and/or T-cells that kill cells infected with *Chlamydia* spp. cells particularly, *Chlamydia trachomatis* cells.

5.3. Isolation and Purification of PMP Polypeptides and PMP-Derived Polypeptides The invention provides isolated PMPE and PMPI polypeptides, PMPE-derived and PMPI-derived polypeptides. As used herein, the term "isolated" means that the product has been removed from other biological materials with which it is naturally associated, or free from other biological materials derived, for example, from a recombinant host cell that has been genetically engineered to express the polypeptide of the invention. As used herein, the term "purified" means that the product is substantially free of other biological material with which it is naturally associated, or free from other biological materials derived, for example, from a recombinant host cell that has been genetically engineered to express the polypeptide of the invention. That is, a purified PMP polypeptide composition is at least 70-95% pure PMP polypeptide by weight, preferably at least 75% pure PMP polypeptide by weight, and more preferably at least 95% pure PMP polypeptide by weight, or most preferably 98% or 99% pure PMP polypeptide by weight. Thus, a *Chlamydia* lysate or membrane preparation on an acrylamide gel (with or without SDS), including a portion of the gel containing one or more protein bands, of a *Chlamydia* lysate or membrane preparation of *Chlamydia* is not a purified preparation or composition of PMPE or PMPI, since the gel comprises other *Chlamydia* proteins and by weight PMPE or PMPI does not constitute at least 70% pure PMP polypeptide by weight, preferably at least 75% pure PMP polypeptide by weight, and more preferably at least 95% pure PMP polypeptide by weight, or most preferably 98% or 99% pure PMP polypeptide by weight of the preparation or composition. However, a preparation of PMPE or PMPI obtained by eluting the PMPE or PMPI band from the acrylamide gel is a purified preparation of PMPE or PMPI.

The PMP polypeptide of the invention may be isolated from a protein extract, including a whole cell extract of any *Chlamydia* spp., including, but not limited to, *Chlamydia trachomatis, Chlamydia pneumoniae, Chlamydia pecorum*, and *Chlamydia psittaci*. Strains from any of these organisms may be obtained worldwide from any biologicals depository, for example, strains of ATCC VR-346, VR-347, VR-348B, VR-571B, VR-572, VR-573, VR-577, VR-578, VR-878, VF-879, VR-880, VR-885, VR-886, VR-887, VR-901B, VR-902B, VR-903, VR-1355, VR-1474, VR-1477, or VR-2282 maybe obtained from the American Type Culture Collection.

Another source of the PMP polypeptide is a protein preparation from a gene expression system (such as *E. coli*) engineered to express a cloned sequence encoding a PMP polypeptide or PMP-derived polypeptide (see Section 5.5, infra).

The PMP polypeptide can be isolated and purified from the source material using any biochemical technique and approach well known to those skilled in the art. In one approach, *Chlamydia* cellular envelope is obtained by standard techniques and inner membrane, periplasmic and outer membrane proteins are solubilized using a solubilizing compound such as a detergent or hypotonic solution. A preferred detergent solution is one containing octyl glucopyranoside (OG), sarkosyl or TRITON X100™ (t-octyl phenoxy-polyethoxy-ethanol). A preferred solubilizing hypotonic solution is one containing LiCl. The PMP polypeptide is in the solubilized fraction. Cellular debris and insoluble material in the extract are separated and removed preferably by centrifugation. The polypeptides in the extract are concentrated, incubated in SDS-containing Laemmli gel sample buffer at 100° C. for 5 minutes and then fractionated by electrophoresis in a denaturing sodium dodecylsulfate (SDS) polyacrylamide gel from about 6% to about 12%, with or without a reducing agent. See Laemmli, 1970, *Nature* 227:680-685. The band or fraction identified as a PMP polypeptide, having an apparent molecular weight of about 90-115 kDa, as described above, may then be purified directly from the fraction or gel slice containing the PMP polypeptide. In a preferred embodiment, the PMP polypeptide has an apparent molecular weight of about 90-115 kDa which can be determined by comparing its migration distance or rate in denaturing SDS-PAGE relative to the migration of known molecular weight markers such as of myosin (250 kDa), Phosphorylase B (148 kDa), BSA (98 kDa) and GDH (64 kDa) (weights for pre-stained markers).

Another method of purifying PMP polypeptide is by affinity chromatography using anti-PMP antibodies (see Section 5.4). The affinity chromatography may be carried out using either polyclonal or monoclonal anti-PMP antibodies, preferably, monoclonal antibodies. The antibodies are covalently linked to agarose gels activated by cyanogen bromide or succinamide esters (Affi-Gel, BioRad, Inc.) or by other methods known to those skilled in the art. The protein extract is loaded on the top of the gel and is left in contact with the gel for a period of time and under standard reaction conditions sufficient for PMP polypeptide to bind to the antibody. Preferably, the solid support is a material used in a chromatographic column. The affinity gel is washed to remove other proteins and cell materials not bound by the anti-PMP antibody. The PMP polypeptide is then removed from the antibody to recover the PMP polypeptide in isolated, or preferably, in purified form.

A PMP-derived polypeptide of the invention can be produced by chemical and/or enzymatic cleavage or degradation of an isolated or purified PMP polypeptide. A PMP-derived polypeptide can also be chemically synthesized based on the known amino acid sequence of the PMP polypeptide and, in the case of a chimeric polypeptide, the amino acid sequence of the heterologous polypeptide, by methods well known in the art. See, for example, Creighton, 1983, *Proteins: Structures and Molecular Principles*, W.H. Freeman and Co., NY.

A PMP-derived polypeptide can also be produced in a gene expression system expressing a recombinant nucleic acid construct comprising a sequence encoding a PMP-derived polypeptide. The nucleotide sequences encoding polypeptides of the invention may be synthesized, and/or cloned, and expressed according to techniques well known to those skilled in the art. See, for example, Sambrook, et al., 1989, *Molecular Cloning A Laboratory Manual*, Vols. 1-3, Cold Spring Harbor Press, NY, Chapter 9.

PMP-derived polypeptides of the invention can be fractionated and purified by the application of standard protein purification techniques, modified and applied in accordance with the discoveries and teachings described herein. In particular, preferred PMP polypeptides of the invention, those that form an outer-surface or exposed epitope of the native PMP polypeptide, may be isolated and purified according to the affinity procedures disclosed above for the isolation and purification of a PMP polypeptide (e.g., affinity purification using anti-PMP antibodies).

If desirable, the polypeptides of the invention may be further purified using standard protein or peptide purification techniques including but not limited to, electrophoresis, centrifugation, gel filtration, precipitation, dialysis, chromatography (including ion exchange chromatography, affinity chromatography, immunoadsorbent affinity chromatography, dye-binding chromatography, size exclusion chromatography, hydroxyapatite chromatography, reverse-phase high performance liquid chromatography, and gel permeation high performance liquid chromatography), isoelectric focusing, and variations and combinations thereof.

One or more of these techniques may be employed sequentially in a procedure designed to isolate and/or purify the PMP polypeptide or the PMP-derived polypeptides of the invention according to its/their physical or chemical characteristics. These characteristics include the hydrophobicity, charge, binding capability, and molecular weight of the protein. The various fractions of materials obtained after each technique are tested for binding to the PMP receptor or ligand or to anti-PMP antibodies or for functional activity ("test" activities). Those fractions showing such test activity are then pooled and subjected to the next technique in the sequential procedure, and the new fractions are tested again. The process is repeated until fractions are obtained that have one or more of the above described "test" activities and that contain only a single band (or a very predominant band) or entity when subjected to polyacrylamide gel electrophoresis or chromatography.

5.4. PMP Immunogens and Anti-PMP Antibodies

The present invention provides antibodies that specifically bind a PMP polypeptide and/or PMP-derived polypeptide. For the production of such antibodies, isolated or, preferably, purified preparations of a PMP polypeptide or PMP-derived polypeptide are used as immunogens in an immunogenic composition. The same immunogen can be used to immunize mice for the production of hybridoma lines that produce monoclonal anti-PMP antibodies. In particular embodiments, the immunogen is an isolated or purified PMP polypeptide or PMP-derived polypeptide from any *Chlamydia* strain, including, but not limited to, *Chlamydia trachomatis, Chlamydia pneumoniae, Chlamydia pecorum*, and *Chlamydia psittaci*. Particularly preferred are the strains of *Chlamydia trachomatis* from the American Type Culture Collection (ATCC): VR-346, VR-347, VR-348B, VR-571B, VR-572, VR-573, VR-577, VR-578, VR-878, VF-879, VR-880, VR-885, VR-886, VR-887, VR-901B, VR-902B, VR-903, VR-1355, VR-1474, VR-1477, VR-2282.

In other embodiments, peptide fragments of a PMP polypeptide are used as immunogens. Preferably, peptide fragments of a purified PMP polypeptide are used. The peptides may be produced by protease digestion, chemical cleavage of isolated or purified PMP polypeptide, chemical synthesis or by recombinant expression, after which they are then isolated or purified. Such isolated or purified peptides can be used directly as immunogens. In particular embodiments, useful peptide fragments are 8 or more amino acids in length.

Useful immunogens may also comprise such peptides or peptide fragments conjugated to a carrier molecule, preferably a carrier protein. Carrier proteins may be any commonly used in immunology, include, but are not limited to, bovine serum albumin (BSA), chicken albumin, keyhole limpet hemocyanin (KLH), tetanus toxoid and the like. For a discussion of hapten protein conjugates, see, for example, Harlow and Lane *Antibodies: A Laboratory Manual*, Cold Spring Harbor Laboratory Press, Cold Spring Harbor, N.Y., 1988, or a standard immunology textbook such as Roitt, et al., *IMMUNOLOGY*, C.V. Mosby Co., St. Louis, Mo. (1985) or Klein, *IMMUNOLOGY*, Blackwell Scientific Publications, Inc., Cambridge, Mass. (1990).

In yet another embodiment, for the production of antibodies that specifically bind one or more epitopes (preferably, outer membrane epitopes) of a native PMP polypeptide, intact *Chlamydia* cells or elemental bodies (EBs) or reticulate bodies (RBs) prepared therefrom, or cells infected with *Chlamydia* are used as immunogen. The cells, EBs, RBs or cells infected with *Chlamydia* may be fixed with agents such as formaldehyde or glutaraldehyde before immunization. See Harlow and Lane, *Antibodies: A Laboratory Manual*, Cold Spring Harbor Laboratory Press, Cold Spring Harbor, N.Y., 1988, Chapter 15. It is preferred that such anti-whole cell antibodies be monoclonal antibodies. Hybridoma lines producing the desired monoclonal antibodies can be identified by using purified PMP polypeptide, intact *Chlamydia* cells, EBs, RBs or cells infected with *Chlamydia* as the screening ligand. The immunogen for inducing these antibodies may be whole *Chlamydia* cells, EBs, RBs, extracts or lysates of any *Chlamydia*, including, but not limited to, *Chlamydia trachomatis, Chlamydia pneumoniae, Chlamydia pecorum*, and *Chlamydia psittaci*. Particularly preferred are strains of *Chlamydia* strains ATCC VR-346, VR-347. VR-348B, VR-571B, VR-572, VR-573, VR-577, VR-578, VR-878, VF-879, VR-880, VR-885, VR-886, VR-887, VR-901B, VR-902B, VR-903, VR-1355, VR-1474, VR-1477, VR-2282.

Polyclonal antisera produced by immunization with cells infected with *Chlamydia*, whole cells, EBs or RBs contain antibodies that bind other *Chlamydia* proteins ("non-anti-PMP antibodies") and thus are more cumbersome to use when it is known or suspected that the sample contains other *Chlamydia* proteins or materials that are cross-reactive with these other proteins. Under such circumstances, any binding by the anti-whole cell antibodies of a given sample or band must be verified by coincidental binding of the same sample or band by antibodies that specifically bind the PMP polypeptide (e.g., anti-PMPE antibodies or anti-PMPI antibodies) and/or a PMP-derived polypeptide, or by competition tests using anti-PMP antibodies, PMP polypeptides or PMP-derived polypeptides as the competitor (i.e., addition of anti-PMP antibodies, PMP polypeptide or PMP-derived polypeptide to the reaction mix lowers or abolishes sample binding by anti-whole cell antibodies). Alternatively, such polyclonal antisera containing "non-anti-PMP" antibodies, may be cleared of such non-anti-PMP antibodies by standard approaches and methods. For example, the non-anti-PMP antibodies may be removed by precipitation with cells having a deletion of the PMP coding sequence or *Chlamydia* strains known not to have the PMP polypeptide; or by absorption to columns comprising such cells or outer membrane proteins of such cells.

In further embodiments, useful immunogens for eliciting antibodies of the invention comprise mixtures of two or more of any of the above-mentioned individual immunogens.

Immunization of animals with the immunogens described herein, preferably of humans, rabbits, rats, ferrets, mice, sheep, goats, cows or horses, is performed following procedures well known to those skilled in the art, for purposes of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. No. 4,271,145 and U.S. Pat. No. 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridomas clones are isolated, and the monoclonal antibodies are recovered from those clones.

Immunization regimens for production of both polyclonal and monoclonal antibodies are well known in the art. The immunogen may be injected by any of a number of routes, including subcutaneous, intravenous, intraperitoneal, intradermal, intramuscular, mucosal, or a combination of these. The immunogen may be injected in soluble form, aggregate form, attached to a physical carrier, or mixed with an adjuvant, using methods and materials well known in the art. The antisera and antibodies may be purified using column chromatography methods well known to those of skill in the art.

The antibodies may also be used as probes for identifying clones in expression libraries that have or may have inserts encoding one or more PMP polypeptides or fragments thereof. The antibodies, PMP polypeptides or PMP-derived polypeptides may also be used in immunoassays (e.g., ELISA, RIA, Western Blots) to specifically detect and/or quantitate *Chlamydia* or anti-*Chlamydia* antibody in biological specimens. Anti-PMP antibodies of the invention specifically bind PMP polypeptide from *Chlamydia trachomatis, Chlamydia pneumoniae, Chlamydia pecorum*, and/or *Chlamydia psittaci*. Thus anti-PMP antibodies can be used to diagnose *Chlamydia* infections.

The antibodies of the invention, including but not limited to those that are cytotoxic, cytostatic, or neutralizing, may also be used in passive immunization to prevent or attenuate

*Chlamydia* infections of animals, including humans. As used herein, a cytotoxic antibody is one that enhances opsonization and/or complement killing of the bacterium bound by the antibody. As used herein, neutralizing antibody is one that reduces the infectivity of the *Chlamydia* and/or blocks binding of *Chlamydia* to a target cell. An effective concentration of polyclonal or monoclonal antibodies raised against the immunogens of the invention may be administered to a host to achieve such effects. The exact concentration of the antibodies administered will vary according to each specific antibody preparation, but may be determined using standard techniques well known to those of ordinary skill in the art. Administration of the antibodies may be accomplished using a variety of techniques, including, but not limited to those described in Section 5.7 for the delivery of vaccines.

Another aspect of the invention is directed to antisera raised against an antigenic or immunogenic composition of the invention, and antibodies present in the antisera that specifically bind a PMP protein or a fragment or analogue thereof.

Preferably, the antibodies bind a PMP polypeptide having the amino acid sequence selected from the group consisting of SEQ ID NOs.:2, 4-34 and 73 and a PMP-derived polypeptide. Also included are monoclonal antibodies that specifically bind a PMP polypeptide having the amino acid sequence selected from the group consisting of SEQ ID NOs.:2, 4-34, and 73 and a PMP-derived polypeptide. The term "antibodies" is intended to include all forms, such as but not limited to polyclonal, monoclonal, purified IgG, IgM, or IgA antibodies and fragments thereof, including but not limited to antigen binding fragments such as Fv, single chain Fv (scFv), $F(ab.)_2$, Fab, and F(ab)' fragments (Harlow and Lane, 1988, *Antibodies: A Laboratory Manual*, Cold Spring Harbor Laboratory Press); single chain antibodies (U.S. Pat. No. 4,946,778) and complementary determining regions (CDR), (see Verhoeyen and Winter, in *Molecular Immunology* 2ed., by B. D. Hames and D. M. Glover, IRL Press, Oxford University Press, 1996, at pp. 283-325), etc.

A further aspect of the invention are chimeric or humanized antibodies (Morrison et al., 1984, *Proc. Nat'l Acad. Sci. USA* 81:6851; Reichmann et al. *Nature* 332:323: U.S. Pat. Nos. 5,225,539; 5,585,089; and 5,530,101; Neuberger et al., 1984, *Nature* 81:6851 Riechmann et al., 1988, *Nature* 332:323; U.S. Pat. Nos. 5,225,539; 5,585,089; and 5,530,101) in which one or more of the antigen binding regions of the anti-PMP antibody is introduced into the framework region of a heterologous (e.g., human) antibody. The chimeric or humanized antibodies of the invention are less antigenic in humans than non-human antibodies but have the desired antigen binding and other activities, including but not limited to neutralizing activity, cytotoxic activity, opsonizing activity or protective activity.

In a preferred embodiment, the antibodies of the invention are human antibodies. Human antibodies may be isolated, for example, from human immunoglobulin libraries (see, e.g., PCT publications WO 98/46645, WO 98/50433, WO 98/24893, WO 98/16054, WO 96/34096, WO 96/33735, and WO 91/10741) by, preferably, phage display techniques (see, e.g., Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,616,637; 5,780,225; 5,658,727; 5,733,743 and 5,969,108; each of which is incorporated herein by reference in its entirety. Human antibodies may also be generated from animals transgenic for one or more human immunoglobulin and that do not express endogenous immunoglobulins, see, e.g., U.S. Pat. No. 5,939,598 by Kucherlapati et al.

A further aspect of the invention is T-cells specific for *Chlamydia*, Chlamydial EB, RBs, *Chlamydia* infected cells or antigen presenting cells displaying Chlamydial antigens. T-cell preparations enriched for T-cells specific for PMP or PMP-derived polypeptides can be produced or isolated by methods known in the art (See section 5.8).

5.5. Nucleic Acids Encoding the PMP Polypeptide and PMP Derived Polypeptides

The isolated nucleic acids of the present invention, including DNA and RNA, comprising a sequence encoding the PMP protein or PMP-derived polypeptide thereof, may be synthesized using methods known in the art, such as using conventional chemical approaches or polymerase chain reaction (PCR) amplification using convenient pairs of oligonucleotide primers and ligase chain reaction using a battery of contiguous oligonucleotides. The sequences also allow for the identification and cloning of the PMP protein gene from any species or serovar of *Chlamydia*, for instance for screening Chlamydial genomic libraries or expression libraries as described below.

In a particular embodiment, the PMP polypeptide comprises an amino acid sequence of either SEQ ID NO.:2,4 or 73 and the nucleic acids comprise nucleotide sequences encoding said amino acid sequences. Particularly preferred fragments of PMP have 8 or more amino acids of the amino acid sequences of SEQ ID NOs.:2, 4 or 73 or sequences substantially homologous thereto, and the invention encompasses nucleic acids comprising nucleotide sequences encoding said amino acid sequences. In another particular embodiment, the PMP polypeptide is encoded by the nucleotide sequence of SEQ ID NOs.:1, 3 or 72, with particularly preferred fragments having a nucleotide sequence of NOs.:36-65, or sequences substantially homologous thereto.

The term "isolated nucleic acid" or "isolated nucleic acid molecule" is defined as a nucleic acid molecule removed from the environment in which it naturally occurs. For example, a naturally-occurring DNA molecule present in the genome of a living bacteria or as part of gene bank is not isolated, but the same molecule separated from the remaining part of the bacterial genome, as a result of, e.g., a cloning event (amplification) is isolated. Typically, an isolated DNA molecule is free from DNA regions (e.g., coding regions) with which it is immediately contiguous at the 5' or 3' end, in the naturally occurring genome. Such isolated nucleic acids or nucleic acid molecules could be part of a vector or a composition and still be isolated in that such a vector or composition is not part of its natural environment. However, "isolated nucleic acid" or "isolated nucleic acid molecule" does not include a nucleic acid that is part of a recombinant library.

Nucleic acids of the present invention can be single or double stranded. The invention also provides nucleic acids hybridizable to or complementary to SEQ ID NO.:1, 3 or 72 or fragments thereof, as well as polypeptides encoded by these nucleic acids. In specific aspects, nucleic acids are provided which comprise a sequence fully complementary to or complementary to at least 10, 15, 25, 50, 100, 200, 250, 300, 350, 400, 450, 500, 550, 600, 650, 700, 750, 800, 850, 900, 950, 1000, 1100, 1200, 1300, 1400 or 1500 contiguous nucleotides of a nucleic acid encoding a PMP polypeptide or an PMP-derived polypeptide. In a specific embodiment, a nucleic acid which is hybridizable to a nucleic acid encoding a PMP polypeptide (e.g., having a nucleotide sequence of SEQ ID NO.:1, 3 or 72 or to a nucleic acid encoding a PMP-derived polypeptide, under conditions of low, moderate or high stringency is provided). Also provided are fragments of nucleic acids encoding a PMP polypeptide or PMP-derived polypeptide of the invention (or complements thereof) where such fragments are at least 10, 15, 25, 50, 100, 200, 250, 300, 350, 400, 450, 500, 550, 600, 650, 700, 750, 800, 850, 900, 950, 1000, 1100, 1200, 1300, 1400 or 1500 nucleotides and in certain embodiments no more than 50, 75, 100, 150, 200, 250, 300, 500, 600, 800, 1000, 1500, 2000, 2500 or 3000 nucleotides in length.

By way of example and not limitation, procedures using such conditions of low stringency are as follows (see also Shilo and Weinberg, 1981, *Proc. Natl. Acad. Sci. USA* 78:6789-6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations).

In another specific embodiment, a nucleic acid which is hybridizable to a nucleic acid encoding a PMP polypeptide or a PMP-derived polypeptide under conditions of high stringency is provided. By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by awash in 0.1×SSC at 50° C. for 45 min before autoradiography. Other conditions of high stringency which may be used are well known in the art.

In another specific embodiment, a nucleic acid which is hybridizable to a nucleic acid encoding a PMP polypeptide or a PMP-derived polypeptide under conditions of moderate stringency is provided.

Various other stringency conditions which promote nucleic acid hybridization can be used. For example, hybridization in 6×SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5M $NaHPO_4$ (pH7.2)/1 mM EDTA/7% SDS, or hybridization in 50% formamide/0.25M $NaHPO_4$ (pH 7.2)/0.25 M NaCl/1 mM EDTA/7% SDS; followed by washing in 40 mM $NaHPO_4$ (pH 7.2)/1 mM EDTA/5% SDS at 42° C. or in 40 mM $NaHPO_4$ (pH7.2)/1 mM EDTA/1% SDS at 50° C. Both temperature and salt may be varied, or alternatively, one or the other variable may remain constant while the other is changed.

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., 1989, *Molecular Cloning, A Laboratory Manual*, Second Edition, Cold Spring Harbor Press, N.Y., pp. 9.47-9.57; and Ausubel et al., 1989, *Current Protocols in Molecular Biology*, Green Publishing Associates and Wiley Interscience, N.Y.

In the preparation of genomic libraries, DNA fragments are generated, some of which will encode parts or the whole of a *Chlamydia* PMPE or PMPI protein. The DNA may be cleaved at specific sites using various restriction enzymes. Alternatively, one may use DNase in the presence of manganese to fragment the DNA, or the DNA can be physically sheared, as for example, by sonication. The DNA fragments can then be separated according to size by standard techniques, including but not limited to, agarose and polyacrylamide gel electrophoresis, column chromatography and sucrose gradient centrifugation. The DNA fragments can then be inserted into suitable vectors, including but not limited to plasmids, cosmids, bacteriophages lambda or $T_4$, bacmids and yeast artificial chromosome (YAC). (See, for example, Sambrook et al., 1989, *Molecular Cloning, A Laboratory Manual,* 2d Ed., Cold Spring Harbor Laboratory Press, Cold Spring Harbor, N.Y.; Glover, D. M. (ed.), 1985, *DNA Cloning: A Practical Approach*, MRL Press, Ltd., Oxford, U.K. Vol. I, II.) The genomic library may be screened by nucleic acid hybridization to labeled probe (Benton and Davis, 1977, *Science* 196: 180; Grunstein and Hogness, 1975, *Proc. Natl. Acad. Sci. U.S.A.* 72:3961). The genomic libraries maybe screened with labeled degenerate oligonucleotide probes corresponding to the amino acid sequence of any peptide of PMP protein using optimal approaches well known in the art. Any probe used preferably is 15 nucleotides or longer.

The term "probe" as used herein refers to DNA (preferably single stranded) or RNA molecules that hybridize under stringent conditions as defined above, to nucleic acids having sequences homologous to SEQ ID NO.:1, SEQ ID NO.:3, or SEQ ID NO:72, or to a complementary or anti-sense sequence thereof. Generally, probes are significantly shorter than full-length sequences shown in SEQ ID NOs.:1, 3 or 72.

For example, they can contain from about 5 to about 100 nucleotides preferably from about 10 to about 80 nucleotides. In particular, probes have sequences that are at least 75% preferably at lest 85%, and more preferably 95%, homologous to a portion of a sequence of SEQ ID NOs.:1, 3 or 72, or complementary to such sequences. Probes can contain modified bases such as inosine, methyl-5-deoxycytidine, deoxyuridine, dimethylamino-5-deoxyuridine, or diamino-2,6 purine.

Clones in libraries with insert DNA encoding a PMP protein or a PMP-derived polypeptides will hybridize to one or more of the degenerate oligonucleotide probes. Hybridization of such oligonucleotide probes to genomic libraries is carried out using methods known in the art. For example, hybridization with the two above-mentioned oligonucleotide probes may be carried out in 2×SSC, 1.0% SDS at 50° C. and washed using the same conditions.

In yet another aspect, clones of nucleotide sequences encoding a part or the entire PMP protein or PMP-derived polypeptide may also be obtained by screening *Chlamydia* expression libraries. For example, *Chlamydia* DNA or *Chlamydia* cDNA generated from RNA is isolated and random fragments are prepared and ligated into an expression vector (e.g., a bacteriophage, plasmid, phagemid or cosmid) such that the inserted sequence in the vector is capable of being expressed by the host cell into which the vector is then introduced. Various screening assays can then be used to select for the expressed PMP-protein or PMP-derived polypeptides. In one embodiment, the various anti-PMP antibodies of the invention can be used to identify the desired clones using methods known in the art. See, for example, Harlow and Lane, 1988, *Antibodies: A Laboratory Manual*, Cold Spring Harbor Laboratory Press, Cold Spring Harbor, N.Y., Appendix IV. Clones or plaques from the library are brought into contact with the antibodies to identify those clones that bind.

In an embodiment, colonies or plaques containing DNA that encodes a PMP protein or PMP-derived polypeptide could be detected using DYNA Beads according to Olsvick et al., 29th ICAAC, Houston, Tex. 1989, incorporated herein by reference. Anti-PMP antibodies are crosslinked to DYNA Beads M280, and these antibody-containing beads are used to adsorb to colonies or plaques expressing a PMP protein or a PMP derived polypeptide. Colonies or plaques expressing a PMP protein or a PMP derived polypeptide are identified as any of those that bind the beads.

Alternatively, the anti-PMP antibodies can be nonspecifically immobilized to a suitable support, such as silica or CELITE™ resin. This material is used to adsorb to bacterial colonies expressing a PMP protein or a PMP derived polypeptide as described in the preceding paragraph.

In another aspect, PCR amplification may be used to produce substantially pure DNA encoding a part of or the whole of a PMP protein from *Chlamydia* genomic DNA. Oligonucleotide primers, degenerate or otherwise, corresponding to known PMP protein sequences can be used as primers.

In particular embodiments, an oligonucleotide encoding a portion of SEQ ID NO.:2, 4 or 73 may be used as the 5' primer. For fragment examples, a 5' primer may be made from any one of the nucleotide sequences of SEQ ID NO.:66 or 69 or any portion thereof. For 3' primers, a nucleotide sequence of SEQ ID NO.:67 or 70 or any portion thereof may be used.

As examples, an oligonucleotide encoding the N-terminal primer, and together with a 3' reverse PCR oligonucleotide complementary to an internal, dow stream protein coding sequence may be used to amplify an N-terminal-specific PMP DNA fragment. Alternatively, an oligonucleotide encoding an internal PMP coding sequence may be used as the 5' forward PCR primer together with a 3' reverse PCR oligonucleotide complementary to downstream, internal PMP protein coding sequences may be used to PCR amplify an internal PMP specific DNA fragment. Alternatively, the forward primer can be combined together with an oligonucleotide complementary to the C-terminal PMP coding region to PCR amplify the PMP ORF. These PMP specific PCR products can be cloned into appropriate expression vectors to direct the synthesis of all or part of the PMP polypeptide as distinct proteins or fusion proteins. Alternatively, these PMP specific PCR products can be appropriately labeled and used as hybridization probes to identify all or part of the PMP gene from genomic DNA libraries.

PCR can be carried out, e.g., by use of a Perkin-Elmer thermal cycler and Taq polymerase (GENE AMP™). One can choose to synthesize several different degenerate primers, for use in the PCR reactions. It is also possible to vary the stringency of hybridization conditions used in priming the PCR reactions, to allow for greater or lesser degrees of nucleotide sequence similarity between the degenerate primers and the corresponding sequences in *Chlamydia* DNA. After successful amplification of a segment of the sequence encoding a PMP protein, that segment may be molecularly cloned and sequenced, and utilized as a probe to isolate a complete genomic clone. This, in turn, will permit the determination of the gene's complete nucleotide sequence, the analysis of its expression, and the production of its protein product for functional analysis, as described infra.

Once a PMP polypeptide coding sequence has been isolated from one *Chlamydia* species, strain, or cultivar, it is possible to use the same approach to isolate PMP polypeptide coding sequences from other *Chlamydia* species, strains and cultivars. It will be recognized by those skilled in the art that the DNA or RNA sequence encoding PMP polypeptides (or fragments thereof) of the invention can be used to obtain other DNA or RNA sequences that hybridize with it under conditions of moderate to high stringency, using general techniques known in the art (see supra). Hybridization with a PMP sequence from one *Chlamydia* strain or cultivar under high stringency conditions will identify the corresponding sequences from other strains and cultivars. High stringency conditions vary with probe length and base composition. The formulae for determining such conditions are well known in the art. See Sambrook et al., 1989, *Molecular Cloning, A Laboratory Manual*, Cold Spring Harbor Press, NY, Chapter 11. As an example, high stringency hybridization conditions as applied to probes of greater than 300 bases in length involve a final wash in 0.1×SSC/0.1% SDS at 68° C. for at least 1 hour (Ausubel, et al., Eds., 1989, *Current Protocols in Molecular Biology*, Vol. I, Greene Publishing Associates, Inc and John Wiley & Sons, Inc. New York, at page 2.10.2). See also, the description of high stringency conditions, supra.

One skilled in the art would be able to identify complete clones of a PMP polypeptide coding sequence using approaches well known in the art. The extent of the PMP polypeptide coding sequence contained in an isolated clone may be ascertained by sequencing the cloned insert and comparing the deduced size of the polypeptide encoded by the open reading frames (ORFs) with that of the PMP polypeptide and/or by comparing the deduced amino acid sequence with that of known amino acid sequence of the purified PMP polypeptide. Where a partial clone of the PMP polypeptide coding sequence has been isolated, complete clones may be isolated by using the insert of the partial clone as a hybridization probe. Alternatively, a complete PMP polypeptide coding sequence can be reconstructed from overlapping partial clones by splicing their cloned PMP inserts together or by using the sequence information in the partial clones to design primers for PCR to amplify the entire PMP coding region from an appropriate source such as *Chlamydia* genomic DNA or cDNA.

Complete clones may be any that an ORF with a deduced amino acid sequence matching or homologous to that of the PMP polypeptide or, where the complete amino acid sequence of the latter is not available, matching or homologous to that of a peptide fragment of a PMP polypeptide and having a molecular weight corresponding to that of the PMP polypeptide. Further, complete clones may be identified by the ability of their inserts, when placed in an expression vector, to produce a polypeptide that binds antibodies specific to the amino-terminus of the PMP polypeptide and antibodies specific to the carboxyl-terminus of the PMP polypeptide.

Nucleic acids encoding PMP-derived polypeptides and PMP fusion proteins may be produced by methods well known in the art. In one aspect, nucleic acids encoding PMP-derived polypeptides can be derived from PMP polypeptide coding sequences by recombinant DNA methods in view of the teachings disclosed herein. For example, the coding sequence of a PMP polypeptide may be altered creating amino acid substitutions that will not affect the immunogenicity of the PMP polypeptide or which may improve its immunogenicity, such as conservative or semi-conservative substitutions as described above. Various methods may be used, including but not limited to, oligonucleotide directed, site specific mutagenesis. This and other techniques known in the art may be used to create single or multiple mutations, such as replacements, insertions, deletions, and transpositions, for example, as described in Botstein and Shortle, 1985, *Science* 229:1193-1210.

In another preferred embodiment, the nucleic acid encoding a PMPE or PMPI protein is a synthetic nucleic acid in which the codons have been optimized for increased expression in the host cell in which it is produced. The degeneracy of the genetic code permits variations of the nucleotide sequence, while still producing a polypeptide having the identical amino acid sequence as the polypeptide encoded by the native DNA sequence. The frequency of individual synonymous codons for amino acids varies widely from genome to genome among eucaryotes and procaryotes. These differences in codon choice patterns appear to contribute to the overall expression levels of individual genes by modulating peptide elongation rates. For this reason it is desirable and useful to design nucleic acid molecules intended for a particular expression system where the codon frequencies reflect the tRNA frequencies of the host cell or organism in which the protein is expressed. Native codons are exchanged for codons of highly expressed genes in the host cells. For instance, the nucleic acid molecule can be optimized for expression of the encoded protein in bacterial cells (e.g., *E. coli*), yeast (e.g., *Pichia*), insect cells (e.g., *Drosophila*), or mammalian cells or animals (e.g., human, sheep, bovine or mouse cells or animals).

Restriction enzyme sites critical for gene synthesis and DNA manipulation are preserved or destroyed to facilitate nucleic acid and vector construction and expression of the encoded protein. In constructing the synthetic genes of the invention it may be desirable to avoid CpG sequences as these sequences may cause gene silencing. Thus, in a preferred embodiment the coding region of the synthetic nucleic acid molecule does not include the sequence "CG" or includes less than 5, 8, 10, 12, 15, 20 or 30 occurrences of the sequence "CG." The codon optimized sequence is synthesized and assembled and inserted into an appropriate expression vector using conventional techniques well known to those of skill in the art.

In a particularly preferred embodiment, a synthetic nucleic acid encoding a PMPE or PMPI protein comprises at least one codon substitution in which non-preferred or less preferred codon in the natural gene encoding the protein has been replaced by a preferred codon encoding the same amino acid. For instance in humans the preferred codons are: Ala (GCC); Arg (CGC); Asn (AAC); Asp (GAC); Cys (TGC); Gln (CAG); Gly (GGC); His (CAC); Ile (ATC); Leu (CTG); Lys (AAG); Pro (CCC); Phe (TTC); Ser (AGC); Thr (ACC); Tyr (TAC); and Val (GTG). Less preferred codons are: Gly (GGG); Ile (ATT); Leu (CTC); Ser (TCC); Val (GTC); and Arg (AGG). All codons which do not fit the description of preferred codons or less preferred codons are non-preferred codons. In general, the degree of preference of a particular codon is indicated by the prevalence of the codon in highly expressed genes. Codon preference for highly expressed human genes are as indicated in Table 3. For example, "ATC" represents 77% of the Ile codons in highly expressed mammalian genes and is the preferred Ile codon; "ATT" represents 18% of the Ile codons in highly expressed mammalian genes and is the less preferred Ile codon. The sequence "ATA" represents only 5% of the Ile codons in highly expressed human genes and is a non-preferred Ile codon. Replacing a codon with another codon that is more prevalent in highly expressed human genes will generally increase expression of the gene in mammalian cells. Accordingly, the invention includes replacing a less preferred codon with a preferred codon as well as replacing a non-preferred codon with a preferred or less preferred codon.

The synthetic nucleic acid is optimized for expression of the encoded protein and at least one non-preferred or less preferred coding in a nucleic acid molecule encoding the protein is replaced by a preferred or more preferred codon encoding the same amino acid. The synthetic nucleic acid expresses the encoded protein at a level which is at least 110%, 125%, 150%, 200%, 500% of that expressed by the starting nucleic acid molecule (i.e., prior to optimization) in an in vitro cell culture system under identical conditions. In addition, preferably the synthetic nucleic acid molecule comprises fewer than 5, 8, 10, 12, 15, 20 or 30 occurrences of the sequence CG. Preferably at least 10%, 20%, 30%, 40%, 50%, 60%, 70%, 80% or 90% of the non-preferred codons and less preferred codons in the nucleic acid molecule have been replaced by preferred codons or more preferred codons.

In a particularly preferred embodiment, the nucleic acid has been optimized for expression of the encoded protein in human or mammalian cells or organisms.

TABLE 3

Codon Frequency (Percentage) in highly expressed human genes

| | | | |
|---|---|---|---|
| Ala | GC | C | 53 |
| | | T | 17 |
| | | A | 13 |
| | | G | 17 |
| Arg | CG | C | 37 |
| | | T | 7 |
| | | A | 6 |
| | | G | 21 |
| | AG | A | 10 |
| | | G | 18 |
| Asn | AA | C | 78 |
| | | T | 22 |
| Asp | GA | C | 75 |
| | | T | 25 |
| Leu | CT | C | 26 |
| | | T | 5 |
| | | A | 3 |
| | | G | 58 |
| | TT | A | 2 |
| | | G | 6 |
| Lys | AA | A | 18 |
| | | G | 82 |
| Pro | CC | C | 48 |
| | | T | 19 |
| | | A | 16 |
| | | G | 17 |

TABLE 3-continued

| Codon Frequency (Percentage) in highly expressed human genes | | | |
|---|---|---|---|
| Phe | TT | C | 80 |
| | | T | 20 |
| Cys | TG | C | 68 |
| | | T | 32 |
| Gln | CA | A | 12 |
| | | G | 88 |
| Glu | GA | A | 25 |
| | | G | 75 |
| Gly | GG | C | 50 |
| | | T | 12 |
| | | A | 14 |
| | | G | 24 |
| His | CA | C | 79 |
| | | T | 21 |
| Ile | AT | C | 77 |
| | | T | 18 |
| | | A | 5 |
| Ser | TC | C | 28 |
| | | T | 13 |
| | | A | 5 |
| | | G | 9 |
| | AG | C | 34 |
| | | T | 10 |
| Thr | AC | C | 57 |
| | | T | 14 |
| | | A | 14 |
| | | G | 15 |
| Tyr | TA | C | 74 |
| | | T | 26 |
| Val | GT | C | 25 |
| | | T | 7 |
| | | A | 5 |
| | | G | 64 |

Further, nucleic acids containing PMP polypeptide coding sequences may be truncated by restriction enzyme or exonuclease digestions. Heterologous coding sequences may be added to the PMP polypeptide coding sequence by ligation or PCR amplification Moreover, DNA encoding the whole or a part of PMP-derived polypeptide may be synthesized chemically or using PCR amplification based on the known or deduced amino acid sequence of the PMP polypeptide and any desired alterations to that sequence.

The identified and isolated DNA containing the PMP polypeptide or PMP-derived polypeptide coding sequence can be inserted into an appropriate cloning vector. A large number of vector-host systems known in the art may be used. The term "host" as used herein and in the claims refers to either in vivo in an animal or in vitro in mammalian cell cultures.

Possible vectors include, but are not limited to, plasmids and modified viruses, but the vector system must be compatible with the host cell used. Such vectors include, but are not limited to, bacteriophage such as lambda derivatives, or plasmids such as pET, pBAD, pTrcHis, pBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved DNA may be modified by homopolymeric tailing. Recombinant molecules can be introduced into host cells via transformation, transfection, infection, electroporation, etc., so that many copies of the gene sequence are generated.

In an alternative method, the desired DNA containing a PMP polypeptide or PMP-derived polypeptide coding sequence may be identified and isolated after insertion into a suitable cloning vector in a "shot gun" approach. Enrichment for the desired sequence, for example, by size fractionation, can be done before insertion into the cloning vector.

In specific embodiments, transformation of host cells with recombinant DNA molecules that contain a PMP polypeptide or PMP-derived polypeptide coding sequence enables generation of multiple copies of such coding sequence. Thus, the coding sequence may be obtained in large quantities by growing transformants, isolating the recombinant DNA molecules from the transformants and, when necessary, retrieving the inserted coding sequence from the isolated recombinant DNA.

The nucleotide sequences encoding the PMP polypeptides of the present invention are useful for their ability to selectively form duplex molecules with complementary stretches of other protein genes. Depending on the application, a variety of hybridization conditions may be employed to achieve hybridization with varying sequence identities. In specific aspects, nucleic acids are provided which comprise a sequence complementary to at least 10, 15, 25, 50, 100, 200 or 250 nucleotides of the PMP protein coding nucleic acid molecule. In specific embodiments, nucleic acids which hybridize to a PMP protein nucleic acid (e.g., having a nucleotide sequence of SEQ ID NO.:1, 3 or 72) under annealing conditions are provided.

For a high degree of selectivity, relatively stringent conditions are used to form the duplexes, such as, by way of example and not limitation, low salt and/or high temperature conditions, such as provided by 0.02 M to 0.15 M NaCl at temperatures of between about 50° C. to 70° C. For some applications, less stringent hybridization conditions are required, by way of example and not limitation, such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

5.6. Recombinant Production of PMP Polypeptide and PMP-Derived Polypeptides

In accordance with this invention, it is preferred to make the *Chlamydia* protein of the present invention by recombinant methods, particularly when the naturally occurring protein as isolated from a culture of a species of *Chlamydia* may include trace amounts of toxic materials or other contaminants. This problem can be avoided by using protein recombinantly produced in heterologous systems which can be isolated from the host in a manner to minimize contaminants in the isolated material. In this case, the PMP proteins are produced by an appropriate host cell that has been transformed by a DNA molecule that codes for the polypeptide.

The nucleic acids encoding the PMP polypeptides or PMP-derived polypeptides of the invention can be inserted into an appropriate expression vector, i.e., a vector that contains the necessary elements for the transcription and translation of the inserted polypeptide-coding sequence. The nucleotide sequences encoding the PMP polypeptides or PMP-derived polypeptides are inserted into the vectors in a manner such that they will be expressed under appropriate conditions (e.g., in proper orientation and correct reading frame). The recombinant expression vector also comprises an "expression means". The term "expression means" refers to elements of a vector which are necessary for transcription and translation of the nucleic acid encoding the protein, including but not limited to promoter/enhancer elements, a replication site, an RNA polymerase binding sequence, a ribosomal binding sequence, sequences which are capable of providing phenotype selection (e.g., ampicillin or tetracycline resistance), peptide tags that permit isolation of the expressed protein, signal sequences that direct secretion of the expressed protein and replicon and control sequences that can be used to transform host cells. The expression means is operatively coupled to the nucleic acid molecule encoding the PMP protein by linking the inserted nucleic acid molecule into the expression vector.

Promoter/enhancer elements which may be used to control expression of inserted sequences include, but are not limited to the SV40 early promoter region (Bernoist and Chambon, 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci. U.S.A.* 78:1441-1445), the regulatory sequences of the metallothionein gene (Brinster et al., 1982, *Nature* 296:39-42) for expression in animal cells; the promoters of lactamase (Villa-Kamaroff et al., 1978, *Proc. Natl. Acad. Sci. U.S.A.* 75:3727-3731), tac (DeBoer et al., 1983, *Proc. Natl. Acad. Sci. U.S.A.* 80:21-25), or trc for expression in bacterial cells (see also "Useful proteins from recombinant bacteria" in *Scientific American,* 1980, 242:74-94); the nopaline synthetase promoter region or the cauliflower mosaic virus 35S RNA promoter (Gardner et al., 1981, *Nucl. Acids Res.* 9:2871), and the promoter of the photosynthetic enzyme ribulose biphosphate carboxylase (Herrera-Estrella et al., 1984, *Nature* 310:115-120) for expression in plant cells; Gal4 promoter, the ADC (alcohol dehydrogenase) promoter, PGK (phosphoglycerol kinase) promoter, alkaline phosphatase promoter for expression in yeast or other fungi.

Depending on the host-vector system utilized, any one of a number of suitable transcription and translation elements may be used. In a preferred embodiment, a chimeric protein comprising a PMP protein or PMP-derived polypeptide sequence and a pre and/or pro sequence of the host cell is expressed. In other preferred embodiments, a chimeric protein comprising a PMP protein or PMP derived polypeptide sequence fused with, for example, an affinity purification peptide, including but not limited to, maltose binding protein, glutathione-S-transferase, thioredoxin or histidine tag, is expressed. In further preferred embodiments, a chimeric protein comprising a PMP protein or PMP-derived polypeptide sequence and a useful immunogenic peptide or protein is expressed.

Any method known in the art for inserting DNA fragments into a vector may be used to construct expression vectors containing a PMP or PMP-derived polypeptide encoding nucleic acid molecule consisting of appropriate transcriptional/translational control signals and the polypeptide coding sequences. These methods may include in vitro recombinant DNA and synthetic techniques and in vivo recombinantation (genetic recombination).

Methods of introducing exogenous DNA into yeast hosts include either the transformation of spheroplasts or of intact yeast cells treated with alkali cations. Transformation procedures usually vary with the yeast species to be transformed. See e.g., Kurtz et al. (1986) *Mol. Cell. Biol.* 6:142; Kunze et al. (1985) *J. Basic Microbiol.* 25:141; for *Candida*, Gleeson et al. (1986) *J. Gen. Microbiol.* 132:3459; Roggenkamp et al. (1986) *Mol. Gen. Genet.* 202:302; for *Hansenula;* Das et al. (1984) *J. Bacteriol.* 158:1165; De Louvencourt et al. (1983) *J. Bacteriol.* 154:1165; Van den Berg et al. (1990) *Bio/Technology* 8:135; for *Kluyveromyces;* Cregg et al. (1985) *Mol. Cell. Biol.* 5:3376; Kunze et al. (1985) *J. Basic Microbiol.* 25:141; U.S. Pat. No. 4,837,148 and U.S. Pat. No. 4,929,555; for *Pichia;* Hinnen et al. (1978) *Proc. Natl. Acad. Sci. USA* 75;1929; Ito et al. (1983) *J. Bacteriol.* 153:163; for *Saccharomyces;* Beach et al. (1981) *Nature* 300:706; for *Schizosaccharomyces;* Davidow et al. (1985) *Curr. Genet.* 10:39.

Expression vectors containing PMP polypeptide or PMP-derived polypeptide coding sequences can be identified by three general approaches: (a) nucleic acid hybridization; (b) presence or absence of "marker" gene functions; and (c) expression of inserted sequences. In the first approach, the presence of a foreign gene inserted into an expression vector can be detected by nucleic acid hybridization using probes comprising sequences that are homologous to the inserted PMP polypeptide or PMP-derived polypeptide coding sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes into the vector.

For example, *E. coli* may be transformed using pBR322 which contains genes for ampicillin and tetracycline resistance. If the PMP polypeptide or PMP-derived polypeptide coding sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of PMP polypeptide or PMP-derived polypeptide in vitro assay systems, e.g., binding of a His tag engineered into the expressed protein to a column, binding to a PMP ligand or receptor or binding with anti-PMP antibodies of the invention.

Commercially available vectors for expressing heterologous proteins in bacterial hosts include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx. For example, the phage in lambda GEM™-11 may be utilized in making recombinant phage vectors which can be used to transform host cells, such as *E. coli* LE392. In a preferred embodiment, the vector is pQE30 or pBAD/ThioE, which can be used transform host cells, such as *E. coli.*

Expression and transformation vectors for transformation into many yeast strains are available. For example, expression vectors have been developed for, the following yeasts: *Candida albicans*, Kurtz, et al. (1986) *Mol. Cell. Biol.* 6:142; *Candida maltosa*, Kunze, et al. (1985) *J. Basic Microbiol.* 25:141; *Hansenula polymorpha*, Gleeson, et al. (1986) *J. Gen. Microbiol.* 132:3459; Roggenkamp et al. (1986) *Mol. Gen. Genet.* 202:302; *Kluyveromyces fragilis*, Das, et al. (1984) *J. Bacteriol.* 158:1165; *Kluyveromyces lactis*, De Louvencourt et al. (1983) *J. Bacteriol.* 154:737; Van den Berg, et al. (1990) *Bio/Technology* 8:135; *Pichia quillerimondii*, Kunze et al. (1985) *J. Basic Microbiol.* 25:141; *Pichia pastoris*, Cregg, et al. (1985) *Mol. Cell. Biol.* 5:3376, U.S. Pat. No. 4,837,148 and U.S. Pat. No. 4,929,555; *Saccharomyces cerevisiae*, Hinnen et al. (1978) *Proc. Natl. Acad. Sci. USA* 75:1929, Ito et al. (1983) *J. Bacteriol.* 153:163; *Schizosaccharomyces pombe*, Beach et al. (1981) *Nature* 300:706; and *Yarrowia lipolytica*, Davidow, et al. (1985) *Curr. Genet.* 10:380-471, Gaillardin, et al. (1985) *Curr. Genet.* 10:49.

A variety of host-vector systems may be utilized to express the polypeptide-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA, plant cells or transgenic plants.

Hosts that are appropriate for expression of nucleic acid molecules of the present invention, fragments, analogues or variants thereof, may include *E. coli, Bacillus* species, *Haemophilus*, fungi, yeast, such as *Saccharomyces, Pichia, Bordetella*, or *Candida*, or the baculovirus expression system. Preferably, the host cell is a yeast or bacterium. In one embodiment, the host cell is an *E. coli* cell which has been genetically engineered to express epitopes of *C. trachomatis* LPS (see, e.g., U.S. Pat. No. 5,075,228, which is hereby incorporated by reference in its entirety). In a preferred embodiment, the PMP protein or PMP-derived protein is expressed in a heterologous, recombinant bacteria which has been engineered to express lpxA and/or Kdo transferase of *C. trachomatis* (for nucleotide and amino acid sequences see Genbank accession numbers AEOO1324 and AE001294, which are hereby incorporated by reference in their entirety) and is defective in its own lpxA or Kdo transferase gene. In other embodiments, the host also expresses one or more *Chlamydia*, preferably *Chlamydia trachomatis*, proteins, preferably an outer membrane protein, most preferably HMW protein, MOMP, PMPH or HtrA, or a fragment thereof.

Particularly desirable hosts for expression in this regard include Gram positive bacteria which do not have LPS and are, therefore endotoxin free. Most preferably the bacterium is *E. coli, B. subtilis* or *Salmonella*.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered PMP polypeptide or PMP-derived polypeptide may be controlled. Furthermore, different host cells have characteristic and specific mechanisms for the translational and post-translational processing and modification of proteins. Appropriate cell lines or host systems can be chosen to ensure the desired modification and processing of the foreign protein expressed.

Once a suitable host system and growth conditions are established, recombinant expression vectors can be propagated and prepared in quantity. Upon expression, a recombinant polypeptide of the invention is produced and can be recovered in a substantially purified from the cell paste, the cell extract or from the supernatant after centrifugation of the recombinant cell culture using techniques well known in the art.

For instance, the recombinant polypeptide can be purified by antibody-based affinity purification, preparative gel electrophoresis, or affinity purification using tags (e.g., 6× histidine tag) included in the recombinant polypeptide. (See, Section 5.3 supra).

5.7. Compositions

The present invention also provides therapeutic and prophylactic compositions, which may be antigenic compositions, and preferably immunogenic compositions, including vaccines, for use in the treatment or prevention of *Chlamydia* infections of animals, including mammals and birds, and more specifically rodents and primates, including humans. Preferred immunogenic compositions include vaccines for use in humans. The antigenic, preferably immunogenic, compositions of the present invention can be prepared by techniques known to those skilled in the art and comprise, for example, an immunologically effective amount of any of the PMP immunogens disclosed in Sections 5.1. or 5.2, optionally in combination with or fused to or conjugated to one or more other immunogens, including lipids, phospholipids, carbohydrates, lipopolysaccharides, inactivated or attenuated whole organisms and other proteins, of *Chlamydia* origin or other bacterial origin, a pharmaceutically acceptable carrier, optionally an appropriate adjuvant, and optionally other materials traditionally found in vaccines. In one embodiment, the invention provides a cocktail vaccine comprising several immunogens, which has the advantage that immunity against one or several strains of a single pathogen or one or several pathogens can be obtained by a single administration. Examples of other immunogens include, but are not limited to, those used in the known DPT vaccines, HMW protein of *C. trachomatis* or fragments thereof, MOMP of *C. trachomatis* or fragments thereof, or PMPH or HtrA of *C. trachomatis* or fragments thereof (preferably epitope containing fragments), entire organisms or subunits therefrom of *Chlamydia, Neisseria*, HIV, *Haemophilus influenzae, Moraxella catarrhalis*, Human papilloma virus, Herpes simplex virus, *Haemophilus ducreyi, Treponema pallidium, Candida albicans* and *Streptococcus pneumoniae*, etc. Preferred are compositions comprising one or more fragments of *C. trachomatis* MOMP which comprise or consist of residues 273-333, 64-85, 139-160, 224-237, 288-317, 1-200, 64-350, 160-350, 240-333 or 80-105. The compositions may optionally comprise HMW protein or comprise an amino-terminal fragment of HMW protein, i.e., a fragment comprising or consisting of residues 1-100, 1-200, 1-300, 1-400, or 1-500 of the mature HMW protein. The compositions may optionally comprise *Chlamydia trachomatis* LPS or LPS from a recombinant bacteria which has been engineered to express lpxA or Kdo transferase of *C. trachomatis* and which is defective in its own lpxA or Kdo transferase gene. For instance, LPS from an *E. coli* mutant defective in its lpxA transfected with nucleic acid encoding lpxA protein of *C. trachomatis* can be isolated and purified according to techniques well known in the art (Sweet et al., J. Biol. Chem. 276:19565, 2001 or Rund et al. J. Biol. Chem. 274:16819, 1999, both of which are incorporated by referenced in their entireties).

In specific embodiments, the pharmaceutical or vaccine composition comprises a PMPE or PMPI polypeptide or PMPE-derived polypeptide or PMPI-derived polypeptide and an HMW protein, or fragment thereof (preferably an at least 5, 8, 10, 20, 40, 50, 60, 80, 100, 150, 200, 300, 400 or 500 amino acid fragment and preferably an epitope containing fragment thereof). In other specific embodiments, the composition comprises a PMPE or PMPI polypeptide or PMPE-derived polypeptide or PMPI-derived polypeptide and a MOMP, or fragment thereof (preferably an at least 5, 8, 10, 20, 40, 50, 60, 80, 100, 150, 200, 300, 400 or 500 amino acid fragment and preferably an epitope containing fragment thereof).

The term "immunogenic amount" is used herein to mean an amount sufficient to induce an immune response to produce antibodies, T-cells, and/or cytokines and other cellular immune response components. Preferably, the immunogenic composition is one that elicits an immune response sufficient to prevent *Chlamydia* infections or to attenuate the severity of any preexisting or subsequent *Chlamydia* infection. An immunogenic amount of the immunogen to be used in the vaccine is determined by means known in the art in view of the teachings herein. The exact concentration will depend upon the specific immunogen to be administered, but can be determined by using standard techniques well known to those skilled in the art for assaying the development of an immune response.

The vaccine compositions of the invention elicit an immune response in a subject. Compositions which induce antibodies, including anti-PMP protein antibodies and antibodies that are opsonizing or bactericidal are one aspect of the invention. In preferred non-limiting, embodiments of the invention, an effective amount of a composition of the invention produces an elevation of antibody titer to at least three times the antibody titer prior to administration. In a preferred, specific, non-limiting embodiment of the invention, approximately 0.01 to 2000 μg and, preferably, 0.1 to 500 μg, most preferably 50 to 250 μg of the PMP protein or PMP-derived protein is administered is to a host. Compositions which induce T-cell responses which are bactericidal or reactive with host cells infected with *Chlamydia* are also an aspect of the invention. Preferred are compositions additionally comprising an adjuvant.

The combined immunogen and carrier or diluent may be an aqueous solution, emulsion or suspension or may be a dried preparation. Appropriate carriers are known to those skilled in the art and include stabilizers, diluents, and buffers. Suitable stabilizers include carbohydrates, such as sorbitol, lactose, mannitol, starch, sucrose, dextran, and glucose, and proteins, such as albumin or casein. Suitable diluents include saline, Hanks Balanced Salts, and Ringers solution. Suitable buffers include an alkali metal phosphate, an alkali metal carbonate, or an alkaline earth metal carbonate. In preferred embodiments, the composition of the invention is formulated for administration to humans.

The pharmaceutical and immunogenic compositions, including vaccines, of the invention are prepared by techniques known to those skilled in the art, given the teachings contained herein. Generally, an immunogen is mixed with the carrier to form a solution, suspension, or emulsion. One or more of the additives discussed herein may be added in the carrier or may be added subsequently. The vaccine preparations may be desiccated or lyophilized, for example, by freeze drying or spray drying for storage or formulations purposes. They may be subsequently reconstituted into liquid vaccines by the addition of an appropriate liquid carrier or administered in dry formulation using methods known to those skilled in the art, particularly in capsules or tablet forms.

An effective amount of the antigenic, immunogenic, pharmaceutical, including, but not limited to vaccine, composition of the invention should be administered, in which "effective amount" is defined as an amount that is sufficient to produce a desired prophylactic, therapeutic or ameliorative response in a subject, including but not limited to an immune response. The amount needed will vary depending upon the immunogenicity of the PMP protein, PMP-derived polypeptide or nucleic acid used, and the species and weight of the subject to be administered, but maybe ascertained using standard techniques.

Immunogenic, antigenic, pharmaceutical and vaccine compositions may further contain one or more auxiliary substance, such as wetting or emulsifying agents, pH buffering agents, or adjuvants to enhance the effectiveness thereof. Immunogenic, antigenic, pharmaceutical and vaccine compositions may be administered to birds, humans or other mammals, including ruminants, rodents or primates, by a variety of administration routes, including parenterally, intradermally, intraperitoneally, subcutaneously or intramuscularly.

Alternatively, the immunogenic, antigenic, pharmaceutical and vaccine compositions formed according to the present invention, may be formulated and delivered in a manner to evoke an immune response at mucosal surfaces. Thus, the immunogenic, antigenic, pharmaceutical and vaccine compositions may be administered to mucosal surfaces by, for example, the nasal, oral (intragastric), ocular, bronchiolar, intravaginal or intrarectal routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of microspheres, solutions, suspensions, tablets, pills, capsules, sustained release formulations or powders and contain about 0.001 to 95% of the PMP protein. Preferred dosage forms contain 50 μg to 250 μg of the PMP protein. The immunogenic, antigenic, pharmaceutical and vaccine compositions are administered in a manner compatible with the dosage formulation, and in such amount as will be therapeutically effective, protective or immunogenic. Preferred are compositions additionally comprising an adjuvant.

Further, the immunogenic, antigenic, pharmaceutical and vaccine compositions may be used in combination with or conjugated to one or more targeting molecules for delivery to specific cells of the immune system and/or mucosal surfaces. Some examples include but are not limited to vitamin B12, bacterial toxins or fragments thereof, monoclonal antibodies and other specific targeting lipids, proteins, nucleic acids or carbohydrates.

Suitable regimes for initial administration and booster doses are also variable, but may include an initial administration followed by subsequent administrations. The dose may also depend on the route(s) of administration and will vary according to the size of the host. The concentration of the PMP protein or PMP-derived polypeptide in an antigenic, immunogenic or pharmaceutical composition according to the invention is in general about 0.001 to 95%, preferably 0.01 to 5%.

The antigenic, immunogenic or pharmaceutical preparations, including vaccines, may comprise as the immunostimulating material a nucleic acid vector comprising at least a portion of the nucleic acid molecule encoding the PMP protein or PMP-derived polypeptide.

A vaccine comprising nucleic acid molecules encoding one or more PMP polypeptides, PMP-derived polypeptides or fusion proteins as described herein, such that the polypeptide is generated in situ is provided. In such vaccines, the nucleic acid molecules may be present within any of a variety of delivery systems known to those skilled in the art, including nucleic acid expression systems, bacterial and viral expression systems. Appropriate nucleic acid expression systems contain the necessary nucleotide sequences for expression in the patient such as suitable promoter and terminating signals. In a preferred embodiment, the nucleic acid molecules may be introduced using a viral expression system (e.g., vaccinia or other pox virus, alphavirus retrovirus or adenovirus) which may involve the use of non-pathogenic (defective) virus.

Techniques for incorporating nucleic acid molecules into such expression systems are well known to those of ordinary skill in the art. The nucleic acid molecules may also be administered as "naked" plasmid vectors as described, for example, in Ulmer et al. *Science* 259:1745-1749 (1992) and reviewed by Cohen, *Science* 259:1691-1692 (1993). Techniques for incorporating DNA into such vectors are well known to those of ordinary skill in the art. A vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods know to those skilled in the art.

Nucleic acid molecules (DNA or RNA) of the invention can be administered as vaccines for therapeutic or prophylactic purpose. Typically a DNA molecule is placed under the control of a promoter suitable for expression in a mammalian cell. The promoter can function ubiquitously or tissue-specifically. Examples of non-tissue specific promoters include the early cytomegalovirus (CMV) promoter (described in U.S. Pat. No. 4,168,062) and Rous Sarcoma virus promoter (described in Norton and Coffin, *Molec. Cell Biol.* 5:281 (1985)). The desmin promoter (Li et al. *Gene* 78:243 (1989); Li & Paulin, *J. Biol Chem* 266:6562 (1991); and Li & Paulin, *J. Biol Chem* 268:10401 (1993)) is tissue specific and drives expression in muscle cells. More generally, useful vectors are described in, e.g., WO 94/21797 and Hartikka et al., *Human Gene Therapy* 7:1205 (1996).

A composition of the invention can contain one or several nucleic acid molecules of the invention. It can also contain at least one additional nucleic acid molecule encoding another antigen or fragment derivative, including but not limited to, DPT vaccines, HMW protein of *C. trachomatis* or fragment thereof, MOMP of *C. trachomatis* or fragment thereof, entire organisms or subunits therefrom of *Chlamydia, Neisseria*, HIV, *Haemophilus influenzae, Moraxella catarrhalis*, Human papilloma virus, Herpes simplex virus, *Haemophilus ducreyi, Treponema pallidium, Candida albicans* and *Streptococcus pneumoniae*, etc. A nucleic acid molecule encoding a cytokine, such as interleukin-1 or interleukin-12 can also be added to the composition so that the immune response is enhanced. DNA molecules of the invention and/or additional DNA molecules may be on different plasmids or vectors in the same composition or can be carried in the same plasmid or vector.

Other formulations of nucleic acid molecules for therapeutic and prophylactic purposes include sterile saline or sterile buffered saline colloidal dispersion systems, such as macromolecule complexes, nanocapsules, silica microparticles, tungsten microparticles, gold microparticles, microspheres, beads and lipid based systems including oil-in-water emulsions, micelles, mixed micelles and liposomes. A preferred colloidal system for use as a delivery vehicle in vitro and in vivo is a liposome (i.e., an artificial vesicle). The uptake of naked nucleic acid molecules may be increased by incorporating the nucleic acid molecules into and/or onto biodegradable beads, which are efficiently transported into the cells. The preparation and use of such systems is well known in the art.

A nucleic acid molecule can be associated with agents that assist in cellular uptake. It can be formulated with a chemical agent that modifies the cellular permeability, such as bupivacaine (see, e.g., WO 94/16737).

Cationic lipids are also known in the art and are commonly used for DNA delivery. Such lipids include LIPOFECTIN™, also known as DOTMA (N-[1-(2,3-dioleyloxy)propyl]-N,N,N-trimethylammonium chloride), DOTAP (1,2-bis(oleyloxy)-3-(trimethylammonio)propane, DDAB (dimethyldioctadecylammonium bromide), DOGS (dioctadecylamidologlycy spermine) and cholesterol derivatives such as DC-Chol (3 beta-(N-(N',N'-dimethyl aminomethane)-carbamoyl)cholesterol. A description of these cationic lipids can be found in EP 187,702, WO 90/11092, U.S. Pat. No. 5,283,185, WO 91/15501, WO 95/26356, and U.S. Pat. No. 5,527,928. Cationic lipids for DNA delivery are preferably used in association with a neutral lipid such as DOPE (dioleyl phosphatidylethanolamine) as described in, e.g., WO 90/11092.

Other transfection facilitation compounds can be added to a formulation containing cationic liposomes. They include, e.g., spermine derivatives useful for facilitating the transport of DNA through the nuclear membrane (see, for example, WO 93/18759) and membrane-permeabilizing compounds such as GALA, Gramicidine S and cationic bile salts (see, for example, WO 93/19768).

The amount of nucleic acid molecule to be used in a vaccine recipient depends, e.g., on the strength of the promoter used in the DNA construct, the immunogenicity of the expressed gene product, the mode of administration and type of formulation. In general, a therapeutically or prophylactically effective dose from about 1 μg to about 1 mg, preferably from about 10 μg to about 800 μg and more preferably from about 25 μg to about 250 μg can be administered to human adults. The administration can be achieved in a single dose or repeated at intervals.

The route of administration can be any conventional route used in the vaccine field. As general guidance, a nucleic acid molecule of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal or intramuscular route. The choice of administration will depend on the formulation that is selected. For instance a nucleic acid molecule formulated in association with bupivacaine is advantageously administered into muscles.

Recombinant bacterial vaccines genetically engineered for recombinant expression of nucleic acid molecules encoding PMP or PMP-derived polypeptides include *Shigella, Salmonella, Vibrio cholerae*, and *Lactobacillus*. Recombinant BCG and *Streptococcus* expressing PMP or PMP-derived polypeptides can also be used for prevention or treatment of *Chlamydia* infections.

Non-toxicogenic *Vibrio cholerae* mutant strains that are useful as a live oral vaccine are described in Mekalanos et al. *Nature* 306:551 (1983) and U.S. Pat. No. 4,882,278. An effective vaccine dose of a *Vibrio cholerae* strain capable of expressing a polypeptide or polypeptide derivative encoded by a DNA molecule of the invention can be administered. Preferred routes of administration include all mucosal routes, most preferably intranasally or orally.

Attenuated *Salmonella typhimurium* strains, genetically engineered for recombinant expression of heterologous antigens or not and their use as oral vaccines are described in Nakayama et al. *Bio/Technology* 6:693 (1988) and WO 92/11361. Preferred routes of administration include all mucosal routes, most preferably intranasally or orally.

Other bacterial strains useful as vaccine vectors are described in High et al., *EMBO* 11:1991(1992); Sizemore et al., *Science* 270:299 (1995) (*Shigella flexneri*); Medaglini et al., *Proc Natl. Acad. Sci.* US 92:6868 (1995) (*Streptococcus gordonii*); and Flynn, *Cell Mol. Biol.* 40:31 (1994); WO 88/6626; WO 90/0594; WO 91/13157; WO 92/1796; and WO 02/21376 (Bacille Calmette Guerin).

In genetically engineered recombinant bacterial vectors, nucleic acid molecule(s) of the invention can be inserted into the bacterial genome, carried on a plasmid, or can remain in a free state.

When used as vaccine agents, recombinant bacterial or viral vaccines, nucleic acid molecules and polypeptides of the invention can be used sequentially or concomitantly as part of a multistep immunization process. For example, a mammal or bird can be initially primed with a vaccine vector of the invention such as pox virus or adenovirus, e.g., via the parenteral route or mucosally and then boosted several time with the a polypeptide e.g., via the mucosal route. In another example, a mammal can be vaccinated with polypeptide via the mucosal route and at the same time or shortly thereafter, with a nucleic acid molecule via intramuscular route.

An adjuvant can also be added to a composition containing a PMP vaccine. To efficiently induce humoral immune responses (HIR) and cell-mediated immunity (CMI), immunogens are typically emulsified in adjuvants. Immunogenicity can be significantly improved if the immunogen is co-administered with an adjuvant. Adjuvants may act by retaining the immunogen locally near the site of administration to produce a depot effect facilitating a slow, sustained release of antigen to cells of the immune system. Adjuvants can also attract cells of the immune system to an immunogen depot and stimulate such cells to elicit immune responses.

Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Aluminum hydroxide, aluminum oxide, and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum.

Other extrinsic adjuvants may include chemokines, cytokines (e.g., IL-2), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

U.S. Pat. No. 6,019,982, incorporated herein by reference, describes mutated forms of heat labile toxin of enterotoxigenic *E. coli* ("mLT"). U.S. Pat. No. 5,057,540, incorporated herein by reference, describes the adjuvant, QS21, an HPLC purified non-toxic fraction of a saponin from the bark of the South American tree *Quiliaja saponaria molina.* 3D-MPL is described in Great Britain Patent 2,220,211, which is incorporated herein by reference.

U.S. Pat. No. 4,855,283 granted to Lockhoff et al. on Aug. 8, 1989, which is incorporated herein by reference, teaches glycolipid analogues including N-glycosylamides, N-glycosylureas and N-glycosylcarbamates, each of which is substituted in the sugar residue by an amino acid, as immunomodulators or adjuvants. Lockhoff reported that N-glycosphospholipids and glycoglycerolipids are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference, teaches that octadecyl tyrosine hydrochloride (OTH) functions as an adjuvant when complexed with tetanus toxoid and formalin inactivated type I, II and III poliomyelitis virus vaccine. Lipidation of synthetic peptides has also been used to increase their immunogenicity.

Therefore, according to the invention, the immunogenic, antigenic, pharmaceutical, including vaccine, compositions comprising a PMP protein, or a PMP derived polypeptide or a PMP encoding nucleic acid or fragment thereof, vector or cell expressing the same, may further comprise an adjuvant, such as, but not limited to alum, mLT, LTR192G, QS21, RIBI DETOX™, MMPL, CpG DNA, MF59, calcium phosphate, PLG and all those listed above. Preferably, the adjuvant is selected from one or more of the following: alum, QS21, CpG DNA, PLG, LT, 3D-mPL, or Bacille Calmette-Guerine (BCG) and mutated or modified forms of the above, particularly mLT and LTR192G. The compositions of the present invention may also further comprise a suitable pharmaceutical carrier, including but not limited to saline, bicarbonate, dextrose or other aqueous solution. Other suitable pharmaceutical carriers are described in *Remington's Pharmaceutical Sciences*, Mack Publishing Company, a standard reference text in this field, which is incorporated herein by reference in its entirety.

Immunogenic, antigenic and pharmaceutical, including vaccine, compositions may be administered in a suitable, nontoxic pharmaceutical carrier, may be comprised in microcapsules, microbeads, and/or may be comprised in a sustained release implant.

Immunogenic, antigenic and pharmaceutical, including vaccine, compositions may desirably be administered at several intervals in order to sustain antibody levels and/or T-cell levels. Immunogenic, antigenic and pharmaceutical, including vaccine, compositions may be used in conjunction with other bacteriocidal or bacteriostatic methods.

Another embodiment of the vaccines of the present is a vaccine comprising one or more isolated or purified PMPE or PMPI polypeptides or PMPE-derived polypeptides or PMPI-derived polypeptides, or homologs thereof, of *Chlamydia* spp, having a molecular weight between 90 and 115 kDa as determined in SDS polyacrylamide gel electrophoresis, or isolated nucleic acids encoding a PMPE or PMPI polypeptide, or PMPE-derived polypeptide, or PMPI-polypeptide from *Chlamydia* spp., having a molecular weight between 90 and 115 kDa as determined in SDS polyacrylamide gel electrophoresis, and further comprising one or more components selected from the group consisting of alum, mLT, LTR192G, QS21, MF59, CpG DNA, MPL, calcium phosphate and PLG. Optionally, the vaccine may include HMW protein or fragments thereof, *C. trachomatis* MOMP or fragments thereof, *C. trachomatis* PMPH or fragments thereof, or *C. trachomatis* HtrA or fragments thereof, or a combination of the foregoing. The compositions may optionally comprise *trachomatis* LPS or LPS from a recombinant bacteria which has been engineered to express lpxA or Kdo transferase of *C. trachomatis* and which is defective in its own lpxA or Kdo transferase gene Also included in the invention is a method of producing an immune response in an animal comprising immunizing the animal with an effective amount of one or more of the PMP polypeptides or nucleic acid molecules encoding the PMP polypeptides of the invention, compositions comprising the same and vaccines comprising the same. The PMP polypeptides, nucleic acids, compositions and vaccines comprising the PMP polypeptides of the invention may be administered simultaneously or sequentially. Examples of simultaneous administration include cases in which two or more polypeptides, nucleic acids, compositions, or vaccines, which maybe the same or different, are administered in the same or different formulation or are administered separately, e.g., in a different or the same formulation but within a short time (such as minutes or hours) of each other. Examples of sequential administration include cases in which two or more polypeptides, nucleic acids, compositions or vaccines, which may be the same or different, are not administered together or within a short time of each other, but may be administered separately at intervals of, for example, days, weeks, months or years.

The polypeptides, nucleic acid molecules or recombinant bacterial vaccines of the present invention are also useful in the generation of antibodies, as described supra, or T-cells. For T-cells, animals, including humans, are immunized as described above. Following immunization, PBL (peripheral blood lymphocytes), spleen cells or lymph node cells are harvested and stimulated in vitro by placing large numbers of lymphocytes in flasks with media containing human serum. A polypeptide of the present invention is added to the flasks, and T-cells are harvested and placed in new flasks with X-irradiated peripheral blood mononuclear cells. The polypeptide is added directly to these flasks, and cells are grown in the presence of IL-2. As soon as the cells are shown to be *Chlamydia* specific T-cells, they are changed to a stimulation cycle with higher IL-2 concentrations (20 units) to expand them.

Alternatively, one or more T-cells that proliferate in the presence of a polypeptide of the present invention can be expanded in number by cloning. Methods for cloning cells are well known in the art. For example, T-cell lines may be established in vitro and cloned by limiting dilution. Responder T-cells are purified from the peripheral blood established in culture by stimulating with the nominal antigen in the presence of irradiated autologous filler cells. In order to generate $CD4^+$ T-cell lines, the *Chlamydia* polypeptide is used as the antigenic stimulus and autologous PBL or lymphoblastoid cell lines (LCL) immortalized by infection with Epstein Barr virus are used as antigen presenting cells. In order to generate $CD8^+$ T-cell lines, autologous antigen-presenting cells transfected with an expression vector which produces the relevant *Chlamydia* polypeptide may be used as stimulator cells. T-cell lines are established following antigen stimulation by plating stimulated T-cells in 96-well flat-bottom plates with PBL or LCL cells and recombinant interleukin-2 (rIL2) (50 U/ml). Wells with established clonal growth are identified at approximately 2-3 weeks after initial plating and restimulated with appropriate antigen in the presence of autologous antigen-presenting cells, then subsequently expanded by the addition of low doses of IL2. T-cell clones are maintained in 24-well plates by periodic restimulation with antigen and IL2 approximately every two weeks.

T-cell preparations may be further enriched by isolating T-cells specific for antigen reactivity using the methods disclosed by Kendricks et al. in U.S. Pat. No. 5,595,881.

The vaccine compositions of the present inventions are useful in preventing, treating or ameliorating disease symptoms in an animal, preferably a human, with a disease or disorder associated with *Chlamydia* infection or to prevent the occurrence or progression of a disease or disorder associated with *Chlamydia* infection in an animal, preferably a human. Such diseases or disorders include, but are not limited to, *Chlamydia* bacterial infection, conjunctivitis, urethritis, lymphogranuloma venereum (LGV), cervicitis, epididymitis, salpingitis, tubal occlusion, infertility, cervical cancer, reactive arthritis, arteriosclerosis and atherosclerosis.

5.8. Immunoassays and Diagnostic Reagents

The PMP protein, PMP-derived polypeptide or nucleic acid encoding same, and fragments thereof, are useful as diagnostic reagents. Use of the proteins and nucleic acids of the invention as an antigen or immunogen for the generation of anti-PMP protein antibodies or as an antigen in immunoassays including enzyme-linked immunosorbent assays (ELISA), radioimmunoassays (RIA) and other non-enzyme linked antibody binding assays or procedures known in the art for the detection of anti-bacterial, anti-*Chlamydia*, and anti-PMP protein antibodies are encompassed by the invention.

ELISA is well-known and routine in the art. Generally, in ELISA, the PMP protein is immobilized onto a selected surface, for example, a surface capable of binding proteins such as the wells of a polystyrene microtiter plate. After washing to remove incompletely absorbed PMP protein, a nonspecific protein solution that is known to be antigenically neutral with regard to the test sample may be bound to the selected surface. This allows for blocking of nonspecific absorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of bovine gamma globulin (BGG) and/or phosphate buffered saline (PBS)/Tween. The sample is then allowed to incubate for from 2 to 4 hours, at temperatures on the order of about 20° C. to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound PMP protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG.

To provide detecting means, the second antibody may have an associated activity such as an enzymatic activity that will generate, for example, a color development upon incubating with an appropriate chromogenic substrate. Detection may then be achieved by detecting color generation. Quantification may then be achieved by measuring the degree of color generation using, for example, a visible spectrophotometer and comparing to an appropriate standard. Any other detecting means known to those skilled in the art are included.

In Western blot assays, the polypeptide, either as a purified preparation or a cell extract, is subjected to SDS-PAGE electrophoresis, for example, as described by Laemmli, *Nature* 227:690 (1970) or any other method known in the art. After transfer to a nitrocellulose membrane, the material is further incubated with the serum sample, polyclonal antibody preparation, or monoclonal antibody diluted in the range of from about 1:5 to 1:5000, preferably from about 1:100 to about 1:500, depending upon the titer and specification of the antibodies. Appropriate dilutions can be readily determined by methods known in the art. The reaction is revealed according to standard procedures. For example, when human antibody is used, the membrane is incubated in a goat anti-human peroxidase conjugate for an appropriate length of time. The membrane is washed. The reaction is developed with the appropriate substrate and stopped. The reaction is measured visually by the appearance of a colored band e.g., by colorimetry.

In a dot blot assay, the purified or partially purified polypeptide or cell extract can be used. Briefly, a solution of the antigen at about 100 μg/ml is serially two-fold diluted in 50 mM Tris-HCl (pH 7.5). 100 μl of each dilution is applied to a 0.45 μm nitrocellulose membrane set in a 96-well dot blot apparatus. The buffer is removed by applying vacuum to the system. Wells are washed by addition of 50 μM Tris-HCl (pH 7.5) and the membrane is air-dried. The membrane is saturated in block buffer (50 mM Tris-HCl (pH 7.5), 0.15 M NaCl and 10 g/L skim milk) and incubated with an antiserum dilution from about 1:50 to about 1:500. The reaction is revealed according to standard procedures. For example, a goat anti-rabbit peroxidase conjugate is added to the well when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry.

The PMP proteins, PMP-derived polypeptides or nucleic acids encoding same, and fragments thereof, are also useful as antigens or immunogens for the generation of anti-PMP protein T-cell response or as an antigen in immunoassays, including T-cell proliferation assays, cytokine production, delayed hypersensitivity reactions or cytotoxic T-cells (CTL) reactions.

For analysis of *Chlamydia* peptide specific T-cell proliferative responses, fresh peripheral blood, spleen or lymph node cells are harvested. Cells are plated into 96-well round bottom microtiter plates and are incubated with peptides. Data is expressed as a stimulation index (SI) which is defined as the mean of the number of cells in experimental wells divided by the mean of the number of cells in control wells (no antigen).

For analysis of cytokine release of T-cells in response to *Chlamydia* polypeptides, responder cells are mixed with polypeptides. Supernatants are collected and added to an ELISA coated with antibody to the cytokine (e.g., anti-IFN-α or anti-IL-2 antibody). After washing, rabbit anti-cytokine polyclonal antibody (e.g., anti-IFN-α or anti-IL-2) is added. Labeled goat anti-rabbit IgG polyclonal is added. Substrate is added and the amount of cytokine released into the supernatant is determined based upon the amount of color developed in the ELISA.

Another embodiment includes diagnostic kits comprising all of the essential reagents required to perform a desired immunoassay according to the present invention. The diagnostic kit may be presented in a commercially packaged form as a combination of one or more containers holding the necessary reagents. Such a kit may comprise PMP protein, PMP-derived polypeptide or nucleic acid encoding same, or a monoclonal or polyclonal antibody of the present invention, in combination with several conventional kit components. Conventional kit components will be readily apparent to those skilled in the art and are disclosed in numerous publications, including, for example, Harlow and Lane, *Antibodies A Laboratory Manual*, Cold Spring Harbor Laboratory Press, Cold Spring Harbor, N.Y. 1988) which is incorporated herein by reference in its entirety. Conventional kit components may include such items as, for example, microtiter plates, buffers to maintain the pH of the assay mixture (such as, but not limited to Tris, HEPES, etc.), conjugated second antibodies, such as peroxidase conjugated anti-mouse IgG (or any anti-IgG to the animal from which the first antibody was derived) and the like, and other standard reagents.

The nucleic acid molecules containing the PMP encoding sequences of the present invention may be used in combination with an appropriate indicator means, such as a label, for determining hybridization. A wide variety of appropriate indicator means are known in the art, including radioactive, enzymatic or other ligands, such as avidin/biotin and digoxigenin-labeling, which are capable of providing a detectable signal. In some diagnostic embodiments, an enzyme tag, such as urease, alkaline phosphatase or peroxidase, instead of a radioactive tag, may be used. In the case of enzyme tags, colorimetric indicator substrates are known which can be employed to provide a means visible to the human eye or spectrophotometrically, to identify specific hybridization with samples containing PMP protein gene sequences.

Probes of the invention can be used in diagnostic tests, as capture or detection probes. Such capture probes can be conventionally immobilized on a solid support directly or indirectly, by covalent means or by passive adsorption. A detection probe can be labeled by a detection marker selected from radioactive isotopes, enzymes, such as peroxidase, alkaline phosphatase, and enzymes able to hydrolyze a chromogenic, fluorogenic or luminescent substrate; compounds that are chromogenic, fluorogenic or luminescent; nucleotide base analogs; and biotin.

Probes of the invention can be used in any conventional hybridization techniques, such as dot blot (Maniatis et al., *Molecular Cloning: A Laboratory Manual* (1982) Cold Spring Harbor Laboratory Press, Cold Spring Harbor, N.Y. 1982), Southern blot (Southern, *J. Mol. Biol.* 98:503 1975), northern blot (identical to Southern blot to the exception that RNA is used as a target), or sandwich techniques (Dunn et al., *Cell* 12:23 1977).

In embodiments involving solid-phase procedures, the test DNA (or RNA) from samples, such as clinical samples, including exudates, body fluids (e.g., serum, amniotic fluid, middle ear effusion, sputum, semen, urine, tears, mucus, bronchoalveolar lavage fluid) or even tissues, is absorbed or otherwise affixed to a selected matrix or surface. The fixed, single-stranded nucleic acid is then subjected to specific hybridization with selected probes comprising the nucleotide sequences encoding a PMP protein, or fragments or analogues thereof, under desired conditions. The selected conditions will depend on the particular criteria required and on, for example, the G+C content, type of target nucleic acid, source of nucleic acid, size of hybridization probe, etc. Following washing of the hybridization surface so as to remove non-specifically bound probe molecules, specific hybridization is detected, or even quantified, by means of the label. It is preferred to select nucleotide acid sequence portions that are conserved among species of *Chlamydia*. The selected probe may be at least 15 bp and may be in the range of about 30 to 90 bp.

The invention also relates to methods for identifying compounds which interact with and inhibit or activate an activity of the polypeptides or nucleic acid molecules of the invention comprising contacting a composition comprising the polypeptide or the nucleic acid molecule with the compound to be screened under conditions that permit interaction between the compound and the polypeptide or nucleic acid molecule to assess the interaction of a compound and to detect interaction of the compound with the polypeptide of nucleic acid. The interaction of the compound with the polypeptide or nucleic acid molecule is determined by the association of a second component (e.g., an antibody) capable of providing a detectable signal in response to the interaction of the polypeptide or nucleic acid molecule with the compound; and determining the presence or absence of a signal generated from the interaction of the compound with the polypeptide or nucleic acid molecule. Alternatively, the interaction of the compound with the polypeptide or nucleic acid molecule is determined by the ability of the compound to inhibit the activity of the polypeptide or the nucleic acid molecule. Thus, the invention also provides agonists and antagonists of the PMP polypeptides of the invention.

5.9. Applications

The proteins, polypeptides, peptides, antibodies, T-cells and nucleic acids of the invention are useful as reagents for clinical or medical diagnosis of *Chlamydia* infections and for scientific research on the properties of pathogenicity, virulence, and infectivity of *Chlamydia*, as well as host defense mechanisms. For example, DNA and RNA of the invention can be used as probes to identify the presence of *Chlamydia* in biological specimens by hybridization or PCR amplification. The DNA and RNA can also be used to identify other bacteria that might encode a polypeptide related to the *Chlamydia* PMP protein. The proteins of the invention may be used to prepare polyclonal and monoclonal antibodies that can be used to further purify compositions containing the proteins of the invention by affinity chromatography or for use as diagnostic or as prophylactic or therapeutic agents. The proteins can also be used in standard immunoassays to screen for the presence of antibodies or T-cells to *Chlamydia* in a biological sample.

5.10. Biological Deposits

Certain plasmids that contain portions of the gene having the open reading frame of the PMP genes encoding the PMP proteins of the present invention have been inserted into *E. coli* and deposited with the American Type Culture Collection (ATCC) located at 10801 University Boulevard, Manassas, Va. 20110-2209, U.S.A., pursuant to the Budapest Treaty and pursuant to 37 CFR 1.808 and prior to the filing of this application. All restrictions imposed on the availability of the deposited material will be irrevocably removed upon grant of a patent based upon this United States patent application. The invention described and claimed herein is not to be limited by the scope of the plasmids deposited, since the deposited embodiment is intended only as an illustration of the invention. Any equivalent or similar plasmids that encode similar or equivalent proteins or fragments or analogues thereof as described in this application are within the scope of the invention.

| Plasmid | ATCC Accession No. | Date Deposited |
|---|---|---|
| M15 pREP (pQE-pmpE)#37 | ATCC PTA-2462 | Sep. 12, 2000 |
| TOP10(pBAD-pmpI-Ct-Uni)#7 | ATCC PTA-2461 | Sep. 12, 2000 |

The above disclosure generally describes the present invention. A more complete understanding can be obtained by reference to the following specific examples. These examples are described solely for purposes of illustration and not intended to limit the scope of the invention. Changes in form and substitution of equivalents are contemplated as circumstances may suggest or render expedient. Although specific terms have been employed herein such terms are intended in a descriptive sense and not for purposes of limitation.

6. EXAMPLES

The above disclosure generally describes the present invention. The examples are described solely for the purpose of illustration and are not intended to limit the scope of the invention. Changes in form and substitution of equivalents are contemplated as circumstances suggest or render expedient. Although specific terms have been employed herein, such terms are intended in a descriptive sense and not for purposes of limitation.

Methods of molecular genetics, protein biochemistry and immunology used but not explicitly described in the disclosure and examples are amply reported in the scientific literature and are well within the ability of those skilled in the art.

6.1. Extraction of Envelope Proteins

McCoy cells are cultured either in standard 225 $cm^2$ tissue culture flasks or in Bellco spinner flasks (Cytodex microcarrier, Pharmacia) at 37° C. in 5% $CO_2$ using DMEM media supplemented with 10% *Chlamydia*-antibody-free fetal bovine serum, glucose and nonessential amino acids. *C. trachomatis*, including but not limited to the L2 serovar (ATCC VR-902B), elementary bodies (EBs) are prepared from lysates of infected McCoy cells. Basically, McCoy cells infected with *C. trachomatis* are sonicated and cellular debris is removed by centrifugation. The supernatant containing Chlamydial EBs is then centrifuged and the pellet containing the EBs is resuspended in Hanks' balanced salts solution (HBSS). RNAase/DNAase solution is added and incubated at 37° C. for 1 hour with occasional mixing. The EB containing solution is layered onto a discontinuous density gradient (40%, 44% and 54%) of Renogratin-60 (mixture of diatrizoate melgumine and diatrizoate sodium, Bracco Diagnostics, Princeton, N.J.) and ultracentrifuged for separation of the EBs on the gradient. After centrifugation, the EBs are harvested from the gradient between the interface of the 44% and 54% layers. The EBs are washed in phosphate buffered saline and resuspended in HBSS.

Purified EBs are sequentially extracted with 0.1% OGP [high ionic strength] in HBSS to remove peripheral surface proteins and held on ice. The same EB preparation is then extracted with 1.0% OGP, 10 mM DTT, 1 mM PMSF, and 10 mM EDTA, in a 50 mM Tris pH 7.4 buffer. The extracts are dialyzed (3500 molecular weight cut off) to remove detergent and other reagents and are concentrated by lyophilization. Eluents are dialyzed to remove excess detergent and then lyophilized. Envelope proteins are size fractionated by SDS-PAGE and visualized by silver staining or analyzed by Western blotting. Protein(s) of about 90-115 kDa present in moderate amounts are detected in the gel.

6.2. Amino Terminal Sequencing of PMP Polypeptide

To obtain the N-terminal amino acid sequence, sufficient quantities of the PMPE or PMPI protein (≧5 μg) are electroblotted onto a PVDF membrane (Applied Biosystems), and stained with Coomassie blue. Immobilized protein is released from the membrane and treated in situ with low levels of endopeptidase Lys-C, endopeptidase Arg-C and/or endopeptidase Glu-C to fragment the native protein. The resulting peptide fragments are purified by HPLC and their N-terminal amino acid sequences are determined using an ABI 430 Protein Sequenator and standard protein sequencing methodologies.

6.3. Determination of Post-Translational Modifications

Recently, several *C. trachomatis* membrane-associated proteins have been shown to be post-translationally modified.

The 18 kDa and 32 kDa cysteine-rich EB proteins, which are lectin-binding proteins, have been shown to carry specific carbohydrate moieties (Swanson et al. 1990. *Infect. Immun.* 58:502-507). Incorporation of radiolabeled palmitic acid has been used to demonstrate that the about 27 kDa *C. trachomatis* Mip-like protein is lipidated (Lundemose et al. 1993. *J. Bacteriol.* 175:3669-3671). Swanson et al. have discovered that the MOMP from the L2 serovar contains N-acetylglucosamine and/or N-acetylgalactosamine and these carbohydrate moieties mediate binding of MOMP to Hela cell membranes.

To ascertain whether the PMPE or PMPI protein is glycosylated, EBs are grown on McCoy cells in the presence of tritiated galactose or glucosamine and analyzed by SDS-PAGE and autoradiography. Briefly, McCoy cells are grown in T225 flasks under standard conditions (DMEM+10% FCS, 35 ml per flask, 10% $CO_2$) to about 90% confluency and inoculated with sufficient EBs to achieve 90%-100% infectivity. Following a 3 hour infection period at 37° C. cycloheximide is added (1 μg/ml) to inhibit host cell protein synthesis and the cultures reincubated for an additional 4-6 hours. Approximately 0.5 mCi of tritiated galactose (D-[4,5-$^3$H(N)] galactose, NEN) or glucosamine (D-[1,6-$^3$H(N)glucosamine, NEN) is then be added to each flask and the cultures allowed to incubate for an additional 30-40 hours. Cells are harvested by scraping, and EBs purified by gradient centrifugation. PMPE or PMPI protein is isolated from 1.0% OGP surface extracts, eluted with NaCl and analyzed by SDS-PAGE using $^{14}$C-labeled molecular weight markers (BRL). The resulting gel is dried and subjected to autoradiography by exposure for 1-4 weeks to Kodak X-AR film at −70° C.

To determine post synthesis lipid modification, *C. trachomatis* is cultivated on monolayers of McCoy cells according to standard procedures. Approximately 24 hours postinfection, conventional culture media (DMEM+10% FCS) is removed and replaced with a serum-free medium containing cycloheximide (1 μg/ml) and [U-$^{14}$C]palmitic acid (0.5 mCi/T225 flask, NEN) and incubated for a further 16-24 hours to allow protein lipidation to occur. Surface EB extracts are prepared and analyzed by autoradiography as described above.

6.4. Anti-PMPE or Anti-PMPI Antiserum

Antisera to PMPE or PMPI polypeptides are prepared by injecting the PMPE or PMPI polypeptide into an animal, such as a rabbit, mouse or guinea pig, with or without an adjuvant by any method generally known to those skilled in the art. For instance, PMPE is injected with Freund's complete adjuvant followed by injections of PMPE with Freund's incomplete adjuvant. Normally, a semi-purified or purified form of the protein is injected. For instance, the PMPE polypeptide is resolved from other proteins using SDS-PAGE according to standard techniques well known to those skilled in the art, as previously described (Laemmli, 1970, *Nature* 227:680-685), and cutting the PMPE-containing band out of the gel. The excised band containing PMPE is macerated and injected into an animal to generate antiserum to the PMPE polypeptide. The antisera is examined using well known and generally accepted methods of ELISA to determine titer, Western blots to determine binding to proteins, and for immunofluorescent staining and for complement-mediated cytotoxic activity against *Chlamydia.*

To aid in the characterization of the PMPE or PMPI protein, hyperimmune rabbit antisera is raised against whole EBs from *C. trachomatis*. Each animal is given a total of three immunizations of about 250 μg *Chlamydia* EBs per injection (beginning with the EBs mixed with complete Freund's adjuvant and followed with EBs mixed with incomplete Freund's adjuvant) at approximately 21 day intervals. At each immunization, approximately half of the material is administered intramuscularly (i.m.) and half is injected intranodally. Fourteen days after the third vaccination, a fourth booster of about 100 μg of EBs is given i.m. and the animals exsanguinated 7-10 days later.

6.5. ELISA

Anti-PMPE or anti-PMPI antibody titers are measured by ELISA using purified PMPE or PMPI protein (~1 μg/well) or *C. trachomatis* EBs (whole or crude protein extracts) or cells infected with *Chlamydia* as capture ligands by any method known by those skilled in the art. Serial dilutions of antisera are made in PBS and tested by ELISA in duplicate. HRP-conjugated antibody is diluted and used as the second reporter antibody in these assays. Titers are expressed as the greatest dilution showing positive ELISA reaction, i.e., an O.D. 450 value>2SD above the mean negative control value (pre-bleed rabbit sera).

6.6. Western Blots

*Chlamydia trachomatis* is grown in McCoy cells and *Chlamydia* cell lysates are prepared as described in section 6.1, supra. The solubilized cells are resolved on 12% polyacrylamide gels and the separated proteins were electrophoretically transferred to PVDF membranes at 100 V for 1.5 hours as previously described (Thebaine et al. 1979, *Proc. Natl. Acad. Sci. USA* 76:4350-4354). The PVDF membranes are then pretreated with 25 ml of Dulbecco's phosphate buffered saline containing 0.5% sodium casein, 0.5% bovine serum albumin and 1% goat serum. All subsequent incubations are carried out using this pretreatment buffer.

PVDF membranes are incubated with 25 ml of a dilution of preimmune rabbit serum or serum from a rabbit immunized with PMPE or PMPI polypeptide (as described above) for 1 hour at room temperature or with monoclonal antibodies to PMPE or PMPI. PVDF membranes are then washed twice with wash buffer (20 mM Tris buffer [pH 7.5.] containing 150 mM sodium chloride and 0.05% Tween-20). PVDF membranes are incubated with 25 ml peroxidase-labeled goat anti-rabbit (or anti-mouse for monoclonals) IgG (Jackson ImmunoResearch Laboratories, West Grove, Pa.) for 30 minutes at room temperature. PVDF membranes are then washed 4 times with wash buffer, and are developed with 3,3'diaminobenzidine tetra-hydrochloride and urea peroxide as supplied by Sigma Chemical Co. (St. Louis, Mo.; catalog number D-4418) for 4 minutes each.

Hyperimmune antisera or monoclonal antibody is used to probe Western blots of crude EB or RB extracts as well as 1.0% OGP EB extract preparations to identify PMPE or PMPI polypeptides from other *C. trachomatis* serovars and *Chlamydia* species. Lysates from *C. trachomatis* A, B, Ba, C, D, Da, E, F, G, H, I, Ia, J, K, L1, L2, L3, or MoPn serovars or *Chlamydia pneumoniae* are electrophoresed to identify proteins reactive with antisera generated against PMPE or PMPI protein.

6.7. Cellular Envelope Location of PMPE and PMPI

Surface localization of the PMPE or PMPI protein on different *Chlamydia* strains and derivatives is examined by indirect fluorescence antibody (IFA). IFA is performed using the procedures generally known by those skilled in the art using hyperimmune anti-PMPE or PMPI protein as the primary antibody. Hak cells infected with whole EBs from *C. trachomatis* are achieved by the following method.

McCoy or Hak cells are grown to confluence in D-MEM media on 12 mm plain coverslips inside 24 well tissue culture plates then centrifugally inoculated with ~5×10$^4$ inclusion forming units (IFU) of the *C. trachomatis*. After ~24 hours incubation, the culture media is removed and infected cells fixed in methanol for 10 min. The fixed monolayer is then washed with PBS (1×) to remove fixative and overlayered with >300 l of anti-PMPE or PMPI rabbit antibody that has been diluted in PBS. After 1 hour incubation with the primary antibody, the cells are washed gently with PBS then incubated for ~30 minutes with mouse anti-rabbit IgG antibody conjugated with FITC. The second antibody is diluted using a PBS solution containing 0.0091% Evans Blue as a counter stain to visualize the monolayer. Cells are washed 2× in PBS to remove the secondary antibody, the coverslips are removed from the culture plates, and mounted onto microscope slides using a fluorescent mounting medium.

Identical cell samples are stained with pre-bleed rabbit antibody or FITC-conjugated second antibody alone are processed in parallel and served as antibody specificity (negative) controls. Counterstained samples are examined at a 1000-× magnification with a Zeiss Axioskop photomicroscope equipped with plan-neoflur objectives.

6.8. Properties of PMPE and PMPI Polypeptides

PMPE polypeptide exists as a protein of approximately 90-115 KDa in its native state as determined via Western blots of crude EB or RB extracts of *Chlamydia*, as described in Section 6.1. PMPI polypeptide exists as a protein of approximately 90-115 KDa in its native state as determined via Western blots of crude EB or RB extracts of *Chlamydia.*

The isoelectric point of the PMPE protein is about 7.17. The isoelectric point of the PMPI protein is about 6.36.

6.9. Vaccine Efficacy

An in vitro neutralization model using methods generally known to those skilled in the art is used to show that protective antiserum inhibits Chlamydial infection (neutralization) of various tissue culture cell lines. Animal models are also essential for testing vaccine efficacy with both small animal (non-primate) and primate models necessary for preclinical evaluation. The guinea-pig is used for studying experimental ocular and genital infection by the Guinea-pig inclusion conjunctivitis agent (GPIC), *C. psittaci.*

The mouse offers a consistent and reproducible model of genital tract infection using human genital tract isolates. This mouse model is a generally accepted pre-clinical assay and was used to evaluate MOMP as a subunit vaccine. Another model is known as the primate model of trachoma infection wherein the induction of secretory IgA was shown to be a prime component of protection. Vaccinogenic ability of new subunit antigen candidates is determined using the above-mentioned generally accepted in vitro neutralization and animal model systems.

6.9.1 In Vitro Neutralization Model

As a preliminary exercise to the animal protection studies, hyperimmune anti-PMPE or PMPI antibody is evaluated for its ability to block the infectivity of various *C. trachomatis* serovars (e.g., L2, B, F) in vitro. Although McCoy cells are used to propagate *Chlamydia*, these cells also allow antibody-mediated uptake via Fc receptors. Therefore, to evaluate anti-PMPE or anti-PMPI antibody inhibition of infectivity, Hak cells, which do not display Fe receptors, are used in these analyses.

Cells are grown on coverslips in 24-well plates to a sub-confluent monolayer (about 90% confluency=$1\times10^5$ cells/ml) at 37° C. in 5% $CO_2$. Anti-PMPE or PMPI antibody is diluted to about 100 μg/ml (total protein) in sucrose-phosphate-glutamate (SPG) buffer and then serially diluted in SPG buffer. Frozen aliquots of pretitered *Chlamydia* EBs are diluted in SPG buffer to about $2\times10^4$ IFU (inclusion forming units)/ml. EBs are premixed with the diluted anti-PMPE or PMPI antibody and incubated 30 minutes at 37° C. on a rocking platform.

Prepared Hak cells are washed in HBSS and then incubated with the anti-PMPE or PMPI antibody/*Chlamydia* EB mixture in triplicate for each antibody using ~500 IFU/ml. Plates are centrifuged at ~500 rpm at room temperature for 1 hour then incubated for 2 hours at 37° C. or are incubated for 2 hours at 37° C. without prior centrifugation to allow EB infection of the monolayer. Then the inoculum is removed and plates washed 3 times with HBSS. Tissue culture media containing 1 μg/ml of cycloheximide is added and plates incubated for about 24-48 hours at 37° C. in 5% $CO_2$ to allow inclusion bodies to develop. After incubation, the media is removed and cell monolayers washed 3× in PBS. Plates are fixed in methanol for 20 minutes and re-washed in PBS.

Cells are stained to visualize inclusions by incubating with anti-*Chlamydia* LPS antibody (diluted about 1:500), washed 3 times in PBS, followed by incubation with FITC-conjugated goat secondary antibody for 30 minutes at 37° C. Coverslips are washed, air dried, and mounted in glycerol on glass slides. Inclusions are counted in five fields through the midline of the coverslip on a Zeiss fluorescence photomicroscope. Results are reported as the percent reduction of inclusion-containing cells with respect to a heterogenous antibody control (rabbit pre-bleed sera).

6.9.2 Vaccine Efficacy (Mouse Model of Salpingitis and Fertility)

Immunization and Challenge

The Tuffrey murine infertility model is employed to evaluate the efficacy of rPMPE or rPMPI to protect animals against *Chlamydia trachomatis*-induced salpingitis and infertility. Three groups of female C3HeOuJ mice (6 weeks of age, Jackson Labs) are employed for this evaluation. The test group is immunized (e.g., intradermally, intraperitoneal, subcutaneously, intramuscularly, or mucosally) by administration of a vaccine formulation containing approximately 10-100 μg of purified rPMPE or rPMPI and adjuvant. For instance, mice that are immunized intranasally are sedated using an anesthesia cocktail consisting of 16% Ketaject and 16% Xlaject in 68% pyrogen-free PBS (100 μl) i.p./animal. Sedated animals are placed on their backs and using a standard laboratory pipette administered the vaccine formulations; approximately 10 μl of the vaccine solution per nostril with a 5-10 minute wait period between applications.

Two groups of female mice are immunized similarly but with a preparation containing adjuvant only, no antigen. One of these groups is subsequently challenged with *C. trachomatis* (sham immunized, infected) and serves as the negative fertility control while the other group is not challenged (sham immunized, sham infected) and serves as the positive fertility control.

At week 4, all animals are administered a single i.p. dose of progesterone (2.5 mg in pyrogen-free PBS, Depo-Provera, Upjohn) to stabilize the uterine epithelium. At week 5, animals immunized with rPMPE or rPMPI and animals in the negative control group are infected by bilateral intrauterine inoculation with approximately $5\times10^5$ IFU of *C. trachomatis* (including but not limited to, from serovar F, strain NI1) in 100 μl of sucrose phosphate glutamate buffer (SPG). To mimic the manipulations to the reproductive tract experienced by the other groups, animals in the positive control are bilaterally inoculated with 100 μl of a McCoy cell extract that contains no *C. trachomatis*. At week 7, animals from each group are sacrificed by $CO_2$ asphyxiation and the complete genital tract (both upper and lower reproductive tracts) are removed for histopathological analysis. At week 9, the remaining females from each group are caged with 8-10 week old male C3H mice for a 2 month breeding period to assess fertility (1 male for every 2 females per cage with weekly rotation of the males within each group, animals from different experimental groups were not mixed). Palpation and periodic weighing are used to determine when animals in each pair become pregnant. The parameters used to estimate group fertility are: F, the number of mice which littered at least once during the mating period divided by the total number of mice in that study group; M, the number of newborn mice (born dead or alive) divided by the number of litters produced in that group during the mating period; and N, the number of newborn mice (born dead or alive) divided by the total number of mice in that group.

Histopathology

Genital tracts are treated for >24 hours in Bouin's fixative, progressively dehydrated in 50%, 70% and 100% methanol, soaked in toluol, and either paraffin embedded or directly embedded in OCT compound (Tissue-TEK, Miles) and subsequently snap frozen in liquid nitrogen. Tissue sections (approximately 6 μm) are stained with hematoxylin and eosin (after deparaffinization of the Bouin fixed samples). Inflammatory changes in the oviducts and ovaries are graded as follows: 0, no apparent inflammatory reaction; 1, a few mononuclear cells infiltrating the periovarial space or the submucosa of the oviduct; 2, same as 1 but to a greater extent; 3, same as 2 but with a thickened oviductal submucosa and the presence of inflammatory cells in the oviductal lumen; 4, same as 3 but to a greater extent. Inflammation in the cervix/vagina is scored based on the level of the intraepithelial infiltrate observed.

Determination of rPMPE or rPMPI Specific Humoral Responses

Blood samples are collected periodically during the immunization and challenge phases by retroorbital bleeding and serum prepared by centrifugation. Vaginal secretions are collected by repeated injection of 50-100 μl of sterile PBS into the vagina with a standard laboratory pipetter and immediately withdrawing the solution. Two to three injection/withdrawal cycles are performed.

Quantitation of antibody (Ab) responses by ELISA are performed as described in Section 6.5. Microwell ELISA plates (Maxisorb, NUNC) for determining antibody levels are coated overnight at 4° C. with ~0.5-1.0 μg of purified rPMPE or rPMPI per well in 10 mM carbonate/bicarbonate buffer (pH 9.6), washed with PBS containing 0.1% Tween-20 (washing buffer) and blocked for ~1 hr at 37° C. with a PBS solution containing 3% BSA. For the determination of antigen-specific serum IgG levels, test sera or vaginal secretions are serially diluted in washing buffer containing 0.5% BSA and aliquots (100 (l) incubated in the antigen-coated wells for ~2 hr at 37° C. The plates are then washed and incubated for ~1 hr at 37° C. with a horseradish peroxidase (HRP)-conjugated goat anti-mouse IgG second antibody (Sigma). A HRP-conjugated goat anti-mouse IgA secondary antibody is used to detect the presence of rPMPE or rPMPI specific IgA in serum or vaginal secretions. After incubation with the appropriate secondary Ab, the plates are washed and incubated for ~20-30 minutes at room temperature with TMB substrate (Sigma). Reactions are stopped by the addition of 2M $H_2SO_4$ and the absorbance determined at 450 nm on a Molecular Devices SpectroMax microplate reader. Titers are determined as the reciprocal of the sample dilution corresponding to an optical density of 1.0 at 450 nm.

Determination of rPMPE or rPMPI Specific Cellular Responses

Groups of mice are immunized with rPMPE or rPMPI plus adjuvant vaccine as described above. At week 5, animals from each group are sacrificed by $CO_2$ asphyxiation, spleens removed and single cell suspensions prepared using conventional methodologies. For cellular assessment, animals are not treated with hormone. For both the positive control group (sham immunized and sham infected) and the negative control group (sham immunized, infected), spleen cells are pooled and tested for restimulation.

For the measurement of spleen cell proliferation, spleens are ground (5 to 10 rounds) in 5 ml RPMI 1640 Glutamax I supplemented with 10% fetal calf serum, 25 mM HEPES, 50 U/ml penicillin, 50 μg/ml streptomycin, 1 mM sodium pyruvate, nonessential amino acids, and 50 mM 2-mercaptoethanol (Gibco-BRL). Live cells are counted by Trypan Blue staining and diluted in the same media to reach a density of $1.0\text{-}2.0\times10^6$ cells/ml (Falcon 2063 polypropylene tubes). Triplicate cultures are set-up in round bottom 96-well culture plates (Nunclon, Nunc) using $\sim5\times10^5$ responder cells per well in 200 μl of media. Cells are stimulated with rPMPE or rPMPI (antigen-specific proliferation) or with concanavalin A (Boerhinger Mannheim) as a positive stimulation control; unstimulated cell cultures are used as a negative control of cellular activation. After 72-96 hours of incubation at 37° C. in 5% $CO_2$, cells are pulsed labeled for ~18 hrs with 1.0 Ci $^3$H-thymidine (Amersham) per well. Pulsed cells are harvested onto glass-fiber sheets using a Tomtec Cell Harvester (Mk III) and counted for beta-emission in a 3-channel Wallac 1450 Trilux Liquid Scintillation Counter. The stimulation index (SI) for a sample (individual or pooled) is defined as the mean of the antigen or ConA-stimulated T-cell uptake of $^3$H-thymidine for triplicate wells divided by the mean of the unstimulated uptake for triplicate wells. SIs for both antigen-specific (rPMPE or rPMPI-specific) and ConA-specific proliferation are determined.

Results presented in FIG. 7 demonstrate that animals immunized with recombinant PMPE protein develop a strong and uniform antigen-specific T-cell proliferative response. These data also show that T-cells from animals immunized with recombinant PMPE recognize and are strongly stimulated by the infectious EB form of *C. trachomatis.*

6.10. Isolation of *C. Trachomatis Chromosomal DNA*

*Chlamydia trachomatis* were grown as described supra in Section 6.1. Gradient purified EBs were suspended in ~5.0 ml of sterile water. An equal volume of lysis buffer (200 mM NaCl, 20 mM EDTA, 40 mM Tris-HCl pH 8.0, 0.5% (w/v) SDS, 0.5% (v/v) 2-mercaptoethanol, and 250 μg/ml of proteinase K) was added and the cells suspended by gentle agitation and trituration. The cell suspension was then incubated ~12 hours at 50° C. to lyse the EBs and liberate chromosomal DNA. Proteinaceous material was precipitated by the addition of 5.0 ml of saturated NaCl (~6.0 M, in sterile water) and centrifugation at ~5,500×g in a Sorval SS34 rotor at room temperature. Chromosomal DNA was precipitated from the cleared supernatant by the addition of two volumes of 100% ethanol. Aggregated DNA was collected and washed using gentle agitation in a small volume of a 70% ethanol solution. Purified chromosomal DNA was suspended in sterile water and allowed to dissolve/disburse overnight at 4° C. by gentle rocking. The concentration of dissolved DNA was determined spectrophotometrically at 260 nm using an extinction coefficient of 1.0 O.D. unit ~50 μg/ml.

6.11. PCR Cloning of the PMPE ORF

To produce high levels of recombinant PMPE protein for immunogenicity and protective efficacy studies, the PMPE ORF was PCR cloned into an *E. coli* high expression vector, pQE-30 (QiaGen). Genes cloned into the pQE-30 vector are expressed from a T5 promoter which is under the control of the lac operator. Genes cloned into pQE-30 are expressed as a fusion protein containing a Met-Arg-Gly-Ser-$(His)_6$ (SEQ ID NO.:71) N terminus. An additional 15 amino acid segment encoded by vector sequences residing between the $(His)_6$ domain and the SalI site are also part of the N terminus. Oligonucleotide PCR primers complementary to the DNA sequences encoding the first 10 amino acid residues of the N-terminus of the mature protein and the last 9 C-terminal amino acid residues of the *C. trachomatis* serovar L2 PMPE ORF present in the UC Berkeley genomic database (see Stephens et al., 1998, Science: 282: 754-759 and GenBank Accession No. NC000117) were synthesized. In addition to the PMPE specific sequences, these PCR primers were designed to contain flanking SalI restriction sites to allow cloning of the ORF into the pQE-30 expression vector. The oligonucleotides (SEQ ID NOs.:66 and 67) were used to amplify PMPE-specific PCR products from *C. trachomatis* L2 serovar, genomic DNA.

The sequence of the amplification primers for SEQ ID NO.:66 (forward primer) and SEQ ID NO.:67 (reverse primer) used for these PCR reactions are shown below.

```
Forward primer for PMPE
                                        (SEQ ID NO.: 66.)
5'- ATC CAG CAG AG GGT CGA CGG GTT CCA GAT CCT ACG
AAA GAG TCG CTA TC- 3'

Reverse primer for PMPE
                                        (SEQ ID NO.: 67)
5'- ATC CAG CAG AGG GTC GAC GGC C TTA GAA TCG CAG
AGC AAT TTC CCC ATT GA- 3'
```

In addition to the PMPE coding sequences, a TAA (TAA in reverse complement) stop codon was engineered into the reverse primer immediately after the last PMPE codon to end protein synthesis. A SalI restriction site was engineered into the reverse primer downstream and adjacent to the TAA stop codon to facilitate cloning into pQE-30.

Standard PCR amplification reactions (2 mM $Mg^{2+}$, 200 μmol dNTPs, 0.75 units AmpliTaq, 50 l final volume) were programmed using ~0.1 μg of *C. trachomatis* L2 chromosomal DNA. Amplification of the PMPE target sequence was achieved using a standard 32-cycle, three-step thermal profile, i.e., 95° C., 30 sec; 55° C., 45 sec; 72° C., 3 min. Amplification was carried out in 0.2 ml polypropylene thin-walled PCR tubes (Perkin-Elmer) in a Perkin-Elmer model 2400 thermal cycler. PCR amplification reactions produced the expected PMPE-specific ~3.0 Kbp amplimer.

The ~3.0 Kbp PMPE amplimer was purified from unincorporated primers using hydroxyapatite spin columns (QiaGen) and digested to completion with an excess of SalI (BRL, ~10 units per 1 μg DNA) according to the manufacturers recommendations. The purified and digested PMPE ORF was then purified via QiaGen columns as described above and cloned into plasmid pQE-30 that had been previously digested to completion with SalI and treated with calf intestinal alkaline phosphatase (BRL, ~0.05 units/pmole of 5' ends) to prevent vector religation (~5:1, insert:vector ratio).

Digestion of the pQE-30 vector with SalI produces a single restriction fragment of ~3.4 Kbp.

Aliquots from the ligation reaction were then used to electrotransform a suitable *E. coli* host (e.g., M15 (pREP)). Transformed cells were plated on 2X-YT agar containing 100 μg/ml ampicillin (for pQE-30) and 40 μg/ml kanamycin (for pREP) grown at 37° C. for ~12-16 hours. Mini-prep DNA from ampicillin/kanamycin-resistant transformants picked at random were prepared using commercially available reagents (QiaGen Mini Prep Kit) and examined for the presence of recombinant plasmids larger than the pQE-30 plasmid (i.e., insert-carrying plasmids). Putative PMPE-insert carrying recombinant plasmids were then digested to completion with SalI and examined for the presence of the PMP-specific fragment by standard agarose gel electrophoresis (0.8% agarose, TAE buffer). All plasmids tested were found to contain the PMPE insert. Plasmid M15 pREP (pQE-pmpE-CT)#37 was one recombinant derivative isolated by these procedures.

6.12. PCR Cloning of the PMPI ORF

To produce high levels of recombinant PMPI protein for immunogenicity and protective efficacy studies, the PMPI ORF was PCR cloned into an *E. coli* high expression vector pBAD/Thio-E (Invitrogen) under the control of the araBAD promoter. Oligonucleotide PCR primers complementary to the DNA sequences encoding the first 10 amino acid residues of the N-terminus and the last 8 C-terminal amino acid residues of the *C. trachomatis* L2 PMPI ORF present in the UC Berkeley genomic database (see Stephens et al., 1998, Science: 282: 754-759 and GenBank Accession No. NC000117) were synthesized. In addition to the PMPI specific sequences, the 5' forward PCR primer contained the sequence 5' AGG CAG AGG CAT-3' (SEQ ID NO.:68) immediately upstream of the PMPI ATG start codon while the 3' reverse primer contained the sequence 5'-AGG CAG AGG GTC GAC'3' (SEQ ID NO.:70) immediately downstream of the C-terminal GAA codon. The oligonucleotides (SEQ ID NO.:69 and 70) were used to amplify PMPI-specific PCR products from *C. trachomatis* L2 genomic DNA. The sequence of the amplification primers for SEQ ID NO.:69 (forward primer) and SEQ ID NO.:70 (reverse primer) used for these PCR reactions are shown below.

```
Forward primer PMPI
                                        (SEQ ID NO.: 69)
5'- AGG CAG AGG CAT ATG CGA CCT GAT CAC ATG AAC
TTC TGT TG- 3'

Reverse primer PMPI
                                        (SEQ ID NO.: 70)
5'-AGG CAG AGG GTC GAC GAA CCT GTA AGT GGT CCC CAG
ATC -3'
```

Standard PCR amplification reactions (2 mM $Mg^{2+}$, 200 μmol dNTPs, 0.75 units AmpliTaq, 50 l final volume) were programmed using ~0.1 μg of *C. trachomatis* L2 chromosomal DNA. Amplification of the PMPI target sequence was achieved using a standard 32-cycle, three-step thermal profile, i.e., 95° C., 30 sec.; 55° C., 45 sec.; 72° C., 3 min. Amplification was carried out in 0.2 ml polypropylene thin-walled PCR tubes (Perkin-Elmer) in a Perkin-Elmer model 2400 thermal cycler. PCR amplification reactions produced the expected PMPI-specific ~3.0 Kbp amplimer.

The ~3.0 Kbp PMPI amplimer was purified from unincorporated primers using hydroxyapatite spin columns (QiaGen). The purified PMPI ORF was then cloned into the T/A PCR product cloning vector pUni/V5-HIS-TOPO plasmid (Invitrogen) using standard TOPO cloning methods described by the manufacturer. The plasmid pUni/V5-His-TOPO carries a loxP site upstream of the T/A cloning site that can be used to recombine insert carrying plasmids with other loxP-containing plasmids for subsequent controlled expression of recombinant protein.

Aliquots from the PMPI amplimer and pUni/V5-His-TOPO ligation reaction were then used to transform a suitable *E. coli* host (e.g., PIR1). Transformed cells were plated on 2X-YT agar containing 40 μg/ml kanamycin and grown at 37° C. for ~12-16 hours. Mini-prep DNA from kanamycin-resistant transformants picked at random were prepared using commercially available reagents (QiaGen Mini Prep Kit) and examined for the presence of recombinant plasmids larger than the ~2.2 Kbp vector plasmid Uni/V5-His-TOPO (i.e., insert-carrying plasmids). pUni/V5-His-TOPO plasmids carrying the cloned PMPI ORF were mixed (~100 ng) with the plasmid pBAD/Thio-E (~100 ng) in the presence of a recombination buffer supplied by the manufacturer and the two were recombined into a single molecule by homologous recombination at the lox sites on both the pUni/V5-His-TOPO-PMPI plasmid and pBAD/Thio-E vector catalyzed by the Cre recombinase. pBAD/Thio-E carries a segment of the *E. coli* thioredoxin protein (~12 kD) that has been mutated to encode an N-terminal (His) affinity chromatography domain. A single loxP recombination site is also encoded by pBAD/Thio-E immediately downstream of the His-Thio redoxin coding sequence. The His-Thioredoxin coding sequence and the loxP site are themselves downstream of the araBAD promoter. Recombining pBAD/Thio-E with PMPI derivatives of pUni/V5-His-TOPO through the loxP sites using the loxP-specific Cre recombinase results in the formation of a chimeric protein with the His-thioredoxin domain at the N-terminus which is fused in frame to the PMPI ORF. Following recombination the chimeric plasmids were transformed into *E. coli* TOP10 cells. Transformed cells were selected on plates containing 40 μg/ml kanamycin. All ~9.5 kBp plasmids tested were found to contain the PMPI insert. Plasmid TOP10 (pBAD-PmpI-Ct-Uni)#7 was one recombinant derivative isolated by these procedures.

6.13. Expression of Recombinant PMPE

One milliliter of a frozen stock of *E. coli* strain M15 pREP containing plasmid (pQE-pmpE-CT)#37 was used to inoculate ~100 ml of 2X-YT broth containing 40 μg/ml kanamycin and 100 μg/ml ampicillin and grown overnight at 30° C. to prepare a fermentor seed culture. Approximately 20 ml of the overnight seed culture was then used to inoculate a New Brunswick Bioflow 3000 fermentor loaded with ~2.0 L of 2X-YT broth containing 40 μg/ml kanamycin and 100 μg/ml ampicillin. The culture was grown at 37° C. with vigorous aeration until an $O.D._{600}$ value of −1.0 was attained. Expression of rPMPE was induced by adding IPTG to a 1.0 mM final concentration and continuing fermentation. Incubation in the presence of IPTG was continued for approximately 4-5 hours.

At the end of the induction period, the *E. coli* culture, with some cells displaying classic recombinant protein inclusion bodies, was harvested by continuous flow centrifugation using an Heraeus Contifuge 28RS centrifuge. Following centrifugation, cell mass was scraped from the centrifuge bowl and stored at −70° C. until processed.

Approximately 15 gm of the M15 pREP (pQE-pmpE-CT) #37 frozen cell paste was resuspended by vortexing and trituration in ~40 ml of ice cold 10 mM sodium phosphate buffer, pH 7.3. Once suspended, lysozyme (Chicken egg white, Sigma) and DNase I (Bovine pancreas, Sigma) were added to final concentrations of 1.0 mg/ml and 0.01 mg/ml, respectively, and the mixture incubated on ice for 30-45 minutes. Cells were disrupted by 2 sequential passes through a pre-cooled (~4° C.) SLM Aminco French Pressure Cell (~14 Kpsi, 1"-diameter bore). The cell lysate was then centrifuged for 5 min at ~500×g (4° C.) in a Sorvall SS34 rotor to remove unbroken cells. Insoluble material containing the rPMPE was isolated (pelleted) by centrifugation for 45 minutes at ~20,000×g (4° C.) in a Sorvall SS34 rotor. The supernatant from this centrifugation was discarded and the insoluble fraction stored at −20° C. in pellet form.

To selectively extract contaminating proteins and remove endotoxin, the rPMPE-containing insoluble pellet was thawed on ice and washed twice with 10 ml of PBS buffer containing 2.0% Triton X-100. Washing was performed at room temperature and suspension of the gelatinous rPMPE-containing pellet was accomplished by vortexing and homogenization in a conventional glass tissue grinder. Insoluble material containing the rPMPE was recovered after washing by centrifugation at ~10,000×g for 20 minutes (room temperature) in a Sorvall SS34 rotor. Insoluble material was then washed (again by vortexing and homogenization) 2 times with 10 ml of a 4.0 M urea solution containing 2.0 M NaCl. Washed rPMPE material was recovered by centrifugation as above. The insoluble rPMPE fraction was further washed 2 times with 10 ml of a PBS solution containing 1.0% Zwittergent 3-14 (Sigma).

The rPMPE pellet recovered after centrifugation of the final wash solution was then solubilized for 2 hours at room temperature in standard Laemelli SDS-PAGE sample buffer containing 4 M urea. Solubilized rPMPE was size fractionated into a single protein band of ~105 kDa by electrophoresis through a cylinderical ~37 mm×~12 cm 6% polyacrylamide (36:1, acrylamide:bis-acrylamide) Tris/glycine/SDS preparative gel. A 4% polyacrylamide stacking gel was formed on top of the resolving gel (~37 mm×~3 cm). Electrophoresis was carried out on a BioRad model 491 PrepCell unit for ~12 hours at ~22° C. (12 watts constant wattage) using a conventional Tris/glycine/SDS running buffer (BioRad). As electrophoresis proceeded, size fractionated proteins eluting from the bottom of the PrepCell were pumped to an Amersham fraction collector where ~8.0 ml fractions were collected.

Aliquots (~20 μl) from each fraction were mixed with an equal volume of 2× LSB heated to ~100° C. for 3 minutes and electrophoresed on a 4-20% SDS-PAG to identify fractions containing the PMPE protein. Prestained molecular weight standards were loaded into a parallel lane and were used as a size gauge. PMPE-containing factors were pooled and excess SDS detergent was removed by diluting the eluted sample with approximately 20 volumes of sterile, endotoxin-free 10 mM sodium phosphate buffer (pH 7.4) and concentrated to approximately 1.0 mg/ml by ultrafiltration in an Amicon stirred concentration cell using a YM30 ultrafiltration membrane.

Residual endotoxin was removed from the concentrated rPMPE solution by polymyxin B Affi-Prep Polymyxin Matrix (BioRad) treatment. Affi-Prep treatment was performed overnight at 4° C. in a batch mode according to the manufacturers recommendations.

The protein concentration of the concentrated, polymyxin B-treated rPMPE was determined using the Micro BCA method (Pierce Chem.) and BSA as a standard.

Purified rPMPE (~0.9-1.2 mg/ml protein concentration) was evaluated for purity, identity, and residual endotoxin burden by SDS-PAGE, Western blot, and a colorimetric endotoxin assay (BioWhittaker), respectively. The gel-purified rPMPE material displayed a purity of >95% as a single band of the expected molecular size by gel analysis. Residual endotoxin is calculated to be ≦0.05 EU/g.

6.14. Expression of Recombinant PMPI

One milliliter of a frozen stock of *E. coli* strain TOP10 containing plasmid (pBAD-pmpI-Ct-Uni)#7 was used to inoculate ~100 ml of 2X-YT broth containing 40 μg/ml kanamycin and grown overnight at 37° C. to prepare a fermenter seed culture. Approximately 20 ml of the overnight seed culture was then used to inoculate a New Brunswick Bioflow 3000 fermenter loaded with ~2.0 L of 2X-YT broth containing 40 μg/ml kanamycin. The culture was grown at 37° C. with vigorous aeration until an $O.D._{600}$ value of C1.0 was attained. Expression of rPMPI was induced by addition of arabinose to a final concentration of 1.0 mM and continuing cultivation for approximately 4-5 hours.

At the end of the induction period, the *E. coli* culture, with some cells displaying classic recombinant protein inclusion bodies, was harvested by continuous flow centrifugation using an Heraeus Contifuge 28RS centrifuge. Following centrifugation, cell mass was scraped from the centrifuge bowl and stored at −70° C. until processed.

Approximately 15 gm of the TOP10 (pBAD-pmpI-Ct-Uni) #7 frozen cell paste was resuspended by vortexing and trituration in ~40 ml of ice cold 10 mM sodium phosphate buffer, pH 7.3. Once suspended, lysozyme (Chicken egg white, Sigma) and DNAase I (Bovine pancreas, Sigma) were added to final concentrations of 1.0 mg/ml and 0.01 mg/ml, respectively, and the mixture incubated on ice for 30-45 minutes. Cells were disrupted by 2 sequential passes through a pre-cooled (~4° C.) SLM Aminco French Pressure Cell (~14 Kpsi, 1" diameter bore). The cell lysate was then centrifuged for 5 min at ~500×g (4° C.) in a Sorvall SS34 rotor to remove unbroken cells. Insoluble material containing the rPMPI was isolated (pelleted) by centrifugation for 45 min at ~20,000×g (4° C.) in a Sorvall SS34 rotor. The supernatant from this centrifugation was discarded and the insoluble fraction stored at −20° C. in pellet form.

To selectively extract contaminating proteins and remove endotoxin, the rPMPI-containing insoluble pellet was thawed on ice and washed twice with 10 ml of PBS buffer containing 2.0% Triton X-100. Washing was performed at room temperature and suspension of the gelatinous rPMPI-containing pellet was accomplished by vortexing and homogenization in a conventional glass tissue grinder. Insoluble material containing the rPMPI was recovered after washing by centrifugation at ~10,000×g for 20 minutes (room temperature) in a Sorvall SS34 rotor. Insoluble material was then washed (again by vortexing and homogenization) 2 times with 10 ml of a 4.0 M urea solution containing 2.0 M NaCl. Washed rPMPI material was recovered by centrifugation as above. The insoluble rPMPI fraction was further washed 2 times with 10 ml of a PBS solution containing 1.0% Zwittergent 3-14 (Sigma).

The rPMPI pellet recovered after centrifugation of the final wash solution was then solubilized for 2 hours at room temperature in standard Laemelli SDS-PAGE sample buffer containing 4 M urea. Solubilized rPMPI-thiroredoxin-fusion protein was size fractionated into a single protein band of ~105 kDa using a model 491 PrepCell (BioRad) cylindrical gel as described above for PMPE above. PMPI was obtained from SDS PAG and residual endotoxin removed as described for PMPE above.

The protein concentration of the concentrated, polymyxin B-treated rPMPI-thioredoxin fusion protein was determined using the Micro BCA method (Pierce Chem.) and BSA as a standard.

Purified rPMPI (~0.9-1.2 mg/ml protein concentration) was evaluated for purity, identity, and residual endotoxin burden by SDS-PAGE, Western blot, and a colorimetric endotoxin assay (BioWhittaker), respectively. The gel-purified rPMPI material displayed a purity of >95% as a single band of the expected molecular size by gel analysis. Residual endotoxin is calculated to be ≦0.05 EU/g 6.15. Affinity Chromatography Purification of Recombinant Protein Recombinant PMPE or PMPI protein is purified to apparent homogeneity using standard preparative immobilized metal affinity chromatography (MAC) procedures. Briefly, an *E. coli* strain harboring an expression plasmid containing PMPE or PMPI protein gene is grown in Luria broth in a 5 L fermenter (New Brunswick) at 37° C. with moderate aeration until mid-log phase (~0.5 O.D.$_{600}$) and induced with IPTG or arabinose (1 mM final) for 4-5 hours. Cell paste is collected, washed in PBS and stored at −20° C. Aliquots of frozen cell paste (~9-10 grams wet weight) are suspended in ~120 ml of D-PBS by mechanical agitation and lysed by passage through a French pressure cell (2×, 14,000 psi, 4° C.). Soluble protein is then removed from rPMPE or rPMPI protein inclusion bodies by high speed centrifugation (~20,000×g, 4° C., 30 min).

The insoluble pellet containing rPMPE or rPMPI protein is suspended in ~20 ml of ice cold D-PBS by homogenization and centrifuged as above. Washed rPMPE or rPMPI protein inclusion bodies are then denatured by suspension in a sodium phosphate buffer (0.1 M, pH 7.0) containing 7.4 M guanidine hydrochloride, 5% 2-ME and 10% glycerol and loaded onto a $Ni^{2+}$-affinity column (1.5 cm×25 cm, bed volume ~30 ml) prepared from Fast-Flow Chelating Sepharose (Pharmacia) and charged with $Ni^{2+}$ or $Zn^{2+}$ ions by standard procedures. Unbound material is removed by washing the column with ~5-10 column volumes of a sodium phosphate buffer (0.1 M, pH 7.0) containing ~7.4 M guanidine HCl.

Recombinant PMPE or PMPI protein bound to the affinity resin by virtue of the $(His)_6$ affinity purification domain is eluted using sodium phosphate buffer (pH 7.4) containing 7.4 M guanidine HCl and 200 mM imidazole. Eluted material is dialyzed against TE buffer containing SDS (0.5%) to remove the guanidine. Dialyzed material is concentrated using a Amicon stirred cell concentrator using a YM30 membrane and mixed with a ⅕ volume of 5×SDS gel sample buffer containing 1 mM 2-mercaptoethanol and boiled at 100° C. for 5 minutes.

Samples are loaded onto Tris/glycine acrylamide gels (4% stacking gel, 4-20% resolving gel, 30:0.8 acrylamide:bis solution, 1 mm thickness). A prestained molecular weight standard (See Blue or Multimark, Novex) is run in parallel with the rPMPE or rPMPI protein samples to identify size fractions on the gel. The purity of rPMPE or rPMPI protein is determined using conventional SDS-PAGE and commercially available silver staining reagents (Silver Stain Plus, Novex).

6.16. Generation of a Radiolabeled Screening Probe

The sequence information shown above is used to design a pair of nondegenerate oligonucleotide primers. PCR amplification of DNA fragments is performed under the same conditions as described above with the exception that the annealing temperature is lowered to 50° C. The DNA fragment is isolated from an agarose gel as before and radiolabeled using [$^{32}$P]-gamma-ATP and T4 polynucleotide kinase according to standard methods. Unincorporated radiolabel is separated from the probe on a G25 Sepharose spin column. Before use, the probe is denatured for 2 min. at 95° C. and subsequently chilled on ice (4° C.).

6.17. Hybridization of Plaque-Lift Filters and Southern Blots with Radiolabeled Probe Phage plaques from library platings are immobilized on nylon filters using standard transfer protocols well known to those skilled in the art. Digested bacterial genomic DNA, phage or plasmid DNA is electrophoresed on 0.8% TAE-agarose gels and transferred onto nylon filters using a pressure blotter (Stratagene) according to the manufacturer's recommendations. Hybridizations with selected probes are performed at 37° C. (for example, to detect PMP homologs of other species). Hybridizations with specific probes are generally carried out at 50-60° C. (e.g., to detect the identical sequence or the analogous protein in another serovar). Washes of increasing stringency are done at the respective hybridization temperatures until nonspecific background is minimized.

6.18. Construction of a *Chlamydia* Genomic DNA Library

A genomic library was constructed in the λZAPII replacement vector obtained from Stratagene. The vector arms were digested with EcoR1. Digests of *Chlamydia* DNA by EcoR1 were performed to yield fragment sizes between 1 kb and 5 kb. Ligations of vector arms and insert DNA were carried out according to standard protocols. Ligation reactions were packaged in vitro using the Stratagene GigaPack Gold III extract. The packaged phage were plated on *E. coli* X1 Blue MRA (P2) (Stratagene). An initial library titer was determined and expressed as number of pfu.

The library is screened using $4\times10^4$ pfu that are plated at a density of $8\times10^3$ pfu/130 mm plate with a PMPE or PMPI specific, probe. Several putative positive phage plaques are located and the strongest hybridizing phage are eluted from cored agarose plugs, titered and replated for secondary screening. The selected phage are replated at low density (approximately 100 pfu/plate) and plaques are analyzed by PCR using primer pairs. Inserts carrying plasmids (phagemids) are rescued from the selected phage by co-infecting *E. coli* cells with an appropriate helper virus.

6.19. Determination of Insert Size and Mapping of DNA Fragments

In order to estimate the size of inserts, phagemid DNA is digested with appropriate restriction enzymes (e.g., NotI) and the digests are analyzed on a 0.5% TAE-agarose gel side by side with suitable DNA markers. In order to map restriction fragments that would hybridize to the probe, DNA from phagemid isolates is digested with a number of common restriction enzymes either alone or in combination with NotI. The rationale of this approach is to discriminate between fragments that span the insert/phagemid vector junction and those that map on the NotI insert. The series of single and double digests are run side-by-side for each phage isolate and analyzed by Southern analysis with radiolabeled probe.

6.20. Sequencing of the PMPE and PMPI Gene

Sequencing of the PMPE and PMPI gene is performed using the Dye Terminator Cycle Sequencing Kit from Perkin-Elmer according to the manufacturer's specifications. The sequencing reactions are read using an ABI Prism 310 Genetic Analyzer. The sequences are aligned using the AutoAssembler software (Perkin-Elmer) provided with the ABI Prism 310 sequencer.

The sequence of the nucleic acid encoding the PMPE protein and the deduced amino acid sequence of the PMPE expressed by Plasmid M15 pREP (pQE-pmpE-Ct-Uni)#37 are shown in FIG. 8 (SEQ ID Nos.:72 and 73).

6.21. In Vivo Efficacy of PMPE

The ability of PMPE to protect female C3HeOUJ mice using the procedure disclosed in Section 6.9.2, supra, is shown in Table 4. Groups of mice were immunized intranasally (i.n.) with 10 μg PMPE (with or without ~5 μg mLT as an adjuvant) prior to challenge with live *C. trachomatis* serovar F. Negative control mice were immunized with ~5 μg mLT intranasally prior to administration of live *C. trachomatis*. Positive control groups were immunized with adjuvant alone intranasally but were not administered live *C. trachomatis*. The fertility rate for mice vaccinated with PMPE or PMPE and mLT was 50% and 46% respectively. The fertility rate for negative control mice inunized with adjuvant alone (mLT) was 9% and the fertility of positive control mice not infected with *C. trachomatis* but administered mLT was 95%. These results demonstrate that PMPE is an effective vaccine for ameliorating infertility induced by infection with *C. trachomatis*. Thus, one with skill would in light of teaching of the specification be able to make the claimed PMPE polypeptides and determine if the PMPE polypeptides have the ability to ameliorate disease associated with infection with *C. trachomatis*.

TABLE 4

FERTILITY ASSESSMENT FOR PMPE

| Group | Vaccine and Route | % Fertility |
|---|---|---|
| I | PMPE + mLT/i.n. | 50 |
| II | PMPE/i.n. | 46 |
| III | mLT/i.n.(Neg. control) | 9 |
| IV | mLT/i.n. (Pos. control) | 95 |

The present invention is not to be limited in scope by the microorganism deposited or the specific embodiments described herein. It will be understood that variations which are functionally equivalent are within the scope of this invention. Indeed, various modifications of the invention, in addition to those shown and described herein, will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. An isolated polynucleotide comprising the nucleic acid sequence which encodes a polypeptide comprising the amino acid sequence selected from the group consisting of:

(a) amino acids 32-965 of SEQ ID NO: 2;

(b) SEQ ID NO: 2;

(c) amino acids 590-625 of SEQ ID NO: 2;

(d) amino acids 1-500 of SEQ ID NO: 2;

(e) amino acids 625-700 of SEQ ID NO: 2;

(f) the amino acid sequence encoded by the *Chlamydia* insert in *E. coli* M15 assigned as ATCC PTA No. 2462; and (g) a combination of two or more amino acid sequences of (a)-(f).

2. The polynucleotide of claim 1, wherein said polypeptide further comprises a heterologous polypeptide.

3. The polynucleotide of claim 2, wherein said heterologous polypeptide is selected from the group consisting of a pre- and/or pro-sequence, an affinity purification sequence, and an immunogenic sequence.

4. The polynucleotide of claim 2, wherein said heterologous polypeptide is selected from the group consisting of SEQ ID NO: 4; amino acids 13-40 of SEQ ID NO: 4; amino acids 70-110 of SEQ ID NO: 4; amino acids 150-225 of SEQ ID NO: 4; amino acids 250-290 of SEQ ID NO: 4; amino acids 370-455 of SEQ ID NO: 4; amino acids 400-455 of SEQ ID NO: 4; amino acids 470-520 of SEQ ID NO: 4; amino acids 615-670 of SEQ ID NO: 4; amino acids 710-775 of SEQ ID NO: 4; amino acids 765-825 of SEQ ID NO: 4; amino acids 830-860 of SEQ ID NO: 4; amino acids 1-500 of SEQ ID NO: 4; and the amino acid sequence encoded by the *Chlamydia* insert in *E. coli* TOP10 assigned as ATCC PTA No. 2461.

5. The polynucleotide of claim 1, wherein said nucleic acid sequence is selected from the group consisting of:

(a) nucleotides 94-2895 of SEQ ID NO: 1;

(b) SEQ ID NO: 1;

(c) the *Chlamydia* insert in *E. coli* M15 assigned as ATCC PTA No. 2462; and (d) a combination of (a), (b), or (c), or the complement thereof.

6. A vector comprising the polynucleotide of claim 1.

7. A host cell comprising the vector of claim 6.

8. A composition comprising the polynucleotide of claim 1 and a carrier.

9. The composition of claim 8, further comprising an adjuvant.

10. An isolated polynucleotide comprising the nucleic acid sequence, which encodes a polypeptide comprising the amino acid sequence of SEQ ID NO: 4 or the amino acid sequence encoded by the *Chlamydia* insert in *E. coli* TOP10 assigned as ATCC PTA No. 2461.

11. The polynucleotide of claim 10, wherein said polypeptide further comprises a heterologous polypeptide.

12. The polynucleotide of claim 11, wherein said heterologous polypeptide is selected from the group consisting of a pre- and/or pro-sequence, an affinity purification sequence, and an immunogenic sequence.

13. The polynucleotide of claim 11, wherein said heterologous polypeptide is selected from the group consisting of SEQ ID NO: 2; amino acids 32-965 of SEQ ID NO: 2; amino acids 15-56 of SEQ ID NO: 2; amino acids 15-121 of SEQ ID NO: 2; amino acids 45-125 of SEQ ID NO: 2; amino acids 125-190 of SEQ ID NO: 2; amino acids 195-261 of SEQ ID NO: 2; amino acids 275-366 of SEQ ID NO: 2; amino acids 375-440 of SEQ ID NO: 2; amino acids 440-490 of SEQ ID NO: 2; amino acids 525-590 of SEQ ID NO: 2; amino acids 590-625 of SEQ ID NO: 2; amino acids 615-650 of SEQ ID NO: 2; amino acids 625-700 of SEQ ID NO: 2; amino acids 725-800 of SEQ ID NO: 2; amino acids 755-775 of SEQ ID NO: 2; amino acids 785-845 of SEQ ID NO: 2; amino acids 815-865 of SEQ ID NO: 2; amino acids 1-31 of SEQ ID NO: 2; amino acids 1-500 of SEQ ID NO: 2; and the amino acid sequence encoded by the *Chlamydia* insert in *E. coli* M15 assigned as ATCC PTA No. 2462.

14. The polynucleotide of claim 10, wherein said nucleic acid sequence is SEQ ID NO:3 or the *Chlamydia* insert in *E. coli* TOP10 assigned as ATCC PTA No. 2461.

15. A vector comprising the polynucleotide of claim 10.

16. A host cell comprising the vector of claim 15.

17. A composition comprising the polynucleotide of claim 10 and a carrier.

18. The composition of claim 17, further comprising an adjuvant.

19. An isolated polynucleotide encoding a polypeptide, which consists of the amino acid sequence selected from the group consisting of: amino acids 32-965 of SEQ ID NO: 2; SEQ ID NO: 2; the amino acid sequence encoded by the *Chlamydia* insert in *E. coli* M15 assigned as ATCC PTA No. 2462; amino acids 15-56 of SEQ ID NO: 2; amino acids 15-121 of SEQ ID NO: 2; amino acids 45-125 of SEQ ID NO: 2; amino acids 125-190 of SEQ ID NO: 2; amino acids 195-261 of SEQ ID NO: 2; amino acids 275-366 of SEQ ID NO: 2; amino acids 375-440 of SEQ ID NO: 2; amino acids 440-490 of SEQ ID NO: 2; amino acids 525-590 of SEQ ID NO: 2; amino acids 590-625 of SEQ ID NO: 2; amino acids 615-650 of SEQ ID NO: 2; amino acids 625-700 of SEQ ID NO: 2; amino acids 725-800 of SEQ ID NO: 2; amino acids 755-775 of SEQ ID NO: 2; amino acids 785-845 of SEQ ID NO: 2; amino acids 815-865 of SEQ ID NO: 2; amino acids 1-31 of SEQ ID NO: 2; and amino acids 1-500 of SEQ ID NO: 2.

20. A vector comprising the polynucleotide of claim 19.

21. A host cell comprising the vector of claim 20.

22. A composition comprising the polynucleotide of claim 19 and a cattier.

23. The composition of claim 22, further comprising an adjuvant.

24. The composition of claim 22, further comprising a heterologous polynucleotide.

25. The composition of claim 24, wherein said heterologous polynucleotide encodes the amino acid sequence, which is selected from the group consisting of SEQ ID NO: 4; amino acids 13-40 of SEQ ID NO: 4; amino acids 70-110 of SEQ ID NO: 4; amino acids 150-225 of SEQ ID NO: 4; amino acids 250-290 of SEQ ID NO: 4; amino acids 370-455 of SEQ ID NO: 4; amino acids 400-455 of SEQ ID NO: 4; amino acids 470-520 of SEQ ID NO: 4; amino acids 615-670 of SEQ ID NO: 4; amino acids 710-775 of SEQ ID NO: 4; amino acids 765-825 of SEQ ID NO: 4; amino acids 830-860 of SEQ ID NO: 4; amino acids 1-500 of SEQ ID NO: 4; and the amino acid sequence encoded by the *Chlamydia* insert in *E. coli* TOP10 assigned as ATCC PTA No. 2461.

26. An isolated polynucleotide encoding a polypeptide, which consists of the amino acid sequence selected from the group consisting of: SEQ ID NO: 4; amino acids 13-40 of SEQ ID NO: 4; amino acids 70-110 of SEQ ID NO: 4; amino acids 150-225 of SEQ ID NO: 4; amino acids 250-290 of SEQ ID NO: 4; amino acids 370-455 of SEQ ID NO: 4; amino acids 400-455 of SEQ ID NO: 4; amino acids 470-520 of SEQ ID NO: 4; amino acids 615-670 of SEQ ID NO: 4; amino acids 710-775 of SEQ ID NO: 4; amino acids 765-825 of SEQ ID NO: 4; amino acids 830-860 of SEQ ID NO: 4; and amino acids 1-500 of SEQ ID NO: 4.

27. A vector comprising the polynucleotide of claim 26.

28. A host cell comprising the vector of claim 27.

29. A composition comprising the polynucleotide of claim 26 and a carrier.

30. The composition of claim 29, further comprising an adjuvant.

31. The composition of claim 29, further comprising a heterologous polynucleotide.

32. The composition of claim 31, wherein said heterologous polynucleotide encodes the amino acid sequence, which is selected from the group consisting of SEQ ID NO: 2; amino acids 15-56 of SEQ ID NO: 2; amino acids 15-121 of SEQ ID NO: 2; amino acids 45-125 of SEQ ID NO: 2; amino acids 125-190 of SEQ ID NO: 2; amino acids 195-261 of SEQ ID NO: 2; amino acids 275-366 of SEQ ID NO: 2; amino acids 375-440 of SEQ ID NO: 2; amino acids 440-490 of SEQ ID NO: 2; amino acids 525-590 of SEQ ID NO: 2; amino acids 590-625 of SEQ ID NO: 2; amino acids 615-650 of SEQ ID NO: 2; amino acids 625-700 of SEQ ID NO: 2; amino acids 725-800 of SEQ ID NO: 2; amino acids 755-775 of SEQ ID NO: 2; amino acids 785-845 of SEQ ID NO: 2; amino acids 815-865 of SEQ ID NO: 2; amino acids 1-31 of SEQ ID NO: 2; amino acids 1-500 of SEQ ID NO: 2; and the amino acid sequence encoded by the *Chlamydia* insert in *E. coli* M15 assigned as ATCC PTA No. 2462.

33. An isolated polynucleotide comprising a nucleotide sequence, which encodes a polypeptide comprising the amino acid sequence selected from the group consisting of: amino acids 32-965 of SEQ ID NO: 2; SEQ ID NO: 2; the amino acid sequence encoded by the *Chlamydia* insert in *E. coli* M15 assigned as ATCC PTA No. 2462; amino acids 15-56 of SEQ ID NO: 2; amino acids 15-121 of SEQ ID NO: 2; amino acids 45-125 of SEQ ID NO: 2; amino acids 125-190 of SEQ ID NO: 2; amino acids 195-261 of SEQ ID NO: 2; amino acids 275-366 of SEQ ID NO: 2; amino acids 375-440 of SEQ ID NO: 2; amino acids 440-490 of SEQ ID NO: 2; amino acids 525-590 of SEQ ID NO: 2; amino acids 590-625 of SEQ ID NO: 2; amino acids 615-650 of SEQ ID NO: 2; amino acids 625-700 of SEQ ID NO: 2; amino acids 725-800 of SEQ ID NO: 2; amino acids 755-775 of SEQ ID NO: 2; amino acids 785-845 of SEQ ID NO: 2; amino acids 815-865 of SEQ ID NO: 2; amino acids 1-31 of SEQ ID NO: 2; and amino acids 1-500 of SEQ ID NO: 2, wherein said polypeptide further comprises a heterologous polypeptide.

34. The polynucleotide of claim 33, wherein said heterologous polypeptide is selected from the group consisting of a pre- and/or pro-sequence, an affinity purification sequence, and an immunogenic sequence.

35. The polynucleotide of claim 33, wherein said heterologous polypeptide comprises the amino acid sequence selected from the group consisting of SEQ ID NO: 4; amino acids 13-40 of SEQ ID NO: 4; amino acids 70-110 of SEQ ID NO: 4; amino acids 150-225 of SEQ ID NO: 4; amino acids 250-290 of SEQ ID NO: 4; amino acids 370-455 of SEQ ID NO: 4; amino acids 400-455 of SEQ ID NO: 4; amino acids 470-520 of SEQ ID NO: 4; amino acids 615-670 of SEQ ID NO: 4; amino acids 710-775 of SEQ ID NO: 4; amino acids 765-825 of SEQ ID NO: 4; amino acids 830-860 of SEQ ID NO: 4; amino acids 1-500 of SEQ ID NO: 4; and the amino acid sequence encoded by the *Chlamydia* insert in *E. coli* TOP10 assigned as ATCC PTA No. 2461.

36. A vector comprising the polynucleotide of claim 33.

37. A host cell comprising the vector of claim 36.

38. A composition comprising the polynucleotide of claim 33 and a carrier.

39. An isolated polynucleotide comprising a nucleotide sequence, which encodes a polypeptide comprising the amino acid sequence selected from the group consisting of: amino acids 13-40 of SEQ ID NO: 4; amino acids 70-110 of SEQ ID NO: 4; amino acids 150-225 of SEQ ID NO: 4; amino acids 250-290 of SEQ ID NO: 4; amino acids 370-455 of SEQ ID NO: 4; amino acids 400-455 of SEQ ID NO: 4; amino acids 470-520 of SEQ ID NO: 4; amino acids 615-670 of SEQ ID NO: 4; amino acids 710-775 of SEQ ID NO: 4; amino acids 765-825 of SEQ ID NO: 4; amino acids 830-860 of SEQ ID NO: 4; and amino acids 1-500 of SEQ ID NO: 4, wherein said polypeptide further comprises a heterologous polypeptide.

40. The polynucleotide of claim 39, wherein said heterologous polypeptide is selected from the group consisting of a pre- and/or pro-sequence, an affinity purification sequence, and an immunogenic sequence.

41. The polynucleotide of claim 39, wherein said heterologous polypeptide comprises the amino acid sequence selected from the group consisting of SEQ ID NO: 2; amino acids 15-56 of SEQ ID NO: 2; amino acids 15-121 of SEQ ID NO: 2; amino acids 45-125 of SEQ ID NO: 2; amino acids 125-190 of SEQ ID NO: 2; amino acids 195-261 of SEQ ID NO: 2; amino acids 275-366 of SEQ ID NO: 2; amino acids 375-440 of SEQ ID NO: 2; amino acids 440-490 of SEQ ID NO: 2; amino acids 525-590 of SEQ ID NO: 2; amino acids 590-625 of SEQ ID NO: 2; amino acids 615-650 of SEQ ID NO: 2; amino acids 625-700 of SEQ ID NO: 2; amino acids 725-800 of SEQ ID NO: 2; amino acids 755-775 of SEQ ID NO: 2; amino acids 785-845 of SEQ ID NO: 2; amino acids 815-865 of SEQ ID NO: 2; amino acids 1-31 of SEQ ID NO: 2; amino acids 1-500 of SEQ ID NO: 2; and the amino acid sequence encoded by the *Chlamydia* insert in *E. coli* M15 assigned as ATCC PTA No. 2462.

42. A vector comprising the polynucleotide of claim 39.

43. A host cell comprising the vector of claim 42.

44. A composition comprising the polynucleotide of claim 39 and a carrier.

* * * * *

SEQUENCE LISTING

```
<160> NUMBER OF SEQ ID NOS: 73

<210> SEQ ID NO 1
<211> LENGTH: 2898
<212> TYPE: DNA
<213> ORGANISM: Chlamydia sp.

<400> SEQUENCE: 1

atgaaaaaag cgtttttctt tttccttatt ggaaactccc tatcaggact agctagagag     60

gttccttcta gaatctttct tatgcccaac tcagttccag atcctacgaa agagtcgcta    120

tcaaataaaa ttagtttgac aggagacact cacaatctca ctaactgcta tctcgataac    180

ctacgctaca tactggctat tctacaaaaa actcccaatg aaggagctgc tgtcacaata    240

acagattacc taagcttttt tgatacacaa aaagaaggta tttattttgc aaaaaatctc    300
```

-continued

```
accccctgaaa gtggtggtgc gattggttat gcgagtccca attctcctac cgtggagatt    360
cgtgatacaa taggtcctgt aatctttgaa aataatactt gttgcagacc atttacatcg    420
agtaatccta atgcagctgt taataaaata agagaaggcg gagccattca tgctcaaaat    480
ctttacataa atcataatca tgatgtggtc ggatttatga agaacttttc ttatgtccga    540
ggaggagcca ttagtaccgc taatacccttt gttgtgagcg agaatcagtc ttgttttctc    600
tttatggaca acatctgtat tcaaactaat acagcaggaa aaggtggcgc tatctatgct    660
ggaacgagca attcttttga gagtaataac tgcgatctct tctttatcaa taacgcctgt    720
tgtgcaggag gagcgatctt ctcccctatc tgttctctaa caggaaatcg tggtaacatc    780
gttttctata acaatcgctg ctttaaaaat gtagaaacag cttcttcaga agcttctgat    840
ggaggagcaa ttaaagtaac tactcgccta gatgttacag gcaatcgtgg taggatcttt    900
tttagtgaca atatcacaaa aaattatggc ggagctattt acgctcctgt agttacccta    960
gtggataatg gccctaccta ctttataaac aatatcgcca ataataaggg gggcgctatc   1020
tatatagacg gaaccagcaa ctccaaaatt tctgccgacc gccatgctat tatttttaat   1080
gaaaatattg tgactaatgt aactaatgca aatggtacca gtacgtcagc taatcctcct   1140
agaagaaatg caataacagt agcaagctcc tctggtgaaa ttctattagg agcagggagt   1200
agccaaaatt taatttttta tgatcctatt gaagttagca atgcaggggt ctctgtgtcc   1260
ttcaataagg aagctgatca aacaggctct gtagtatttt caggagctac tgttaattct   1320
gcagattttc atcaacgcaa tttacaaaca aaaacacctg caccccttac tctcagtaat   1380
ggttttctat gtatcgaaga tcatgctcag cttacagtga atcgattcac acaaactggg   1440
ggtgttgttt ctcttgggaa tggagcagtt ctgagttgct ataaaaatgg tgcaggaaat   1500
tctgctagca atgcctctat aacactgaag catattggat tgaatctttc ttccattctg   1560
aaaagtggtg ctgagattcc tttattgtgg gtagagccta caaataacag caataactat   1620
acagcagata ctgcagctac cttttcatta agtgatgtaa aactctcact cattgatgac   1680
tatgggaatt ctccttatga atccacagat ctaacccatg ctctgtcatc acagcctatg   1740
ctatctattt ctgaggctag tgataaccag ctaagatctg atgatatgga tttttcggga   1800
ctaaatgtcc ctcattatgg atggcaagga ctttggactt ggggctgggc aaaaactcaa   1860
gatccagaac cagcatcttc agcaacaatc acagatccac aaaaagccaa tagattccat   1920
agaaccttat tactgacttg gcttcctgct gggtatgttc ctagcccgaa acacagaagt   1980
cccctcatag cgaatacctt atgggggaat atgctgcttg caacagaaag cttaaaaaat   2040
agtgcagaac tgacacctag tgatcatcct ttctggggaa ttacaggagg aggactaggc   2100
atgatggttt accaagatcc tcgagaaaat catcctggat tccatatgcg ctcttccgga   2160
tactctgcgg ggatgatagc agggcagaca cacaccttct cattgaaatt cagtcagacc   2220
tacaccaaac tcaatgagcg ttacgcaaaa aacaacgtat cttctaaaaa ttactcatgc   2280
caaggagaaa tgctcttctc attgcaagaa ggtttcttgc tgactaaatt agttgggctt   2340
tacagctatg gagaccataa ctgtcaccat ttctataccc aaggagaaaa tctaacatct   2400
caagggacgt tccgtagtca aacgatggga ggtgctgttt tttttgatct ccctatgaaa   2460
ccctttggat caacgcatat actgacagct ccctttttag gtgctcttgg tatttattct   2520
agcctgtctc actttactga ggtgggagcc tatccgcgaa gcttttctac aaagactcct   2580
ttgatcaatg tcctagtccc tattggagtt aaaggtagct ttatgaatgc tacccaaaga   2640
```

-continued

```
cctcaagcct ggactgtaga attggcatac caacccgttc tgtatagaca agaaccaggg   2700

atcgcgaccc agctcctagc cagtaagggt atttggtttg gtagtggaag cccctcatcg   2760

cgtcatgcca tgtcctataa aatctcacag caaacacaac ctttgagttg gttaactctc   2820

catttccagt atcatggatt ctactcctct tcaaccttct gtaattatct caatggggaa   2880

attgctctgc gattctag                                                 2898


<210> SEQ ID NO 2
<211> LENGTH: 965
<212> TYPE: PRT
<213> ORGANISM: Chlamydia sp.

<400> SEQUENCE: 2

Met Lys Lys Ala Phe Phe Phe Phe Leu Ile Gly Asn Ser Leu Ser Gly
1               5                   10                  15

Leu Ala Arg Glu Val Pro Ser Arg Ile Phe Leu Met Pro Asn Ser Val
            20                  25                  30

Pro Asp Pro Thr Lys Glu Ser Leu Ser Asn Lys Ile Ser Leu Thr Gly
        35                  40                  45

Asp Thr His Asn Leu Thr Asn Cys Tyr Leu Asp Asn Leu Arg Tyr Ile
    50                  55                  60

Leu Ala Ile Leu Gln Lys Thr Pro Asn Glu Gly Ala Ala Val Thr Ile
65                  70                  75                  80

Thr Asp Tyr Leu Ser Phe Phe Asp Thr Gln Lys Glu Gly Ile Tyr Phe
                85                  90                  95

Ala Lys Asn Leu Thr Pro Glu Ser Gly Gly Ala Ile Gly Tyr Ala Ser
            100                 105                 110

Pro Asn Ser Pro Thr Val Glu Ile Arg Asp Thr Ile Gly Pro Val Ile
        115                 120                 125

Phe Glu Asn Asn Thr Cys Cys Arg Pro Phe Thr Ser Ser Asn Pro Asn
    130                 135                 140

Ala Ala Val Asn Lys Ile Arg Glu Gly Gly Ala Ile His Ala Gln Asn
145                 150                 155                 160

Leu Tyr Ile Asn His Asn His Asp Val Val Gly Phe Met Lys Asn Phe
                165                 170                 175

Ser Tyr Val Arg Gly Gly Ala Ile Ser Thr Ala Asn Thr Phe Val Val
            180                 185                 190

Ser Glu Asn Gln Ser Cys Phe Leu Phe Met Asp Asn Ile Cys Ile Gln
        195                 200                 205

Thr Asn Thr Ala Gly Lys Gly Gly Ala Ile Tyr Ala Gly Thr Ser Asn
    210                 215                 220

Ser Phe Glu Ser Asn Asn Cys Asp Leu Phe Phe Ile Asn Asn Ala Cys
225                 230                 235                 240

Cys Ala Gly Gly Ala Ile Phe Ser Pro Ile Cys Ser Leu Thr Gly Asn
                245                 250                 255

Arg Gly Asn Ile Val Phe Tyr Asn Asn Arg Cys Phe Lys Asn Val Glu
            260                 265                 270

Thr Ala Ser Ser Glu Ala Ser Asp Gly Gly Ala Ile Lys Val Thr Thr
        275                 280                 285

Arg Leu Asp Val Thr Gly Asn Arg Gly Arg Ile Phe Phe Ser Asp Asn
    290                 295                 300

Ile Thr Lys Asn Tyr Gly Gly Ala Ile Tyr Ala Pro Val Val Thr Leu
305                 310                 315                 320

Val Asp Asn Gly Pro Thr Tyr Phe Ile Asn Asn Ile Ala Asn Asn Lys
```

-continued

```
                325                 330                 335

Gly Gly Ala Ile Tyr Ile Asp Gly Thr Ser Asn Ser Lys Ile Ser Ala
            340                 345                 350

Asp Arg His Ala Ile Ile Phe Asn Glu Asn Ile Val Thr Asn Val Thr
        355                 360                 365

Asn Ala Asn Gly Thr Ser Thr Ser Ala Asn Pro Pro Arg Arg Asn Ala
    370                 375                 380

Ile Thr Val Ala Ser Ser Ser Gly Glu Ile Leu Leu Gly Ala Gly Ser
385                 390                 395                 400

Ser Gln Asn Leu Ile Phe Tyr Asp Pro Ile Glu Val Ser Asn Ala Gly
                405                 410                 415

Val Ser Val Ser Phe Asn Lys Glu Ala Asp Gln Thr Gly Ser Val Val
            420                 425                 430

Phe Ser Gly Ala Thr Val Asn Ser Ala Asp Phe His Gln Arg Asn Leu
        435                 440                 445

Gln Thr Lys Thr Pro Ala Pro Leu Thr Leu Ser Asn Gly Phe Leu Cys
    450                 455                 460

Ile Glu Asp His Ala Gln Leu Thr Val Asn Arg Phe Thr Gln Thr Gly
465                 470                 475                 480

Gly Val Val Ser Leu Gly Asn Gly Ala Val Leu Ser Cys Tyr Lys Asn
                485                 490                 495

Gly Ala Gly Asn Ser Ala Ser Asn Ala Ser Ile Thr Leu Lys His Ile
            500                 505                 510

Gly Leu Asn Leu Ser Ser Ile Leu Lys Ser Gly Ala Glu Ile Pro Leu
        515                 520                 525

Leu Trp Val Glu Pro Thr Asn Asn Ser Asn Asn Tyr Thr Ala Asp Thr
    530                 535                 540

Ala Ala Thr Phe Ser Leu Ser Asp Val Lys Leu Ser Leu Ile Asp Asp
545                 550                 555                 560

Tyr Gly Asn Ser Pro Tyr Glu Ser Thr Asp Leu Thr His Ala Leu Ser
                565                 570                 575

Ser Gln Pro Met Leu Ser Ile Ser Glu Ala Ser Asp Asn Gln Leu Arg
            580                 585                 590

Ser Asp Asp Met Asp Phe Ser Gly Leu Asn Val Pro His Tyr Gly Trp
        595                 600                 605

Gln Gly Leu Trp Thr Trp Gly Trp Ala Lys Thr Gln Asp Pro Glu Pro
    610                 615                 620

Ala Ser Ser Ala Thr Ile Thr Asp Pro Gln Lys Ala Asn Arg Phe His
625                 630                 635                 640

Arg Thr Leu Leu Leu Thr Trp Leu Pro Ala Gly Tyr Val Pro Ser Pro
                645                 650                 655

Lys His Arg Ser Pro Leu Ile Ala Asn Thr Leu Trp Gly Asn Met Leu
            660                 665                 670

Leu Ala Thr Glu Ser Leu Lys Asn Ser Ala Glu Leu Thr Pro Ser Asp
        675                 680                 685

His Pro Phe Trp Gly Ile Thr Gly Gly Gly Leu Gly Met Met Val Tyr
    690                 695                 700

Gln Asp Pro Arg Glu Asn His Pro Gly Phe His Met Arg Ser Ser Gly
705                 710                 715                 720

Tyr Ser Ala Gly Met Ile Ala Gly Gln Thr His Thr Phe Ser Leu Lys
                725                 730                 735

Phe Ser Gln Thr Tyr Thr Lys Leu Asn Glu Arg Tyr Ala Lys Asn Asn
            740                 745                 750
```

-continued

```
Val Ser Ser Lys Asn Tyr Ser Cys Gln Gly Glu Met Leu Phe Ser Leu
        755                 760                 765

Gln Glu Gly Phe Leu Leu Thr Lys Leu Val Gly Leu Tyr Ser Tyr Gly
    770                 775                 780

Asp His Asn Cys His His Phe Tyr Thr Gln Gly Glu Asn Leu Thr Ser
785                 790                 795                 800

Gln Gly Thr Phe Arg Ser Gln Thr Met Gly Gly Ala Val Phe Phe Asp
                805                 810                 815

Leu Pro Met Lys Pro Phe Gly Ser Thr His Ile Leu Thr Ala Pro Phe
            820                 825                 830

Leu Gly Ala Leu Gly Ile Tyr Ser Ser Leu Ser His Phe Thr Glu Val
        835                 840                 845

Gly Ala Tyr Pro Arg Ser Phe Ser Thr Lys Thr Pro Leu Ile Asn Val
    850                 855                 860

Leu Val Pro Ile Gly Val Lys Gly Ser Phe Met Asn Ala Thr Gln Arg
865                 870                 875                 880

Pro Gln Ala Trp Thr Val Glu Leu Ala Tyr Gln Pro Val Leu Tyr Arg
                885                 890                 895

Gln Glu Pro Gly Ile Ala Thr Gln Leu Leu Ala Ser Lys Gly Ile Trp
            900                 905                 910

Phe Gly Ser Gly Ser Pro Ser Ser Arg His Ala Met Ser Tyr Lys Ile
        915                 920                 925

Ser Gln Gln Thr Gln Pro Leu Ser Trp Leu Thr Leu His Phe Gln Tyr
    930                 935                 940

His Gly Phe Tyr Ser Ser Ser Thr Phe Cys Asn Tyr Leu Asn Gly Glu
945                 950                 955                 960

Ile Ala Leu Arg Phe
                965


<210> SEQ ID NO 3
<211> LENGTH: 2637
<212> TYPE: DNA
<213> ORGANISM: Chlamydia sp.

<400> SEQUENCE: 3

atgcgacctg atcatatgaa cttctgttgt ctatgtgctg ctattttgtc atccacagcg      60

gtcctctttg gccaggatcc cttaggtgaa accgccctcc tcactaaaaa tcctaatcat     120

gtcgtctgta catttttga ggactgtacc atggagagcc tctttcctgc tctttgtgct     180

catgcatcac aagacgatcc tttgtatgta cttggaaatt cctactgttg gttcgtatct     240

aaactccata tcacggaccc caaagaggct ctttttaaag aaaaaggaga tctttccatt     300

caaaactttc gcttcctttc cttcacagat tgctcttcca aggaaagctc tccttctatt     360

attcatcaaa agaatggtca gttatccttg cgcaataatg gtagcatgag tttctgtcga     420

aatcatgctg aaggctctgg aggagccatc tctgcggatg ccttttctct acagcacaac     480

tatcttttca cagcttttga agagaattct tctaaaggaa atggcggagc cattcaggct     540

caaaccttct ctttatctag aaatgtgtcg cctatttctt tcgcccgtaa tcgtgcggat     600

ttaaatggcg gcgctatttg ctgtagtaat cttatttgtt cagggaatgt aaaccctctc     660

tttttcactg gaaactccgc cacgaatgga ggcgctattt gttgtatcag cgatctaaac     720

acctcagaaa aaggctctct ctctcttgct tgtaaccaag aaacgctatt tgcaagcaat     780

tctgctaaag aaaaaggcgg ggctatttat gccaagcaca tggtattgcg ttataacggt     840
```

-continued

```
cctgtttcct tcattaacaa cagcgctaaa ataggtggag ctatcgccat ccagtccgga    900

gggagtctct ctatccttgc aggtgaagga tctgttctgt tccagaataa ctcccaacgc    960

acctccgacc aaggtctagt aagaaacgcc atctacttag agaaagatgc gattctttct   1020

tccttagaag ctcgcaacgg agatattctt ttctttgatc ctattgtaca agaaagtagc   1080

agcaaagaat cgcctcttcc ctcctctttg caagccagcg tgacttctcc caccccagcc   1140

accgcatctc ctttagttat tcagacaagt gcaaaccgtt cagtgatttt ctcgagcgaa   1200

cgtctttctg aagaagaaaa aactcctgat aacctcactt cccaactaca gcagcctatc   1260

gaactgaaat ccggacgctt agttttaaaa gatcgcgctg tcctttccgc gccttctctc   1320

tctcaggatc ctcaagctct cctcattatg gaagcgggaa cttctttaaa aacttcctct   1380

gatttgaagt tagctacgct aagtattccc cttcattcct tagatactga aaaaagcgta   1440

actatccacg cccctaacct ttctatccaa aagatcttcc tctctaattc tggagatgag   1500

aatttttatg aaaatgtaga gcttctcagt aaagagcaaa acaatattcc tctccttact   1560

ctctctaaag agcaatctca tttacatctt cctgatggga acctctcttc tcactttgga   1620

tatcaaggag attggacttt ttcttggaaa gattctgatg aagggcattc tctgattgct   1680

aattggacgc ctaaaaacta tgtgcctcat ccagaacgtc aatctacact cgttgcgaac   1740

actctttgga acacctattc cgatatgcaa gctgtgcagt cgatgattaa tacaatagcg   1800

cacggaggag cctatctatt tggaacgtgg ggatctgctg tttctaattt attctatgct   1860

cacgacagct ctgggaaacc tatcgataat tggcatcata gaagccttgg ctacctattc   1920

ggtatcagta ctcacagttt agatgaccat tctttctgct tggctgcagg acaattactc   1980

gggaaatcgt ccgattcctt tattacgtct acagaaacga cctcctatat agctactgta   2040

caagcgcaac tcgctacctc tctaatgaaa atctctgcac aggcatgcta caatgaaagt   2100

atccatgagc taaaaacaaa atatcgctcc ttctctaaag aaggattcgg atcctggcat   2160

agcgttgcag tatccggaga agtgtgcgca tcgattccta ttgtatccaa tggttccgga   2220

ctgttcagct ccttctctat ttctctaaa ctgcaaggat tttcaggaac acaggacggt   2280

tttgaggaga gttcgggaga gattcggtcc ttttctgcca gctctttcag aaatatttca   2340

cttcctatag gaataacatt tgaaaaaaaa tcccaaaaaa cacgaaccta ctattacttt   2400

ctaggagcct acatccaaga cctgaaacgt gatgtggaat cgggacctgt agtgttactc   2460

aaaaatgccg tctcctggga tgctcctatg gcgaacttgg attcacgagc ctacatgttc   2520

aggcttacga atcaaagagc tctacacaga cttcagacgc tgttaaatgt gtcttgtgtg   2580

ctgcgtgggc aaagccatag ttactccctg gatctgggga ccacttacag gttctag      2637
```

<210> SEQ ID NO 4
<211> LENGTH: 878
<212> TYPE: PRT
<213> ORGANISM: Chlamydia sp.

<400> SEQUENCE: 4

```
Met Arg Pro Asp His Met Asn Phe Cys Cys Leu Cys Ala Ala Ile Leu
1               5                   10                  15

Ser Ser Thr Ala Val Leu Phe Gly Gln Asp Pro Leu Gly Glu Thr Ala
            20                  25                  30

Leu Leu Thr Lys Asn Pro Asn His Val Val Cys Thr Phe Phe Glu Asp
        35                  40                  45

Cys Thr Met Glu Ser Leu Phe Pro Ala Leu Cys Ala His Ala Ser Gln
    50                  55                  60
```

-continued

```
Asp Asp Pro Leu Tyr Val Leu Gly Asn Ser Tyr Cys Trp Phe Val Ser
65                  70                  75                  80

Lys Leu His Ile Thr Asp Pro Lys Glu Ala Leu Phe Lys Glu Lys Gly
                85                  90                  95

Asp Leu Ser Ile Gln Asn Phe Arg Phe Leu Ser Phe Thr Asp Cys Ser
            100                 105                 110

Ser Lys Glu Ser Ser Pro Ser Ile Ile His Gln Lys Asn Gly Gln Leu
        115                 120                 125

Ser Leu Arg Asn Asn Gly Ser Met Ser Phe Cys Arg Asn His Ala Glu
    130                 135                 140

Gly Ser Gly Gly Ala Ile Ser Ala Asp Ala Phe Ser Leu Gln His Asn
145                 150                 155                 160

Tyr Leu Phe Thr Ala Phe Glu Glu Asn Ser Ser Lys Gly Asn Gly Gly
                165                 170                 175

Ala Ile Gln Ala Gln Thr Phe Ser Leu Ser Arg Asn Val Ser Pro Ile
            180                 185                 190

Ser Phe Ala Arg Asn Arg Ala Asp Leu Asn Gly Gly Ala Ile Cys Cys
        195                 200                 205

Ser Asn Leu Ile Cys Ser Gly Asn Val Asn Pro Leu Phe Phe Thr Gly
    210                 215                 220

Asn Ser Ala Thr Asn Gly Gly Ala Ile Cys Cys Ile Ser Asp Leu Asn
225                 230                 235                 240

Thr Ser Glu Lys Gly Ser Leu Ser Leu Ala Cys Asn Gln Glu Thr Leu
                245                 250                 255

Phe Ala Ser Asn Ser Ala Lys Glu Lys Gly Gly Ala Ile Tyr Ala Lys
            260                 265                 270

His Met Val Leu Arg Tyr Asn Gly Pro Val Ser Phe Ile Asn Asn Ser
        275                 280                 285

Ala Lys Ile Gly Gly Ala Ile Ala Ile Gln Ser Gly Gly Ser Leu Ser
    290                 295                 300

Ile Leu Ala Gly Glu Gly Ser Val Leu Phe Gln Asn Asn Ser Gln Arg
305                 310                 315                 320

Thr Ser Asp Gln Gly Leu Val Arg Asn Ala Ile Tyr Leu Glu Lys Asp
                325                 330                 335

Ala Ile Leu Ser Ser Leu Glu Ala Arg Asn Gly Asp Ile Leu Phe Phe
            340                 345                 350

Asp Pro Ile Val Gln Glu Ser Ser Ser Lys Glu Ser Pro Leu Pro Ser
        355                 360                 365

Ser Leu Gln Ala Ser Val Thr Ser Pro Thr Pro Ala Thr Ala Ser Pro
    370                 375                 380

Leu Val Ile Gln Thr Ser Ala Asn Arg Ser Val Ile Phe Ser Ser Glu
385                 390                 395                 400

Arg Leu Ser Glu Glu Glu Lys Thr Pro Asp Asn Leu Thr Ser Gln Leu
                405                 410                 415

Gln Gln Pro Ile Glu Leu Lys Ser Gly Arg Leu Val Leu Lys Asp Arg
            420                 425                 430

Ala Val Leu Ser Ala Pro Ser Leu Ser Gln Asp Pro Gln Ala Leu Leu
        435                 440                 445

Ile Met Glu Ala Gly Thr Ser Leu Lys Thr Ser Ser Asp Leu Lys Leu
    450                 455                 460

Ala Thr Leu Ser Ile Pro Leu His Ser Leu Asp Thr Glu Lys Ser Val
465                 470                 475                 480
```

-continued

```
Thr Ile His Ala Pro Asn Leu Ser Ile Gln Lys Ile Phe Leu Ser Asn
                485                 490                 495

Ser Gly Asp Glu Asn Phe Tyr Glu Asn Val Glu Leu Leu Ser Lys Glu
            500                 505                 510

Gln Asn Asn Ile Pro Leu Leu Thr Leu Ser Lys Glu Gln Ser His Leu
        515                 520                 525

His Leu Pro Asp Gly Asn Leu Ser Ser His Phe Gly Tyr Gln Gly Asp
    530                 535                 540

Trp Thr Phe Ser Trp Lys Asp Ser Asp Glu Gly His Ser Leu Ile Ala
545                 550                 555                 560

Asn Trp Thr Pro Lys Asn Tyr Val Pro His Pro Glu Arg Gln Ser Thr
                565                 570                 575

Leu Val Ala Asn Thr Leu Trp Asn Thr Tyr Ser Asp Met Gln Ala Val
            580                 585                 590

Gln Ser Met Ile Asn Thr Ile Ala His Gly Gly Ala Tyr Leu Phe Gly
        595                 600                 605

Thr Trp Gly Ser Ala Val Ser Asn Leu Phe Tyr Ala His Asp Ser Ser
    610                 615                 620

Gly Lys Pro Ile Asp Asn Trp His His Arg Ser Leu Gly Tyr Leu Phe
625                 630                 635                 640

Gly Ile Ser Thr His Ser Leu Asp Asp His Ser Phe Cys Leu Ala Ala
                645                 650                 655

Gly Gln Leu Leu Gly Lys Ser Ser Asp Ser Phe Ile Thr Ser Thr Glu
            660                 665                 670

Thr Thr Ser Tyr Ile Ala Thr Val Gln Ala Gln Leu Ala Thr Ser Leu
        675                 680                 685

Met Lys Ile Ser Ala Gln Ala Cys Tyr Asn Glu Ser Ile His Glu Leu
    690                 695                 700

Lys Thr Lys Tyr Arg Ser Phe Ser Lys Glu Gly Phe Gly Ser Trp His
705                 710                 715                 720

Ser Val Ala Val Ser Gly Glu Val Cys Ala Ser Ile Pro Ile Val Ser
                725                 730                 735

Asn Gly Ser Gly Leu Phe Ser Ser Phe Ser Ile Phe Ser Lys Leu Gln
            740                 745                 750

Gly Phe Ser Gly Thr Gln Asp Gly Phe Glu Glu Ser Ser Gly Glu Ile
        755                 760                 765

Arg Ser Phe Ser Ala Ser Ser Phe Arg Asn Ile Ser Leu Pro Ile Gly
    770                 775                 780

Ile Thr Phe Glu Lys Lys Ser Gln Lys Thr Arg Thr Tyr Tyr Tyr Phe
785                 790                 795                 800

Leu Gly Ala Tyr Ile Gln Asp Leu Lys Arg Asp Val Glu Ser Gly Pro
                805                 810                 815

Val Val Leu Leu Lys Asn Ala Val Ser Trp Asp Ala Pro Met Ala Asn
            820                 825                 830

Leu Asp Ser Arg Ala Tyr Met Phe Arg Leu Thr Asn Gln Arg Ala Leu
        835                 840                 845

His Arg Leu Gln Thr Leu Leu Asn Val Ser Cys Val Leu Arg Gly Gln
    850                 855                 860

Ser His Ser Tyr Ser Leu Asp Leu Gly Thr Thr Tyr Arg Phe
865                 870                 875
```

<210> SEQ ID NO 5
<211> LENGTH: 42
<212> TYPE: PRT

<213> ORGANISM: Chlamydia sp.

<400> SEQUENCE: 5

```
Ser Gly Leu Ala Arg Glu Val Pro Ser Arg Ile Phe Leu Met Pro Asn
1               5                   10                  15

Ser Val Pro Asp Pro Thr Lys Glu Ser Leu Ser Asn Lys Ile Ser Leu
            20                  25                  30

Thr Gly Asp Thr His Asn Leu Thr Asn Cys
        35                  40
```

<210> SEQ ID NO 6
<211> LENGTH: 107
<212> TYPE: PRT
<213> ORGANISM: Chlamydia sp.

<400> SEQUENCE: 6

```
Ser Gly Leu Ala Arg Glu Val Pro Ser Arg Ile Phe Leu Met Pro Asn
1               5                   10                  15

Ser Val Pro Asp Pro Thr Lys Glu Ser Leu Ser Asn Lys Ile Ser Leu
            20                  25                  30

Thr Gly Asp Thr His Asn Leu Thr Asn Cys Tyr Leu Asp Asn Leu Arg
        35                  40                  45

Tyr Ile Leu Ala Ile Leu Gln Lys Thr Pro Asn Glu Gly Ala Ala Val
    50                  55                  60

Thr Ile Thr Asp Tyr Leu Ser Phe Phe Asp Thr Gln Lys Glu Gly Ile
65                  70                  75                  80

Tyr Phe Ala Lys Asn Leu Thr Pro Glu Ser Gly Gly Ala Ile Gly Tyr
                85                  90                  95

Ala Ser Pro Asn Ser Pro Thr Val Glu Ile Arg
            100                 105
```

<210> SEQ ID NO 7
<211> LENGTH: 81
<212> TYPE: PRT
<213> ORGANISM: Chlamydia sp.

<400> SEQUENCE: 7

```
Ser Leu Thr Gly Asp Thr His Asn Leu Thr Asn Cys Tyr Leu Asp Asn
1               5                   10                  15

Leu Arg Tyr Ile Leu Ala Ile Leu Gln Lys Thr Pro Asn Glu Gly Ala
            20                  25                  30

Ala Val Thr Ile Thr Asp Tyr Leu Ser Phe Phe Asp Thr Gln Lys Glu
        35                  40                  45

Gly Ile Tyr Phe Ala Lys Asn Leu Thr Pro Glu Ser Gly Gly Ala Ile
    50                  55                  60

Gly Tyr Ala Ser Pro Asn Ser Pro Thr Val Glu Ile Arg Asp Thr Ile
65                  70                  75                  80

Gly
```

<210> SEQ ID NO 8
<211> LENGTH: 66
<212> TYPE: PRT
<213> ORGANISM: Chlamydia sp.

<400> SEQUENCE: 8

```
Gly Pro Val Ile Phe Glu Asn Asn Thr Cys Cys Arg Pro Phe Thr Ser
1               5                   10                  15

Ser Asn Pro Asn Ala Ala Val Asn Lys Ile Arg Glu Gly Gly Ala Ile
```

-continued

```
            20                  25                  30

His Ala Gln Asn Leu Tyr Ile Asn His Asn His Asp Val Val Gly Phe
        35                  40                  45

Met Lys Asn Phe Ser Tyr Val Arg Gly Gly Ala Ile Ser Thr Ala Asn
    50                  55                  60

Thr Phe
65


<210> SEQ ID NO 9
<211> LENGTH: 67
<212> TYPE: PRT
<213> ORGANISM: Chlamydia sp.

<400> SEQUENCE: 9

Asn Gln Ser Cys Phe Leu Phe Met Asp Asn Ile Cys Ile Gln Thr Asn
1               5                   10                  15

Thr Ala Gly Lys Gly Gly Ala Ile Tyr Ala Gly Thr Ser Asn Ser Phe
            20                  25                  30

Glu Ser Asn Asn Cys Asp Leu Phe Phe Ile Asn Asn Ala Cys Cys Ala
        35                  40                  45

Gly Gly Ala Ile Phe Ser Pro Ile Cys Ser Leu Thr Gly Asn Arg Gly
    50                  55                  60

Asn Ile Val
65


<210> SEQ ID NO 10
<211> LENGTH: 92
<212> TYPE: PRT
<213> ORGANISM: Chlamydia sp.

<400> SEQUENCE: 10

Ser Ser Glu Ala Ser Asp Gly Gly Ala Ile Lys Val Thr Thr Arg Leu
1               5                   10                  15

Asp Val Thr Gly Asn Arg Gly Arg Ile Phe Phe Ser Asp Asn Ile Thr
            20                  25                  30

Lys Asn Tyr Gly Gly Ala Ile Tyr Ala Pro Val Val Thr Leu Val Asp
        35                  40                  45

Asn Gly Pro Thr Tyr Phe Ile Asn Asn Ile Ala Asn Asn Lys Gly Gly
    50                  55                  60

Ala Ile Tyr Ile Asp Gly Thr Ser Asn Ser Lys Ile Ser Ala Asp Arg
65                  70                  75                  80

His Ala Ile Ile Phe Asn Glu Asn Ile Val Thr Asn
                85                  90


<210> SEQ ID NO 11
<211> LENGTH: 66
<212> TYPE: PRT
<213> ORGANISM: Chlamydia sp.

<400> SEQUENCE: 11

Thr Ser Ala Asn Pro Pro Arg Arg Asn Ala Ile Thr Val Ala Ser Ser
1               5                   10                  15

Ser Gly Glu Ile Leu Leu Gly Ala Gly Ser Ser Gln Asn Leu Ile Phe
            20                  25                  30

Tyr Asp Pro Ile Glu Val Ser Asn Ala Gly Val Ser Val Ser Phe Asn
        35                  40                  45

Lys Glu Ala Asp Gln Thr Gly Ser Val Val Phe Ser Gly Ala Thr Val
    50                  55                  60
```

```
Asn Ser
65


<210> SEQ ID NO 12
<211> LENGTH: 51
<212> TYPE: PRT
<213> ORGANISM: Chlamydia sp.

<400> SEQUENCE: 12

Ser Ala Asp Phe His Gln Arg Asn Leu Gln Thr Lys Thr Pro Ala Pro
1               5                   10                  15

Leu Thr Leu Ser Asn Gly Phe Leu Cys Ile Glu Asp His Ala Gln Leu
            20                  25                  30

Thr Val Asn Arg Phe Thr Gln Thr Gly Gly Val Val Ser Leu Gly Asn
        35                  40                  45

Gly Ala Val
    50


<210> SEQ ID NO 13
<211> LENGTH: 66
<212> TYPE: PRT
<213> ORGANISM: Chlamydia sp.

<400> SEQUENCE: 13

Glu Ile Pro Leu Leu Trp Val Glu Pro Thr Asn Asn Ser Asn Asn Tyr
1               5                   10                  15

Thr Ala Asp Thr Ala Ala Thr Phe Ser Leu Ser Asp Val Lys Leu Ser
            20                  25                  30

Leu Ile Asp Asp Tyr Gly Asn Ser Pro Tyr Glu Ser Thr Asp Leu Thr
        35                  40                  45

His Ala Leu Ser Ser Gln Pro Met Leu Ser Ile Ser Glu Ala Ser Asp
    50                  55                  60

Asn Gln
65


<210> SEQ ID NO 14
<211> LENGTH: 36
<212> TYPE: PRT
<213> ORGANISM: Chlamydia sp.

<400> SEQUENCE: 14

Gln Leu Arg Ser Asp Asp Met Asp Phe Ser Gly Leu Asn Val Pro His
1               5                   10                  15

Tyr Gly Trp Gln Gly Leu Trp Thr Trp Gly Trp Ala Lys Thr Gln Asp
            20                  25                  30

Pro Glu Pro Ala
        35


<210> SEQ ID NO 15
<211> LENGTH: 36
<212> TYPE: PRT
<213> ORGANISM: Chlamydia sp.

<400> SEQUENCE: 15

Gly Trp Ala Lys Thr Gln Asp Pro Glu Pro Ala Ser Ser Ala Thr Ile
1               5                   10                  15

Thr Asp Pro Gln Lys Ala Asn Arg Phe His Arg Thr Leu Leu Leu Thr
            20                  25                  30

Trp Leu Pro Ala
```

```
        35


<210> SEQ ID NO 16
<211> LENGTH: 76
<212> TYPE: PRT
<213> ORGANISM: Chlamydia sp.

<400> SEQUENCE: 16

Ala Ser Ser Ala Thr Ile Thr Asp Pro Gln Lys Ala Asn Arg Phe His
1               5                   10                  15

Arg Thr Leu Leu Leu Thr Trp Leu Pro Ala Gly Tyr Val Pro Ser Pro
            20                  25                  30

Lys His Arg Ser Pro Leu Ile Ala Asn Thr Leu Trp Gly Asn Met Leu
        35                  40                  45

Leu Ala Thr Glu Ser Leu Lys Asn Ser Ala Glu Leu Thr Pro Ser Asp
    50                  55                  60

His Pro Phe Trp Gly Ile Thr Gly Gly Gly Leu Gly
65                  70                  75


<210> SEQ ID NO 17
<211> LENGTH: 76
<212> TYPE: PRT
<213> ORGANISM: Chlamydia sp.

<400> SEQUENCE: 17

Met Ile Ala Gly Gln Thr His Thr Phe Ser Leu Lys Phe Ser Gln Thr
1               5                   10                  15

Tyr Thr Lys Leu Asn Glu Arg Tyr Ala Lys Asn Asn Val Ser Ser Lys
            20                  25                  30

Asn Tyr Ser Cys Gln Gly Glu Met Leu Phe Ser Leu Gln Glu Gly Phe
        35                  40                  45

Leu Leu Thr Lys Leu Val Gly Leu Tyr Ser Tyr Gly Asp His Asn Cys
    50                  55                  60

His His Phe Tyr Thr Gln Gly Glu Asn Leu Thr Ser
65                  70                  75


<210> SEQ ID NO 18
<211> LENGTH: 21
<212> TYPE: PRT
<213> ORGANISM: Chlamydia sp.

<400> SEQUENCE: 18

Ser Lys Asn Tyr Ser Cys Gln Gly Glu Met Leu Phe Ser Leu Gln Glu
1               5                   10                  15

Gly Phe Leu Leu Thr
            20


<210> SEQ ID NO 19
<211> LENGTH: 61
<212> TYPE: PRT
<213> ORGANISM: Chlamydia sp.

<400> SEQUENCE: 19

Asp His Asn Cys His His Phe Tyr Thr Gln Gly Glu Asn Leu Thr Ser
1               5                   10                  15

Gln Gly Thr Phe Arg Ser Gln Thr Met Gly Gly Ala Val Phe Phe Asp
            20                  25                  30

Leu Pro Met Lys Pro Phe Gly Ser Thr His Ile Leu Thr Ala Pro Phe
        35                  40                  45
```

-continued

```
Leu Gly Ala Leu Gly Ile Tyr Ser Ser Leu Ser His Phe
    50                  55                  60


<210> SEQ ID NO 20
<211> LENGTH: 51
<212> TYPE: PRT
<213> ORGANISM: Chlamydia sp.

<400> SEQUENCE: 20

Phe Asp Leu Pro Met Lys Pro Phe Gly Ser Thr His Ile Leu Thr Ala
1               5                   10                  15

Pro Phe Leu Gly Ala Leu Gly Ile Tyr Ser Ser Leu Ser His Phe Thr
            20                  25                  30

Glu Val Gly Ala Tyr Pro Arg Ser Phe Ser Thr Lys Thr Pro Leu Ile
        35                  40                  45

Asn Val Leu
    50


<210> SEQ ID NO 21
<211> LENGTH: 31
<212> TYPE: PRT
<213> ORGANISM: Chlamydia sp.

<400> SEQUENCE: 21

Met Lys Lys Ala Phe Phe Phe Phe Leu Ile Gly Asn Ser Leu Ser Gly
1               5                   10                  15

Leu Ala Arg Glu Val Pro Ser Arg Ile Phe Leu Met Pro Asn Ser
            20                  25                  30


<210> SEQ ID NO 22
<211> LENGTH: 500
<212> TYPE: PRT
<213> ORGANISM: Chlamydia sp.

<400> SEQUENCE: 22

Met Lys Lys Ala Phe Phe Phe Phe Leu Ile Gly Asn Ser Leu Ser Gly
1               5                   10                  15

Leu Ala Arg Glu Val Pro Ser Arg Ile Phe Leu Met Pro Asn Ser Val
            20                  25                  30

Pro Asp Pro Thr Lys Glu Ser Leu Ser Asn Lys Ile Ser Leu Thr Gly
        35                  40                  45

Asp Thr His Asn Leu Thr Asn Cys Tyr Leu Asp Asn Leu Arg Tyr Ile
    50                  55                  60

Leu Ala Ile Leu Gln Lys Thr Pro Asn Glu Gly Ala Ala Val Thr Ile
65                  70                  75                  80

Thr Asp Tyr Leu Ser Phe Phe Asp Thr Gln Lys Glu Gly Ile Tyr Phe
                85                  90                  95

Ala Lys Asn Leu Thr Pro Glu Ser Gly Gly Ala Ile Gly Tyr Ala Ser
            100                 105                 110

Pro Asn Ser Pro Thr Val Glu Ile Arg Asp Thr Ile Gly Pro Val Ile
        115                 120                 125

Phe Glu Asn Asn Thr Cys Cys Arg Pro Phe Thr Ser Ser Asn Pro Asn
    130                 135                 140

Ala Ala Val Asn Lys Ile Arg Glu Gly Gly Ala Ile His Ala Gln Asn
145                 150                 155                 160

Leu Tyr Ile Asn His Asn His Asp Val Val Gly Phe Met Lys Asn Phe
                165                 170                 175

Ser Tyr Val Arg Gly Gly Ala Ile Ser Thr Ala Asn Thr Phe Val Val
```

-continued

```
            180                 185                 190

Ser Glu Asn Gln Ser Cys Phe Leu Phe Met Asp Asn Ile Cys Ile Gln
        195                 200                 205

Thr Asn Thr Ala Gly Lys Gly Gly Ala Ile Tyr Ala Gly Thr Ser Asn
    210                 215                 220

Ser Phe Glu Ser Asn Asn Cys Asp Leu Phe Phe Ile Asn Asn Ala Cys
225                 230                 235                 240

Cys Ala Gly Gly Ala Ile Phe Ser Pro Ile Cys Ser Leu Thr Gly Asn
                245                 250                 255

Arg Gly Asn Ile Val Phe Tyr Asn Asn Arg Cys Phe Lys Asn Val Glu
            260                 265                 270

Thr Ala Ser Ser Glu Ala Ser Asp Gly Gly Ala Ile Lys Val Thr Thr
        275                 280                 285

Arg Leu Asp Val Thr Gly Asn Arg Gly Arg Ile Phe Phe Ser Asp Asn
    290                 295                 300

Ile Thr Lys Asn Tyr Gly Gly Ala Ile Tyr Ala Pro Val Val Thr Leu
305                 310                 315                 320

Val Asp Asn Gly Pro Thr Tyr Phe Ile Asn Asn Ile Ala Asn Asn Lys
                325                 330                 335

Gly Gly Ala Ile Tyr Ile Asp Gly Thr Ser Asn Ser Lys Ile Ser Ala
            340                 345                 350

Asp Arg His Ala Ile Ile Phe Asn Glu Asn Ile Val Thr Asn Val Thr
        355                 360                 365

Asn Ala Asn Gly Thr Ser Thr Ser Ala Asn Pro Pro Arg Arg Asn Ala
    370                 375                 380

Ile Thr Val Ala Ser Ser Ser Gly Glu Ile Leu Leu Gly Ala Gly Ser
385                 390                 395                 400

Ser Gln Asn Leu Ile Phe Tyr Asp Pro Ile Glu Val Ser Asn Ala Gly
                405                 410                 415

Val Ser Val Ser Phe Asn Lys Glu Ala Asp Gln Thr Gly Ser Val Val
            420                 425                 430

Phe Ser Gly Ala Thr Val Asn Ser Ala Asp Phe His Gln Arg Asn Leu
        435                 440                 445

Gln Thr Lys Thr Pro Ala Pro Leu Thr Leu Ser Asn Gly Phe Leu Cys
    450                 455                 460

Ile Glu Asp His Ala Gln Leu Thr Val Asn Arg Phe Thr Gln Thr Gly
465                 470                 475                 480

Gly Val Val Ser Leu Gly Asn Gly Ala Val Leu Ser Cys Tyr Lys Asn
                485                 490                 495

Gly Ala Gly Asn
            500


<210> SEQ ID NO 23
<211> LENGTH: 28
<212> TYPE: PRT
<213> ORGANISM: Chlamydia sp.

<400> SEQUENCE: 23

Ala Ala Ile Leu Ser Ser Thr Ala Val Leu Phe Gly Gln Asp Pro Leu
1               5                   10                  15

Gly Glu Thr Ala Leu Leu Thr Lys Asn Pro Asn His
            20                  25


<210> SEQ ID NO 24
<211> LENGTH: 41
```

<212> TYPE: PRT
<213> ORGANISM: Chlamydia sp.

<400> SEQUENCE: 24

```
Val Leu Gly Asn Ser Tyr Cys Trp Phe Val Ser Lys Leu His Ile Thr
1               5                   10                  15

Asp Pro Lys Glu Ala Leu Phe Lys Glu Lys Gly Asp Leu Ser Ile Gln
            20                  25                  30

Asn Phe Arg Phe Leu Ser Phe Thr Asp
        35                  40
```

<210> SEQ ID NO 25
<211> LENGTH: 76
<212> TYPE: PRT
<213> ORGANISM: Chlamydia sp.

<400> SEQUENCE: 25

```
Ile Ser Ala Asp Ala Phe Ser Leu Gln His Asn Tyr Leu Phe Thr Ala
1               5                   10                  15

Phe Glu Glu Asn Ser Ser Lys Gly Asn Gly Gly Ala Ile Gln Ala Gln
            20                  25                  30

Thr Phe Ser Leu Ser Arg Asn Val Ser Pro Ile Ser Phe Ala Arg Asn
        35                  40                  45

Arg Ala Asp Leu Asn Gly Gly Ala Ile Cys Cys Ser Asn Leu Ile Cys
    50                  55                  60

Ser Gly Asn Val Asn Pro Leu Phe Phe Thr Gly Asn
65                  70                  75
```

<210> SEQ ID NO 26
<211> LENGTH: 41
<212> TYPE: PRT
<213> ORGANISM: Chlamydia sp.

<400> SEQUENCE: 26

```
Ala Cys Asn Gln Glu Thr Leu Phe Ala Ser Asn Ser Ala Lys Glu Lys
1               5                   10                  15

Gly Gly Ala Ile Tyr Ala Lys His Met Val Leu Arg Tyr Asn Gly Pro
            20                  25                  30

Val Ser Phe Ile Asn Asn Ser Ala Lys
        35                  40
```

<210> SEQ ID NO 27
<211> LENGTH: 86
<212> TYPE: PRT
<213> ORGANISM: Chlamydia sp.

<400> SEQUENCE: 27

```
Leu Gln Ala Ser Val Thr Ser Pro Thr Pro Ala Thr Ala Ser Pro Leu
1               5                   10                  15

Val Ile Gln Thr Ser Ala Asn Arg Ser Val Ile Phe Ser Ser Glu Arg
            20                  25                  30

Leu Ser Glu Glu Glu Lys Thr Pro Asp Asn Leu Thr Ser Gln Leu Gln
        35                  40                  45

Gln Pro Ile Glu Leu Lys Ser Gly Arg Leu Val Leu Lys Asp Arg Ala
    50                  55                  60

Val Leu Ser Ala Pro Ser Leu Ser Gln Asp Pro Gln Ala Leu Leu Ile
65                  70                  75                  80

Met Glu Ala Gly Thr Ser
                85
```

```
<210> SEQ ID NO 28
<211> LENGTH: 56
<212> TYPE: PRT
<213> ORGANISM: Chlamydia sp.

<400> SEQUENCE: 28

Glu Arg Leu Ser Glu Glu Glu Lys Thr Pro Asp Asn Leu Thr Ser Gln
1               5                   10                  15

Leu Gln Gln Pro Ile Glu Leu Lys Ser Gly Arg Leu Val Leu Lys Asp
            20                  25                  30

Arg Ala Val Leu Ser Ala Pro Ser Leu Ser Gln Asp Pro Gln Ala Leu
        35                  40                  45

Leu Ile Met Glu Ala Gly Thr Ser
    50                  55


<210> SEQ ID NO 29
<211> LENGTH: 51
<212> TYPE: PRT
<213> ORGANISM: Chlamydia sp.

<400> SEQUENCE: 29

Pro Leu His Ser Leu Asp Thr Glu Lys Ser Val Thr Ile His Ala Pro
1               5                   10                  15

Asn Leu Ser Ile Gln Lys Ile Phe Leu Ser Asn Ser Gly Asp Glu Asn
            20                  25                  30

Phe Tyr Glu Asn Val Glu Leu Leu Ser Lys Glu Gln Asn Asn Ile Pro
        35                  40                  45

Leu Leu Thr
    50


<210> SEQ ID NO 30
<211> LENGTH: 56
<212> TYPE: PRT
<213> ORGANISM: Chlamydia sp.

<400> SEQUENCE: 30

Ser Asn Leu Phe Tyr Ala His Asp Ser Ser Gly Lys Pro Ile Asp Asn
1               5                   10                  15

Trp His His Arg Ser Leu Gly Tyr Leu Phe Gly Ile Ser Thr His Ser
            20                  25                  30

Leu Asp Asp His Ser Phe Cys Leu Ala Ala Gly Gln Leu Leu Gly Lys
        35                  40                  45

Ser Ser Asp Ser Phe Ile Thr Ser
    50                  55


<210> SEQ ID NO 31
<211> LENGTH: 66
<212> TYPE: PRT
<213> ORGANISM: Chlamydia sp.

<400> SEQUENCE: 31

Ser Phe Ser Lys Glu Gly Phe Gly Ser Trp His Ser Val Ala Val Ser
1               5                   10                  15

Gly Glu Val Cys Ala Ser Ile Pro Ile Val Ser Asn Gly Ser Gly Leu
            20                  25                  30

Phe Ser Ser Phe Ser Ile Phe Ser Lys Leu Gln Gly Phe Ser Gly Thr
        35                  40                  45

Gln Asp Gly Phe Glu Glu Ser Ser Gly Glu Ile Arg Ser Phe Ser Ala
```

```
    50                  55                  60

Ser Ser
65


<210> SEQ ID NO 32
<211> LENGTH: 61
<212> TYPE: PRT
<213> ORGANISM: Chlamydia sp.

<400> SEQUENCE: 32

Ser Gly Glu Ile Arg Ser Phe Ser Ala Ser Ser Phe Arg Asn Ile Ser
1               5                   10                  15

Leu Pro Ile Gly Ile Thr Phe Glu Lys Lys Ser Gln Lys Thr Arg Thr
            20                  25                  30

Tyr Tyr Tyr Phe Leu Gly Ala Tyr Ile Gln Asp Leu Lys Arg Asp Val
        35                  40                  45

Glu Ser Gly Pro Val Val Leu Leu Lys Asn Ala Val Ser
    50                  55                  60


<210> SEQ ID NO 33
<211> LENGTH: 31
<212> TYPE: PRT
<213> ORGANISM: Chlamydia sp.

<400> SEQUENCE: 33

Met Ala Asn Leu Asp Ser Arg Ala Tyr Met Phe Arg Leu Thr Asn Gln
1               5                   10                  15

Arg Ala Leu His Arg Leu Gln Thr Leu Leu Asn Val Ser Cys Val
            20                  25                  30


<210> SEQ ID NO 34
<211> LENGTH: 500
<212> TYPE: PRT
<213> ORGANISM: Chlamydia sp.

<400> SEQUENCE: 34

Met Arg Pro Asp His Met Asn Phe Cys Cys Leu Cys Ala Ala Ile Leu
1               5                   10                  15

Ser Ser Thr Ala Val Leu Phe Gly Gln Asp Pro Leu Gly Glu Thr Ala
            20                  25                  30

Leu Leu Thr Lys Asn Pro Asn His Val Val Cys Thr Phe Phe Glu Asp
        35                  40                  45

Cys Thr Met Glu Ser Leu Phe Pro Ala Leu Cys Ala His Ala Ser Gln
    50                  55                  60

Asp Asp Pro Leu Tyr Val Leu Gly Asn Ser Tyr Cys Trp Phe Val Ser
65                  70                  75                  80

Lys Leu His Ile Thr Asp Pro Lys Glu Ala Leu Phe Lys Glu Lys Gly
                85                  90                  95

Asp Leu Ser Ile Gln Asn Phe Arg Phe Leu Ser Phe Thr Asp Cys Ser
            100                 105                 110

Ser Lys Glu Ser Ser Pro Ser Ile Ile His Gln Lys Asn Gly Gln Leu
        115                 120                 125

Ser Leu Arg Asn Asn Gly Ser Met Ser Phe Cys Arg Asn His Ala Glu
    130                 135                 140

Gly Ser Gly Gly Ala Ile Ser Ala Asp Ala Phe Ser Leu Gln His Asn
145                 150                 155                 160

Tyr Leu Phe Thr Ala Phe Glu Glu Asn Ser Ser Lys Gly Asn Gly Gly
                165                 170                 175
```

```
Ala Ile Gln Ala Gln Thr Phe Ser Leu Ser Arg Asn Val Ser Pro Ile
            180                 185                 190

Ser Phe Ala Arg Asn Arg Ala Asp Leu Asn Gly Gly Ala Ile Cys Cys
        195                 200                 205

Ser Asn Leu Ile Cys Ser Gly Asn Val Asn Pro Leu Phe Phe Thr Gly
    210                 215                 220

Asn Ser Ala Thr Asn Gly Gly Ala Ile Cys Cys Ile Ser Asp Leu Asn
225                 230                 235                 240

Thr Ser Glu Lys Gly Ser Leu Ser Leu Ala Cys Asn Gln Glu Thr Leu
                245                 250                 255

Phe Ala Ser Asn Ser Ala Lys Glu Lys Gly Gly Ala Ile Tyr Ala Lys
            260                 265                 270

His Met Val Leu Arg Tyr Asn Gly Pro Val Ser Phe Ile Asn Asn Ser
        275                 280                 285

Ala Lys Ile Gly Gly Ala Ile Ala Ile Gln Ser Gly Gly Ser Leu Ser
    290                 295                 300

Ile Leu Ala Gly Glu Gly Ser Val Leu Phe Gln Asn Asn Ser Gln Arg
305                 310                 315                 320

Thr Ser Asp Gln Gly Leu Val Arg Asn Ala Ile Tyr Leu Glu Lys Asp
                325                 330                 335

Ala Ile Leu Ser Ser Leu Glu Ala Arg Asn Gly Asp Ile Leu Phe Phe
            340                 345                 350

Asp Pro Ile Val Gln Glu Ser Ser Ser Lys Glu Ser Pro Leu Pro Ser
        355                 360                 365

Ser Leu Gln Ala Ser Val Thr Ser Pro Thr Pro Ala Thr Ala Ser Pro
    370                 375                 380

Leu Val Ile Gln Thr Ser Ala Asn Arg Ser Val Ile Phe Ser Ser Glu
385                 390                 395                 400

Arg Leu Ser Glu Glu Glu Lys Thr Pro Asp Asn Leu Thr Ser Gln Leu
                405                 410                 415

Gln Gln Pro Ile Glu Leu Lys Ser Gly Arg Leu Val Leu Lys Asp Arg
            420                 425                 430

Ala Val Leu Ser Ala Pro Ser Leu Ser Gln Asp Pro Gln Ala Leu Leu
        435                 440                 445

Ile Met Glu Ala Gly Thr Ser Leu Lys Thr Ser Ser Asp Leu Lys Leu
    450                 455                 460

Ala Thr Leu Ser Ile Pro Leu His Ser Leu Asp Thr Glu Lys Ser Val
465                 470                 475                 480

Thr Ile His Ala Pro Asn Leu Ser Ile Gln Lys Ile Phe Leu Ser Asn
                485                 490                 495

Ser Gly Asp Glu
            500


<210> SEQ ID NO 35
<211> LENGTH: 10
<212> TYPE: PRT
<213> ORGANISM: Chlamydia sp.

<400> SEQUENCE: 35

Val Pro Asp Pro Thr Lys Glu Ser Leu Ser
1               5                   10


<210> SEQ ID NO 36
<211> LENGTH: 126
<212> TYPE: PRT
```

<213> ORGANISM: Chlamydia sp.

<400> SEQUENCE: 36

```
Thr Cys Ala Gly Gly Ala Cys Thr Ala Gly Cys Thr Ala Gly Ala Gly
1               5                   10                  15

Ala Gly Gly Thr Thr Cys Cys Thr Thr Cys Thr Ala Gly Ala Ala Thr
            20                  25                  30

Cys Thr Thr Thr Cys Thr Thr Ala Thr Gly Cys Cys Cys Ala Ala Cys
        35                  40                  45

Thr Cys Ala Gly Thr Thr Cys Cys Ala Gly Ala Thr Cys Cys Thr Ala
    50                  55                  60

Cys Gly Ala Ala Ala Gly Ala Gly Thr Cys Gly Cys Thr Ala Thr Cys
65                  70                  75                  80

Ala Ala Ala Thr Ala Ala Ala Ala Thr Thr Ala Gly Thr Thr Thr Gly
                85                  90                  95

Ala Cys Ala Gly Gly Ala Gly Ala Cys Ala Cys Thr Cys Ala Cys Ala
            100                 105                 110

Ala Thr Cys Thr Cys Ala Cys Thr Ala Ala Cys Thr Gly Cys
        115                 120                 125
```

<210> SEQ ID NO 37
<211> LENGTH: 321
<212> TYPE: PRT
<213> ORGANISM: Chlamydia sp.

<400> SEQUENCE: 37

```
Thr Cys Ala Gly Gly Ala Cys Thr Ala Gly Cys Thr Ala Gly Ala Gly
1               5                   10                  15

Ala Gly Gly Thr Thr Cys Cys Thr Thr Cys Thr Ala Gly Ala Ala Thr
            20                  25                  30

Cys Thr Thr Thr Cys Thr Thr Ala Thr Gly Cys Cys Cys Ala Ala Cys
        35                  40                  45

Thr Cys Ala Gly Thr Thr Cys Cys Ala Gly Ala Thr Cys Cys Thr Ala
    50                  55                  60

Cys Gly Ala Ala Ala Gly Ala Gly Thr Cys Gly Cys Thr Ala Thr Cys
65                  70                  75                  80

Ala Ala Ala Thr Ala Ala Ala Ala Thr Thr Ala Gly Thr Thr Thr Gly
                85                  90                  95

Ala Cys Ala Gly Gly Ala Gly Ala Cys Ala Cys Thr Cys Ala Cys Ala
            100                 105                 110

Ala Thr Cys Thr Cys Ala Cys Thr Ala Ala Cys Thr Gly Cys Thr Ala
        115                 120                 125

Thr Cys Thr Cys Gly Ala Thr Ala Ala Cys Cys Thr Ala Cys Gly Cys
    130                 135                 140

Thr Ala Cys Ala Thr Ala Cys Thr Gly Gly Cys Thr Ala Thr Thr Cys
145                 150                 155                 160

Thr Ala Cys Ala Ala Ala Ala Ala Ala Ala Cys Thr Cys Cys Cys Ala Ala
                165                 170                 175

Thr Gly Ala Ala Gly Gly Ala Gly Cys Thr Gly Cys Thr Gly Thr Cys
            180                 185                 190

Ala Cys Ala Ala Thr Ala Ala Cys Ala Gly Ala Thr Thr Ala Cys Cys
        195                 200                 205

Thr Ala Ala Gly Cys Thr Thr Thr Thr Thr Thr Gly Ala Thr Ala Cys
    210                 215                 220

Ala Cys Ala Ala Ala Ala Ala Gly Ala Ala Gly Gly Thr Ala Thr Thr
```

```
225                 230                 235                 240

Thr Ala Thr Thr Thr Thr Gly Cys Ala Ala Ala Ala Ala Ala Thr Cys
                245                 250                 255

Thr Cys Ala Cys Cys Cys Cys Thr Gly Ala Ala Ala Gly Thr Gly Gly
            260                 265                 270

Thr Gly Gly Thr Gly Cys Gly Ala Thr Thr Gly Gly Thr Thr Ala Thr
        275                 280                 285

Gly Cys Gly Ala Gly Thr Cys Cys Cys Ala Ala Thr Thr Cys Thr Cys
    290                 295                 300

Cys Thr Ala Cys Cys Gly Thr Gly Gly Ala Gly Ala Thr Thr Cys Gly
305                 310                 315                 320

Thr
```

<210> SEQ ID NO 38
<211> LENGTH: 243
<212> TYPE: PRT
<213> ORGANISM: Chlamydia sp.

<400> SEQUENCE: 38

```
Ala Gly Thr Thr Thr Gly Ala Cys Ala Gly Gly Ala Gly Ala Cys Ala
1               5                   10                  15

Cys Thr Cys Ala Cys Ala Ala Thr Cys Thr Cys Ala Cys Thr Ala Ala
            20                  25                  30

Cys Thr Gly Cys Thr Ala Thr Cys Thr Cys Gly Ala Thr Ala Ala Cys
        35                  40                  45

Cys Thr Ala Cys Gly Cys Thr Ala Cys Ala Thr Ala Cys Thr Gly Gly
    50                  55                  60

Cys Thr Ala Thr Thr Cys Thr Ala Cys Ala Ala Ala Ala Ala Ala Cys
65                  70                  75                  80

Thr Cys Cys Cys Ala Ala Thr Gly Ala Ala Gly Gly Ala Gly Cys Thr
                85                  90                  95

Gly Cys Thr Gly Thr Cys Ala Cys Ala Ala Thr Ala Ala Cys Ala Gly
            100                 105                 110

Ala Thr Thr Ala Cys Cys Thr Ala Ala Gly Cys Thr Thr Thr Thr Thr
        115                 120                 125

Thr Gly Ala Thr Ala Cys Ala Cys Ala Ala Ala Ala Ala Gly Ala Ala
    130                 135                 140

Gly Gly Thr Ala Thr Thr Thr Ala Thr Thr Thr Thr Gly Cys Ala Ala
145                 150                 155                 160

Ala Ala Ala Ala Thr Cys Thr Cys Ala Cys Cys Cys Cys Thr Gly Ala
                165                 170                 175

Ala Ala Gly Thr Gly Gly Thr Gly Gly Thr Gly Cys Gly Ala Thr Thr
            180                 185                 190

Gly Gly Thr Thr Ala Thr Gly Cys Gly Ala Gly Thr Cys Cys Cys Ala
        195                 200                 205

Ala Thr Thr Cys Thr Cys Cys Thr Ala Cys Cys Gly Thr Gly Gly Ala
    210                 215                 220

Gly Ala Thr Thr Cys Gly Thr Gly Ala Thr Ala Cys Ala Ala Thr Ala
225                 230                 235                 240

Gly Gly Thr
```

<210> SEQ ID NO 39
<211> LENGTH: 198
<212> TYPE: DNA
<213> ORGANISM: Chlamydia sp.

<400> SEQUENCE: 39
ggtcctgtaa tctttgaaaa taatacttgt tgcagaccat ttacatcgag taatcctaat 60
gcagctgtta ataaaataag agaaggcgga gccattcatg ctcaaaatct ttacataaat 120
cataatcatg atgtggtcgg atttatgaag aacttttctt atgtccgagg aggagccatt 180
agtaccgcta ataccttt 198

<210> SEQ ID NO 40
<211> LENGTH: 201
<212> TYPE: DNA
<213> ORGANISM: Chlamydia sp.

<400> SEQUENCE: 40
aatcagtctt gttttctctt tatggacaac atctgtattc aaactaatac agcaggaaaa 60
ggtggcgcta tctatgctgg aacgagcaat tcttttgaga gtaataactg cgatctcttc 120
tttatcaata acgcctgttg tgcaggagga gcgatcttct cccctatctg ttctctaaca 180
ggaaatcgtg gtaacatcgt t 201

<210> SEQ ID NO 41
<211> LENGTH: 276
<212> TYPE: DNA
<213> ORGANISM: Chlamydia sp.

<400> SEQUENCE: 41
tcttcagaag cttctgatgg aggagcaatt aaagtaacta ctcgcctaga tgttacaggc 60
aatcgtggta ggatcttttt tagtgacaat atcacaaaaa attatggcgg agctatttac 120
gctcctgtag ttaccctagt ggataatggc cctacctact ttataaacaa tatcgccaat 180
aataaggggg gcgctatcta tatagacgga accagcaact ccaaaatttc tgccgaccgc 240
catgctatta tttttaatga aaatattgtg actaat 276

<210> SEQ ID NO 42
<211> LENGTH: 198
<212> TYPE: DNA
<213> ORGANISM: Chlamydia sp.

<400> SEQUENCE: 42
acgtcagcta atcctcctag aagaaatgca ataacagtag caagctcctc tggtgaaatt 60
ctattaggag cagggagtag ccaaaattta atttttttatg atcctattga agttagcaat 120
gcaggggtct ctgtgtcctt caataaggaa gctgatcaaa caggctctgt agtattttca 180
ggagctactg ttaattct 198

<210> SEQ ID NO 43
<211> LENGTH: 153
<212> TYPE: DNA
<213> ORGANISM: Chlamydia sp.

<400> SEQUENCE: 43
tctgcagatt ttcatcaacg caatttacaa acaaaaacac ctgcacccct tactctcagt 60
aatggttttc tatgtatcga agatcatgct cagcttacag tgaatcgatt cacacaaact 120
gggggtgttg tttctcttgg gaatggagca gtt 153

<210> SEQ ID NO 44
<211> LENGTH: 198
<212> TYPE: DNA

<213> ORGANISM: Chlamydia sp.

<400> SEQUENCE: 44

```
gagattcctt tattgtgggt agagcctaca aataacagca ataactatac agcagatact      60

gcagctacct tttcattaag tgatgtaaaa ctctcactca ttgatgacta tgggaattct     120

ccttatgaat ccacagatct aacccatgct ctgtcatcac agcctatgct atctatttct     180

gaggctagtg ataaccag                                                   198
```

<210> SEQ ID NO 45
<211> LENGTH: 108
<212> TYPE: DNA
<213> ORGANISM: Chlamydia sp.

<400> SEQUENCE: 45

```
cagctaagat ctgatgatat ggatttttcg ggactaaatg tccctcatta tggatggcaa      60

ggactttgga cttggggctg ggcaaaaact caagatccag aaccagca                  108
```

<210> SEQ ID NO 46
<211> LENGTH: 108
<212> TYPE: DNA
<213> ORGANISM: Chlamydia sp.

<400> SEQUENCE: 46

```
ggctgggcaa aaactcaaga tccagaacca gcatcttcag caacaatcac agatccacaa      60

aaagccaata gattccatag aaccttatta ctgacttggc ttcctgct                  108
```

<210> SEQ ID NO 47
<211> LENGTH: 228
<212> TYPE: DNA
<213> ORGANISM: Chlamydia sp.

<400> SEQUENCE: 47

```
gcatcttcag caacaatcac agatccacaa aaagccaata gattccatag aaccttatta      60

ctgacttggc ttcctgctgg gtatgttcct agcccgaaac acagaagtcc cctcatagcg     120

aataccttat gggggaatat gctgcttgca acagaaagct taaaaaatag tgcagaactg     180

acacctagtg atcatccttt ctggggaatt acaggaggag gactaggc                  228
```

<210> SEQ ID NO 48
<211> LENGTH: 228
<212> TYPE: DNA
<213> ORGANISM: Chlamydia sp.

<400> SEQUENCE: 48

```
atgatagcag ggcagacaca caccttctca ttgaaattca gtcagaccta caccaaactc      60

aatgagcgtt acgcaaaaaa caacgtatct tctaaaaatt actcatgcca aggagaaatg     120

ctcttctcat tgcaagaagg tttcttgctg actaaattag ttgggcttta cagctatgga     180

gaccataact gtcaccattt ctatacccaa ggagaaaatc taacatct                  228
```

<210> SEQ ID NO 49
<211> LENGTH: 63
<212> TYPE: DNA
<213> ORGANISM: Chlamydia sp.

<400> SEQUENCE: 49

```
tctaaaaatt actcatgcca aggagaaatg ctcttctcat tgcaagaagg tttcttgctg      60

act                                                                    63
```

<210> SEQ ID NO 50
<211> LENGTH: 183
<212> TYPE: DNA
<213> ORGANISM: Chlamydia sp.

<400> SEQUENCE: 50
gaccataact gtcaccattt ctatacccaa ggagaaaatc taacatctca agggacgttc 60
cgtagtcaaa cgatgggagg tgctgttttt tttgatctcc ctatgaaacc ctttggatca 120
acgcatatac tgacagctcc ctttttaggt gctcttggta tttattctag cctgtctcac 180
ttt 183

<210> SEQ ID NO 51
<211> LENGTH: 153
<212> TYPE: DNA
<213> ORGANISM: Chlamydia sp.

<400> SEQUENCE: 51
tttgatctcc ctatgaaacc ctttggatca acgcatatac tgacagctcc ctttttaggt 60
gctcttggta tttattctag cctgtctcac tttactgagg tgggagccta tccgcgaagc 120
ttttctacaa agactccttt gatcaatgtc cta 153

<210> SEQ ID NO 52
<211> LENGTH: 93
<212> TYPE: DNA
<213> ORGANISM: Chlamydia sp.

<400> SEQUENCE: 52
atgaaaaaag cgtttttctt tttccttatt ggaaactccc tatcaggact agctagagag 60
gttccttcta gaatctttct tatgcccaac tca 93

<210> SEQ ID NO 53
<211> LENGTH: 1500
<212> TYPE: DNA
<213> ORGANISM: Chlamydia sp.

<400> SEQUENCE: 53
atgaaaaaag cgtttttctt tttccttatt ggaaactccc tatcaggact agctagagag 60
gttccttcta gaatctttct tatgcccaac tcagttccag atcctacgaa agagtcgcta 120
tcaaataaaa ttagtttgac aggagacact cacaatctca ctaactgcta tctcgataac 180
ctacgctaca tactggctat tctacaaaaa actcccaatg aaggagctgc tgtcacaata 240
acagattacc taagcttttt tgatacacaa aaagaaggta tttattttgc aaaaaatctc 300
acccctgaaa gtggtggtgc gattggttat gcgagtccca attctcctac cgtggagatt 360
cgtgatacaa taggtcctgt aatctttgaa aataatactt gttgcagacc atttacatcg 420
agtaatccta atgcagctgt taataaaata agagaaggcg gagccattca tgctcaaaat 480
ctttacataa atcataatca tgatgtggtc ggatttatga agaacttttc ttatgtccga 540
ggaggagcca ttagtaccgc taataccttt gttgtgagcg agaatcagtc ttgttttctc 600
tttatggaca acatctgtat tcaaactaat acagcaggaa aaggtggcgc tatctatgct 660
ggaacgagca attcttttga gagtaataac tgcgatctct tctttatcaa taacgcctgt 720
tgtgcaggag gagcgatctt ctcccctatc tgttctctaa caggaaatcg tggtaacatc 780
gttttctata acaatcgctg ctttaaaaat gtagaaacag cttcttcaga agcttctgat 840

-continued

```
ggaggagcaa ttaaagtaac tactcgccta gatgttacag gcaatcgtgg taggatcttt    900

tttagtgaca atatcacaaa aaattatggc ggagctattt acgctcctgt agttacccta    960

gtggataatg gccctaccta ctttataaac aatatcgcca ataataaggg gggcgctatc   1020

tatatagacg gaaccagcaa ctccaaaatt tctgccgacc gccatgctat tatttttaat   1080

gaaaatattg tgactaatgt aactaatgca aatggtacca gtacgtcagc taatcctcct   1140

agaagaaatg caataacagt agcaagctcc tctggtgaaa ttctattagg agcagggagt   1200

agccaaaatt taattttta tgatcctatt gaagttagca atgcaggggt ctctgtgtcc   1260

ttcaataagg aagctgatca aacaggctct gtagtatttt caggagctac tgttaattct   1320

gcagattttc atcaacgcaa tttacaaaca aaaacacctg caccccttac tctcagtaat   1380

ggttttctat gtatcgaaga tcatgctcag cttacagtga atcgattcac acaaactggg   1440

ggtgttgttt ctcttgggaa tggagcagtt ctgagttgct ataaaaatgg tgcaggaaat   1500
```

<210> SEQ ID NO 54
<211> LENGTH: 84
<212> TYPE: DNA
<213> ORGANISM: Chlamydia sp.

<400> SEQUENCE: 54

```
gctgctattt tgtcatccac agcggtcctc tttggccagg atcccttagg tgaaaccgcc     60

ctcctcacta aaaatcctaa tcat                                            84
```

<210> SEQ ID NO 55
<211> LENGTH: 123
<212> TYPE: DNA
<213> ORGANISM: Chlamydia sp.

<400> SEQUENCE: 55

```
gtacttggaa attcctactg ttggttcgta tctaaactcc atatcacgga ccccaaagag     60

gctcttttta aagaaaaagg agatctttcc attcaaaact ttcgcttcct ttccttcaca    120

gat                                                                  123
```

<210> SEQ ID NO 56
<211> LENGTH: 228
<212> TYPE: DNA
<213> ORGANISM: Chlamydia sp.

<400> SEQUENCE: 56

```
atctctgcgg atgccttttc tctacagcac aactatcttt tcacagcttt tgaagagaat     60

tcttctaaag gaaatggcgg agccattcag gctcaaacct tctctttatc tagaaatgtg    120

tcgcctattt ctttcgcccg taatcgtgcg gatttaaatg gcggcgctat ttgctgtagt    180

aatcttattt gttcagggaa tgtaaaccct ctctttttca ctggaaac                 228
```

<210> SEQ ID NO 57
<211> LENGTH: 123
<212> TYPE: DNA
<213> ORGANISM: Chlamydia sp.

<400> SEQUENCE: 57

```
gcttgtaacc aagaaacgct atttgcaagc aattctgcta aagaaaaagg cggggctatt     60

tatgccaagc acatggtatt gcgttataac ggtcctgttt ccttcattaa caacagcgct    120

aaa                                                                  123
```

-continued

<210> SEQ ID NO 58
<211> LENGTH: 258
<212> TYPE: DNA
<213> ORGANISM: Chlamydia sp.

<400> SEQUENCE: 58

```
ttgcaagcca gcgtgacttc tcccacccca gccaccgcat ctcctttagt tattcagaca     60

agtgcaaacc gttcagtgat ttctcgagc gaacgtcttt ctgaagaaga aaaaactcct    120

gataacctca cttcccaact acagcagcct atcgaactga aatccggacg cttagtttta    180

aaagatcgcg ctgtcctttc cgcgccttct ctctctcagg atcctcaagc tctcctcatt    240

atggaagcgg gaacttct                                                   258
```

<210> SEQ ID NO 59
<211> LENGTH: 168
<212> TYPE: DNA
<213> ORGANISM: Chlamydia sp.

<400> SEQUENCE: 59

```
gaacgtcttt ctgaagaaga aaaaactcct gataacctca cttcccaact acagcagcct     60

atcgaactga aatccggacg cttagtttta aaagatcgcg ctgtcctttc cgcgccttct    120

ctctctcagg atcctcaagc tctcctcatt atggaagcgg gaacttct                  168
```

<210> SEQ ID NO 60
<211> LENGTH: 153
<212> TYPE: DNA
<213> ORGANISM: Chlamydia sp.

<400> SEQUENCE: 60

```
ccccttcatt ccttagatac tgaaaaaagc gtaactatcc acgcccctaa cctttctatc     60

caaaagatct tcctctctaa ttctggagat gagaattttt atgaaaatgt agagcttctc    120

agtaaagagc aaaacaatat tcctctcctt act                                  153
```

<210> SEQ ID NO 61
<211> LENGTH: 168
<212> TYPE: DNA
<213> ORGANISM: Chlamydia sp.

<400> SEQUENCE: 61

```
tctaatttat tctatgctca cgacagctct gggaaaccta tcgataattg gcatcataga     60

agccttggct acctattcgg tatcagtact cacagtttag atgaccattc tttctgcttg    120

gctgcaggac aattactcgg gaaatcgtcc gattccttta ttacgtct                  168
```

<210> SEQ ID NO 62
<211> LENGTH: 198
<212> TYPE: DNA
<213> ORGANISM: Chlamydia sp.

<400> SEQUENCE: 62

```
tccttctcta aagaaggatt cggatcctgg catagcgttg cagtatccgg agaagtgtgc     60

gcatcgattc ctattgtatc caatggttcc ggactgttca gctccttctc tattttctct    120

aaactgcaag gattttcagg aacacaggac ggttttgagg agagttcggg agagattcgg    180

tccttttctg ccagctct                                                   198
```

<210> SEQ ID NO 63
<211> LENGTH: 183
<212> TYPE: DNA

<213> ORGANISM: Chlamydia sp.

<400> SEQUENCE: 63

```
tcgggagaga ttcggtcctt ttctgccagc tctttcagaa atatttcact tcctatagga     60

ataacatttg aaaaaaaatc ccaaaaaaca cgaacctact attactttct aggagcctac    120

atccaagacc tgaaacgtga tgtggaatcg ggacctgtag tgttactcaa aaatgccgtc    180

tcc                                                                  183
```

<210> SEQ ID NO 64
<211> LENGTH: 93
<212> TYPE: DNA
<213> ORGANISM: Chlamydia sp.

<400> SEQUENCE: 64

```
atggcgaact tggattcacg agcctacatg ttcaggctta cgaatcaaag agctctacac     60

agacttcaga cgctgttaaa tgtgtcttgt gtg                                 93
```

<210> SEQ ID NO 65
<211> LENGTH: 1500
<212> TYPE: DNA
<213> ORGANISM: Chlamydia sp.

<400> SEQUENCE: 65

```
atgcgacctg atcatatgaa cttctgttgt ctatgtgctg ctattttgtc atccacagcg     60

gtcctctttg gccaggatcc cttaggtgaa accgccctcc tcactaaaaa tcctaatcat    120

gtcgtctgta catttttga ggactgtacc atggagagcc tctttcctgc tctttgtgct    180

catgcatcac aagacgatcc tttgtatgta cttggaaatt cctactgttg gttcgtatct    240

aaactccata tcacggaccc caaagaggct ctttttaaag aaaaaggaga tctttccatt    300

caaaactttc gcttcctttc cttcacagat tgctcttcca aggaaagctc tccttctatt    360

attcatcaaa agaatggtca gttatccttg cgcaataatg gtagcatgag tttctgtcga    420

aatcatgctg aaggctctgg aggagccatc tctgcggatg ccttttctct acagcacaac    480

tatcttttca cagcttttga agagaattct tctaaaggaa atggcggagc cattcaggct    540

caaaccttct ctttatctag aaatgtgtcg cctatttctt tcgcccgtaa tcgtgcggat    600

ttaaatggcg gcgctatttg ctgtagtaat cttatttgtt cagggaatgt aaaccctctc    660

tttttcactg gaaactccgc cacgaatgga ggcgctattt gttgtatcag cgatctaaac    720

acctcagaaa aaggctctct ctctcttgct tgtaaccaag aaacgctatt tgcaagcaat    780

tctgctaaag aaaaaggcgg ggctatttat gccaagcaca tggtattgcg ttataacggt    840

cctgtttcct tcattaacaa cagcgctaaa ataggtggag ctatcgccat ccagtccgga    900

gggagtctct ctatccttgc aggtgaagga tctgttctgt tccagaataa ctcccaacgc    960

acctccgacc aaggtctagt aagaaacgcc atctacttag agaaagatgc gattctttct   1020

tccttagaag ctcgcaacgg agatattctt ttctttgatc ctattgtaca agaaagtagc   1080

agcaaagaat cgcctcttcc ctcctctttg caagccagcg tgacttctcc caccccagcc   1140

accgcatctc ctttagttat tcagacaagt gcaaaccgtt cagtgatttt ctcgagcgaa   1200

cgtctttctg aagaagaaaa aactcctgat aacctcactt cccaactaca gcagcctatc   1260

gaactgaaat ccggacgctt agttttaaaa gatcgcgctg tcctttccgc gccttctctc   1320

tctcaggatc ctcaagctct cctcattatg gaagcgggaa cttctttaaa aacttcctct   1380

gatttgaagt tagctacgct aagtattccc cttcattcct tagatactga aaaaagcgta   1440
```

-continued actatccacg cccctaacct ttctatccaa aagatcttcc tctctaattc tggagatgag 1500

<210> SEQ ID NO 66
<211> LENGTH: 49
<212> TYPE: DNA
<213> ORGANISM: Artificial
<220> FEATURE:
<223> OTHER INFORMATION: primer

<400> SEQUENCE: 66
atccagcaga gggtcgacgg gttccagatc ctacgaaaga gtcgctatc 49

<210> SEQ ID NO 67
<211> LENGTH: 51
<212> TYPE: DNA
<213> ORGANISM: Artificial
<220> FEATURE:
<223> OTHER INFORMATION: primer

<400> SEQUENCE: 67
atccagcaga gggtcgacgg ccttagaatc gcagagcaat ttccccattg a 51

<210> SEQ ID NO 68
<211> LENGTH: 12
<212> TYPE: DNA
<213> ORGANISM: Artificial
<220> FEATURE:
<223> OTHER INFORMATION: primer

<400> SEQUENCE: 68
aggcagaggc at 12

<210> SEQ ID NO 69
<211> LENGTH: 41
<212> TYPE: DNA
<213> ORGANISM: Artificial
<220> FEATURE:
<223> OTHER INFORMATION: primer

<400> SEQUENCE: 69
aggcagaggc atatgcgacc tgatcacatg aacttctgtt g 41

<210> SEQ ID NO 70
<211> LENGTH: 39
<212> TYPE: DNA
<213> ORGANISM: Artificial
<220> FEATURE:
<223> OTHER INFORMATION: primer

<400> SEQUENCE: 70
aggcagaggg tcgacgaacc tgtaagtggt ccccagatc 39

<210> SEQ ID NO 71
<211> LENGTH: 10
<212> TYPE: PRT
<213> ORGANISM: Artificial
<220> FEATURE:
<223> OTHER INFORMATION: fusion protein terminus

<400> SEQUENCE: 71

Met Arg Gly Ser His His His His His His
1 5 10

<210> SEQ ID NO 72
<211> LENGTH: 2871

-continued

<212> TYPE: DNA
<213> ORGANISM: Artificial
<220> FEATURE:
<223> OTHER INFORMATION: plasmid M15pREP

<400> SEQUENCE: 72

```
atgagaggat cgcatcacca tcaccatcac ggatccgcat gcgagctcgg taccccgggt     60
cgacgggttc cagatcctac gaaagagtcg ctatcaaata aaattagttt gacaggagac    120
actcacaatc tcactaactg ctatctcgat aacctacgct acatactggc tattctacaa    180
aaaactccca atgaaggagc tgctgtcaca ataacagatt acctaagctt ttttgataca    240
caaaaagaag gtatttattt tgcaaaaaat ctcacccctg aaagtggtgg tgcgattggt    300
tatgcgagtc ccaattctcc taccgtggag attcgtgata caataggtcc tgtaatcttt    360
gaaaataata cttgttgcag accatttaca tcgagtaatc ctaatgcagc tgttaataaa    420
ataagagaag gcggagccat tcatgctcaa aatctttaca taaatcacaa tcatgatgtg    480
gtcggattta tgaagaactt ttcttatgtc cgaggaggag ccattagtac cgctaatacc    540
tttgttgtga gcgagaatca gtcttgtttt ctctttatgg acaacatctg tattcaaact    600
aatacagcag gaaaaggtgg cgctatctat gctggaacga gcaattcttt tgagagtaat    660
aactgcgatc tcttctttat caataacgcc tgttgtgcag gaggagcgat cttctcccct    720
atctgttctc taacaggaaa tcgtggtaac atcgttttct ataacaatcg ctgctttaaa    780
aatgtagaaa cagcttcttc agaagcttct gatggaggag caattaaagt aactactcgc    840
ctagatgtta caggcaatcg tggtaggatc ttttttagtg acaatatcac aaaaaattat    900
ggcggagcta tttacgctcc tgtagttacc ctagtggata atggccctac ctactttata    960
aacaatgtcg ccaataataa ggggggcgct atctatatag acggaaccag caactccaaa   1020
atttctgccg accgccatgc tattattttt aatgaaaata ttgtgactaa tgtaactagt   1080
gcaaatggta ccagtacgtc agctaatcct cctagaagaa atgcaataac agtagcaagc   1140
tcctctggtg aaattctatt aggagcaggg agtagccaaa atttaatttt ttatgatcct   1200
attgaagtta gcaatgcagg ggtctctgtg tccttcaata aggaagctga tcaaacaggc   1260
tctgtagtat tttcaggagc tactgttaat tctgcagatt ttcatcaacg caatttacaa   1320
acaaaaacac ctgcacccct tactctcagt aatggttttc tatgtatcga agatcatgct   1380
cagcttacag tgaatcgatt cacacaaact gggggtgttg tttctcttgg gaatggagca   1440
gttctgagtt gctataaaaa tggtgcagga aattctgcta gcaatgcctc tataacactg   1500
aagcatattg gattgaatct ttcttccatt ctgaaaagtg gtgctgagat tcctttattg   1560
tgggtagagc ctacaaataa cagcaataac tatacagcag atactgcagc taccttttca   1620
ttaagtgatg taaaactctc actcattgat gactatggga attctcctta tgaatccaca   1680
gatctaaccc atgctctgtc atcacagcct atgctatcta tttctgaggc tagtgataac   1740
cagctaagat ctgatgatat ggatttctcg ggactaaatg tccctcatta tggatggcaa   1800
ggactttgga gttggggctg ggcaaaaact caagatccag aaccagcatc ttcagcaaca   1860
atcacagatc ccaaaaaagc caatagattc catagaacct tattactgac ttggcttcct   1920
gctgggtatg ttcctagccc gaaacacaga agtcccctca tagcgaatac cttatggggg   1980
aatatgctgc ttgcaacaga aagcttaaaa aatagtgcag aactgacacc tagtgatcat   2040
cctttctggg gaattacagg aggaggacta ggcatgatgg tttaccaaga acctcgagaa   2100
aatcatcctg gattccatat gcgctcttcc ggatactttg cggggatgat agcagggcaa   2160
```

-continued

```
acacatacct tctcattgaa attcagtcag acctacacca aactcaatga gcgttacgca   2220

aaaaacaacg tatcttctaa aaattactca tgccaaggag aaatgctctt ctcattgcaa   2280

gaaggtttct tgctggctaa attagttggt ctttacagct atggagatca taactgtcac   2340

catttctata cccaaggaga aaatctaaca tctcaaggga cgttccgtag tcaaacgatg   2400

ggaggtgctg tttttttga tctccctatg aaaccctttg gatcaacgca tatactgaca    2460

gctccctttt taggtgctct tggtatttat tctagcctgt ctcactttac tgaggtggga   2520

gcctatccgc gaagcttttc tacaaagact cctttgatca atgtcctagt ccctattgga   2580

gttaaaggta gctttatgaa tgctacccaa agacctcaag cctggactgt agaattggca   2640

taccaacccg ttctgtatag acaagaacta gagatcgcga cccagctcct agccagtaaa   2700

ggtatttggt ttggtagtgg aagcccctca tcgcgtcatg ccatgtccta taaaatctca   2760

cagcaaacac aacctttgag ttggttaact ctccatttcc agtatcatgg attctactcc   2820

tcttcaacct tctgtaatta tctcaatggg gaaattgctc tgcgattcta a            2871
```

```
<210> SEQ ID NO 73
<211> LENGTH: 956
<212> TYPE: PRT
<213> ORGANISM: Artificial
<220> FEATURE:
<223> OTHER INFORMATION: plasmid M15pREP

<400> SEQUENCE: 73

Met Arg Gly Ser His His His His His His Gly Ser Ala Cys Glu Leu
1               5                   10                  15

Gly Thr Pro Gly Arg Arg Val Pro Asp Pro Thr Lys Glu Ser Leu Ser
            20                  25                  30

Asn Lys Ile Ser Leu Thr Gly Asp Thr His Asn Leu Thr Asn Cys Tyr
        35                  40                  45

Leu Asp Asn Leu Arg Tyr Ile Leu Ala Ile Leu Gln Lys Thr Pro Asn
    50                  55                  60

Glu Gly Ala Ala Val Thr Ile Thr Asp Tyr Leu Ser Phe Phe Asp Thr
65                  70                  75                  80

Gln Lys Glu Gly Ile Tyr Phe Ala Lys Asn Leu Thr Pro Glu Ser Gly
                85                  90                  95

Gly Ala Ile Gly Tyr Ala Ser Pro Asn Ser Pro Thr Val Glu Ile Arg
            100                 105                 110

Asp Thr Ile Gly Pro Val Ile Phe Glu Asn Asn Thr Cys Cys Arg Pro
        115                 120                 125

Phe Thr Ser Ser Asn Pro Asn Ala Ala Val Asn Lys Ile Arg Glu Gly
    130                 135                 140

Gly Ala Ile His Ala Gln Asn Leu Tyr Ile Asn His Asn His Asp Val
145                 150                 155                 160

Val Gly Phe Met Lys Asn Phe Ser Tyr Val Arg Gly Gly Ala Ile Ser
                165                 170                 175

Thr Ala Asn Thr Phe Val Val Ser Glu Asn Gln Ser Cys Phe Leu Phe
            180                 185                 190

Met Asp Asn Ile Cys Ile Gln Thr Asn Thr Ala Gly Lys Gly Gly Ala
        195                 200                 205

Ile Tyr Ala Gly Thr Ser Asn Ser Phe Glu Ser Asn Asn Cys Asp Leu
    210                 215                 220

Phe Phe Ile Asn Asn Ala Cys Cys Ala Gly Gly Ala Ile Phe Ser Pro
225                 230                 235                 240
```

-continued

```
Ile Cys Ser Leu Thr Gly Asn Arg Gly Asn Ile Val Phe Tyr Asn Asn
                245                 250                 255

Arg Cys Phe Lys Asn Val Glu Thr Ala Ser Ser Glu Ala Ser Asp Gly
            260                 265                 270

Gly Ala Ile Lys Val Thr Thr Arg Leu Asp Val Thr Gly Asn Arg Gly
        275                 280                 285

Arg Ile Phe Phe Ser Asp Asn Ile Thr Lys Asn Tyr Gly Gly Ala Ile
    290                 295                 300

Tyr Ala Pro Val Val Thr Leu Val Asp Asn Gly Pro Thr Tyr Phe Ile
305                 310                 315                 320

Asn Asn Val Ala Asn Asn Lys Gly Gly Ala Ile Tyr Ile Asp Gly Thr
                325                 330                 335

Ser Asn Ser Lys Ile Ser Ala Asp Arg His Ala Ile Ile Phe Asn Glu
            340                 345                 350

Asn Ile Val Thr Asn Val Thr Ser Ala Asn Gly Thr Ser Thr Ser Ala
        355                 360                 365

Asn Pro Pro Arg Arg Asn Ala Ile Thr Val Ala Ser Ser Ser Gly Glu
    370                 375                 380

Ile Leu Leu Gly Ala Gly Ser Ser Gln Asn Leu Ile Phe Tyr Asp Pro
385                 390                 395                 400

Ile Glu Val Ser Asn Ala Gly Val Ser Val Ser Phe Asn Lys Glu Ala
                405                 410                 415

Asp Gln Thr Gly Ser Val Val Phe Ser Gly Ala Thr Val Asn Ser Ala
            420                 425                 430

Asp Phe His Gln Arg Asn Leu Gln Thr Lys Thr Pro Ala Pro Leu Thr
        435                 440                 445

Leu Ser Asn Gly Phe Leu Cys Ile Glu Asp His Ala Gln Leu Thr Val
    450                 455                 460

Asn Arg Phe Thr Gln Thr Gly Gly Val Val Ser Leu Gly Asn Gly Ala
465                 470                 475                 480

Val Leu Ser Cys Tyr Lys Asn Gly Ala Gly Asn Ser Ala Ser Asn Ala
                485                 490                 495

Ser Ile Thr Leu Lys His Ile Gly Leu Asn Leu Ser Ser Ile Leu Lys
            500                 505                 510

Ser Gly Ala Glu Ile Pro Leu Leu Trp Val Glu Pro Thr Asn Asn Ser
        515                 520                 525

Asn Asn Tyr Thr Ala Asp Thr Ala Ala Thr Phe Ser Leu Ser Asp Val
    530                 535                 540

Lys Leu Ser Leu Ile Asp Asp Tyr Gly Asn Ser Pro Tyr Glu Ser Thr
545                 550                 555                 560

Asp Leu Thr His Ala Leu Ser Ser Gln Pro Met Leu Ser Ile Ser Glu
                565                 570                 575

Ala Ser Asp Asn Gln Leu Arg Ser Asp Asp Met Asp Phe Ser Gly Leu
            580                 585                 590

Asn Val Pro His Tyr Gly Trp Gln Gly Leu Trp Ser Trp Gly Trp Ala
        595                 600                 605

Lys Thr Gln Asp Pro Glu Pro Ala Ser Ser Ala Thr Ile Thr Asp Pro
    610                 615                 620

Lys Lys Ala Asn Arg Phe His Arg Thr Leu Leu Leu Thr Trp Leu Pro
625                 630                 635                 640

Ala Gly Tyr Val Pro Ser Pro Lys His Arg Ser Pro Leu Ile Ala Asn
                645                 650                 655

Thr Leu Trp Gly Asn Met Leu Leu Ala Thr Glu Ser Leu Lys Asn Ser
```

-continued

```
        660                 665                 670

Ala Glu Leu Thr Pro Ser Asp His Pro Phe Trp Gly Ile Thr Gly Gly
    675                 680                 685

Gly Leu Gly Met Met Val Tyr Gln Glu Pro Arg Glu Asn His Pro Gly
    690                 695                 700

Phe His Met Arg Ser Ser Gly Tyr Phe Ala Gly Met Ile Ala Gly Gln
705                 710                 715                 720

Thr His Thr Phe Ser Leu Lys Phe Ser Gln Thr Tyr Thr Lys Leu Asn
                725                 730                 735

Glu Arg Tyr Ala Lys Asn Asn Val Ser Ser Lys Asn Tyr Ser Cys Gln
            740                 745                 750

Gly Glu Met Leu Phe Ser Leu Gln Glu Gly Phe Leu Leu Ala Lys Leu
        755                 760                 765

Val Gly Leu Tyr Ser Tyr Gly Asp His Asn Cys His His Phe Tyr Thr
    770                 775                 780

Gln Gly Glu Asn Leu Thr Ser Gln Gly Thr Phe Arg Ser Gln Thr Met
785                 790                 795                 800

Gly Gly Ala Val Phe Phe Asp Leu Pro Met Lys Pro Phe Gly Ser Thr
                805                 810                 815

His Ile Leu Thr Ala Pro Phe Leu Gly Ala Leu Gly Ile Tyr Ser Ser
            820                 825                 830

Leu Ser His Phe Thr Glu Val Gly Ala Tyr Pro Arg Ser Phe Ser Thr
        835                 840                 845

Lys Thr Pro Leu Ile Asn Val Leu Val Pro Ile Gly Val Lys Gly Ser
    850                 855                 860

Phe Met Asn Ala Thr Gln Arg Pro Gln Ala Trp Thr Val Glu Leu Ala
865                 870                 875                 880

Tyr Gln Pro Val Leu Tyr Arg Gln Glu Leu Glu Ile Ala Thr Gln Leu
                885                 890                 895

Leu Ala Ser Lys Gly Ile Trp Phe Gly Ser Gly Ser Pro Ser Ser Arg
            900                 905                 910

His Ala Met Ser Tyr Lys Ile Ser Gln Gln Thr Gln Pro Leu Ser Trp
        915                 920                 925

Leu Thr Leu His Phe Gln Tyr His Gly Phe Tyr Ser Ser Ser Thr Phe
    930                 935                 940

Cys Asn Tyr Leu Asn Gly Glu Ile Ala Leu Arg Phe
945                 950                 955
```